(12) United States Patent
Brittain et al.

(10) Patent No.: US 9,688,624 B2
(45) Date of Patent: Jun. 27, 2017

(54) DP2 ANTAGONIST AND USES THEREOF

(75) Inventors: Jason Edward Brittain, El Cajon, CA (US); Christopher David King, Carlsbad, CA (US); Brian Andrew Stearns, Encinitas, CA (US)

(73) Assignee: Brickell Biotech, Inc., Boulder, CO (US)

( * ) Notice: Subject to any disclaimer, the term of this patent is extended or adjusted under 35 U.S.C. 154(b) by 516 days.

(21) Appl. No.: 13/519,292

(22) PCT Filed: Jan. 5, 2011

(86) PCT No.: PCT/US2011/020264
§ 371 (c)(1),
(2), (4) Date: Oct. 31, 2012

(87) PCT Pub. No.: WO2011/085033
PCT Pub. Date: Jul. 14, 2011

(65) Prior Publication Data
US 2013/0053444 A1 Feb. 28, 2013

Related U.S. Application Data

(60) Provisional application No. 61/292,807, filed on Jan. 6, 2010.

(51) Int. Cl.
C07C 323/41 (2006.01)

(52) U.S. Cl.
CPC ........ *C07C 323/41* (2013.01); *C07B 2200/13* (2013.01)

(58) Field of Classification Search
CPC .. C07C 321/10; C07B 2200/13; A61K 31/196
See application file for complete search history.

(56) References Cited

U.S. PATENT DOCUMENTS

| | | |
|---|---|---|
| 5,239,084 A | 8/1993 | Guerry et al. |
| 5,334,598 A | 8/1994 | Bagley et al. |
| 5,668,176 A | 9/1997 | Bagley et al. |
| 5,827,868 A | 10/1998 | Misra et al. |
| 6,028,080 A | 2/2000 | Ackermann et al. |
| 6,429,213 B1 | 8/2002 | Xue et al. |
| 6,617,351 B1 | 9/2003 | Arnold et al. |
| 6,858,626 B2 | 2/2005 | Xue et al. |
| 6,884,593 B1 | 4/2005 | Hirai et al. |
| 7,005,440 B1 | 2/2006 | Jayyosi et al. |
| 7,144,913 B2 | 12/2006 | Wang et al. |
| 7,321,001 B2 | 1/2008 | Fu et al. |
| 8,071,807 B2 | 12/2011 | Hutchinson et al. |
| 8,247,602 B2 | 8/2012 | Hutchinson et al. |
| 2001/0047027 A1 | 11/2001 | Labelle et al. |
| 2002/0198251 A1 | 12/2002 | Sundermann et al. |
| 2005/0154044 A1 | 7/2005 | Beaulieu et al. |
| 2005/0272756 A1 | 12/2005 | Leblanc et al. |
| 2006/0100425 A1 | 5/2006 | Bennani et al. |
| 2006/0106081 A1 | 5/2006 | Bennani et al. |
| 2007/0155726 A1 | 7/2007 | Arnaiz et al. |
| 2008/0085891 A1 | 4/2008 | Fu et al. |
| 2008/0167378 A1 | 7/2008 | Fukatsu et al. |
| 2008/0306109 A1 | 12/2008 | Hynd et al. |
| 2009/0048238 A1 | 2/2009 | Aebi et al. |
| 2009/0186923 A1 | 7/2009 | Armer et al. |
| 2009/0197959 A1 | 8/2009 | Hutchinson et al. |
| 2010/0173313 A1 | 7/2010 | Bain et al. |
| 2011/0039852 A1 | 2/2011 | Hutchinson et al. |
| 2011/0098352 A1 | 4/2011 | Hutchinson et al. |
| 2011/0144160 A1* | 6/2011 | Hutchinson .......... A61K 31/235 514/330 |

FOREIGN PATENT DOCUMENTS

| | | |
|---|---|---|
| EP | 1170594 A2 | 1/2002 |
| GB | 2461629 B | 5/2010 |
| JP | 2004-182657 A | 7/2004 |
| WO | WO-95-03044 A1 | 2/1995 |
| WO | WO-99-11605 A1 | 3/1999 |
| WO | WO-99-65867 A1 | 12/1999 |
| WO | WO-03-006011 | 1/2003 |
| WO | WO-2004-058164 A2 | 7/2004 |
| WO | WO-2004-096777 A1 | 11/2004 |

(Continued)

OTHER PUBLICATIONS

Arima et al., "Prostaglandin D2 Receptors DP and CRTH2 in the Pathogenesis of Asthma," Curr. Mol. Med. 8: 365-375 (2008).

Brannan et al., "Inhibition of mast cell PGD2 release protects against mannitol-induced airway narrowing," Eur Respir J 27: 944-950 (2006).

Cossette et al., "Agonist and antagonist effects of 15R-Prostaglandin (PG) D2 and 11-methylene-PGD2 on human eosinophils and basophils," J Pharmacol Exp Therap 320:173-179 (2007).

Crosignani et al., "Discovery of a new class of potent, selective, and orally bioavailable CRTH2(DP2) receptor antagonists for the treatment of allergic inflammatory diseases," J Med Chem 51: 2227-2242 (2008).

Evans et al., "Seeing the future of bioactive lipid drug targets," Nature Chem Biol 6: 476-479 (2010).

Hata et al., "Pharmacology and signaling of prostaglandin receptors: multiple roles in inflammation and immune modulation," Pharmacol. Ther. 103: 147-166 (2004).

(Continued)

*Primary Examiner* — Paul A Zucker
(74) *Attorney, Agent, or Firm* — Ted Whitlock

(57) ABSTRACT

Described herein is the $DP_2$ antagonist 2-(3-(2-((tert-butylthio)methyl)-4-(2,2-dimethyl-propionylamino)phenoxy)-4-methoxyphenyl)acetic acid, or a pharmaceutically acceptable salt thereof. Also described are methods of preparing the $DP_2$ antagonist, or a pharmaceutically acceptable salt thereof. Also described herein are pharmaceutical compositions suitable for administration to a mammal that include the $DP_2$ antagonist, or a pharmaceutically acceptable salt thereof, and methods of using such pharmaceutical compositions for treating respiratory diseases or conditions, allergic diseases or conditions, inflammatory diseases or conditions, as well as other prostaglandin $D_2$-dependent or prostaglandin $D_2$-mediated diseases or conditions.

11 Claims, 10 Drawing Sheets

(56) References Cited

FOREIGN PATENT DOCUMENTS

| | | |
|---|---|---|
| WO | WO-2005-040114 A1 | 5/2005 |
| WO | WO-2005-044260 A1 | 5/2005 |
| WO | WO-2005-051373 A1 | 6/2005 |
| WO | WO-2005-100298 | 10/2005 |
| WO | WO-2005-105727 A1 | 10/2005 |
| WO | WO-2006-005909 A1 | 1/2006 |
| WO | WO-2006-018325 A1 | 2/2006 |
| WO | WO-2006-0529798 A2 | 5/2006 |
| WO | WO-2006-056854 | 6/2006 |
| WO | WO-2006-125596 A1 | 11/2006 |
| WO | WO 2007-037187 A1 | 4/2007 |
| WO | WO-2007-039736 A1 | 4/2007 |
| WO | WO-2007-068894 A2 | 6/2007 |
| WO | WO-2008-024746 A1 | 2/2008 |
| WO | WO-2008-154642 A2 | 12/2008 |
| WO | WO-2009-003861 A1 | 1/2009 |
| WO | WO-2009-044147 A1 | 4/2009 |
| WO | WO-2009-063202 A2 | 5/2009 |
| WO | WO-2009-063215 A2 | 5/2009 |
| WO | WO-2009-102893 A2 | 8/2009 |
| WO | WO-2009-145989 A2 | 12/2009 |
| WO | WO-2010-003120 A2 | 1/2010 |
| WO | WO-2010-003127 A2 | 1/2010 |
| WO | WO-2010-039977 A2 | 4/2010 |
| WO | WO-2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |

OTHER PUBLICATIONS

Jatakanon et al., "Neutrophilic Inflammation in Severe Persistent Asthma," Am J Respir Crit Care Med 160: 1532-1539 (1999).

Johnston et al., "Prostaglandin D2-induced bronchoconstriction is mediated only in part by the thromboxane prostanoid receptor," Eur Respir J 8: 411-415 (1995).

Kim et al., "Regulation of immune cells by eicosanoid receptors," The Scientific World Journal 7: 1307-1328 (2007).

Kostens et al., "Emerging roles of DP and CRTH2 in allergic inflammation," Trends Mol. Med. 12: 148-158 (2006).

Ly et al., "Small-molecule CRTH2 antagonists for the treatment of allergic inflammation: an overview," Exp Opin Invest Drugs 14: 769 (2005).

Medina et al., "PGD2 Antagonists," Annual Reports Med. Chem. 41: 221-235 (2006).

PCT/US09/049621 ISR and Written Opinion dated Mar. 15, 2010.
PCT/US09/049631 ISR and Written Opinion dated Feb. 24, 2010.
PCT/US10/43598 Search Report and Written Opinion mailed Apr. 22, 2011.
PCT/US10/43599 Search Report and Written Opinion mailed Apr. 28, 2011.
PCT/US2011/020264 International Preliminary Report on Patentability and Written Opinion dated Sep. 28, 2011.
PCT/US2011/020264 International Search Report dated Sep. 28, 2011.

Pettipher et al., "Antagonism of the prostaglandin D2 receptors DP1 and CRTH2 as an approach to treat allergic diseases," Nature Reviews/Drug Discovery 6: 313-325 (2007).

Pettipher et al., "Antagonists of the prostaglandin D2 receptor CRTH2," Drug News Perspect 21: 317-322 (2008).

Pettipher et al., "The roles of the prostaglandin D2 receptors DP(1) and CRTH2 in promoting allergic responses," Br J Pharmacol 153: 5191 (2008).

Sagel et al., "Sputum biomarkers of inflammation in cystic fibrosis lung disease," Proc Am Thorac Soc 4: 406-417 (2007).

Sandig et al., "Contrary prostaglandins: the opposing roles of PGD2 and its metabolites in leukocyte function," J Leukocyte Biology 81: 372-382 (2007).

Science IP Structure Search dated Mar. 20, 2008.

Scott et al., "Discovery and optimization of a biphenylacetic acid series of prostaglandin D2 receptor DP2 antagonists with efficacy: a murine model of allergic rhinitis," Bioorg Med Chem Ltrs doi: 10.1016fj.bmcl.2011.01.024 (2011).

Srinivas et al., "Biaryl amino acid templates I place of D-Pro-L-Pro in cyclic beta-hairpin cationic antimicrobial peptidomimetics," Organic & Biomolecular Chemistry 5: 3100-3105 (2007).

Stearns et al., "Novel tricyclic antagonists of the prostaglandin D2 receptor DP2 with efficacy in a murine model of allergic rhinitis," Bioorg Med Chem Ltrs 19:4647-4651 (2009).

Stebbins et al., "DP2 receptor antagonists: novel therapeutic target for COPD," Mol Cell Pharmacol 2: 89-96 (2010).

Stebbins et al., "Pharmacological blockade of the DP2 receptor inhibits cigarette smoke-induced inflammation, mucus cell metaplasia, and epithelial hyperplasia in the mouse lung," J Pharmacol Exp Ther 332: 764-775 (2010).

Stebbins et al., "Therapeutic efficacy of AM156, a novel prostanoid DP2 receptor antagonist, in murine models of allergic rhinitis and house dust mite-induced pulmonary inflammation," Eur J Pharmacol 638: 142-149 (2010).

Stock et al., "Sodium [2'-[(cyclopropanecarbonyl-thyl-amino)-methyl]-4'-(6-ethoxy-pyridin-3-yl)-6-methoxy-biphenyl-3-yl]-acetate (AM432): a potent, selective prostaglandin D2 receptor antagonist," Bioorg Med Chem Ltrs 21: 1036-1040 (2011).

Sugimoto et al., "An orally bioavailable small molecule antagonist of CRTH2, ramatroban (BAY U3405), inhibits prostaglandin D2-induced eosinophil migration in vitro," J Pharmcol Exper Therap 305: 347-352 (2003).

Takeshita et al., "CRTH2 is a prominent effector in contact hypersensitivity-induced neutrophil inflammtion," Intl Immunol 16: 947-959 (2004).

Tirouvanziam t al., "Profound functional and signaling changes in viable inflammatory neutrophils homing to cystic fibrosis airways," PNAS 105: 4335-4339 (2008).

Ulven et al., "Minor structural modifications cover the dual TP/CRTH2," J Med Chem 48: 897-900 (2005).

Ulven et al., "Targeting the prostaglandin D2 receptors DP and CRTH2 for treatment of inflammation," Curr. Topics Med. Chem. 6: 1427-1444 (2006).

Wardlaw et al., "New insights into the relationship between airway inflammation and asthma," Clinical Science 103: 201-211 (2002).

* cited by examiner

XRPD of amorphous Compound 2

Pattern 1 of Compound 2

Pattern 1 of Compound 1

Pattern 2 of Compound 1

Pattern 3 of Compound 1

Pattern 4 of Compound 1

DP2 ANTAGONIST AND USES THEREOF

RELATED APPLICATIONS

This application is filed pursuant to 35 U.S.C. 371 as a United States National Phase Application of International Application No. PCT/US2011/020264, entitled "DP$_2$ ANTAGONIST AND USES THEREOF", filed on Jan. 5, 2011, which claims the benefit of U.S. provisional patent application No. 61/292,807 entitled "DP$_2$ ANTAGONIST AND USES THEREOF" filed on Jan. 6, 2010, all of which are incorporated by reference in their entirety

FIELD OF THE INVENTION

Described herein is the DP$_2$ antagonist 2-(3-(2-((tert-butylthio)methyl)-4-(2,2-dimethyl-propionylamino)phenoxy)-4-methoxyphenyl)acetic acid (Compound 1), pharmaceutically acceptable salts, solvates, polymorphs, amorphous phases, metabolites thereof, as well as pharmaceutical compositions thereof, and methods of use thereof in the treatment or prevention of diseases or conditions associated with DP$_2$ activity.

BACKGROUND OF THE INVENTION

Prostaglandins are acidic lipids derived from the metabolism of arachidonic acid by the action of cyclooxygenase enzymes and downstream synthases. Prostaglandins have a diverse range of activities and have a well recognized role in a variety of disease or conditions, such as allergic diseases or conditions, inflammatory diseases or conditions, and respiratory diseases or conditions. Prostaglandin D$_2$ (PGD$_2$) is an acidic lipid mediator derived from the metabolism of arachidonic acid by cyclooxygenases and PGD$_2$ synthases. PGD$_2$ is produced by mast cells, macrophages and Th2 lymphocytes in response to local tissue damage as well as allergic inflammation in diseases such as asthma, rhinitis, and atopic dermatitis. Exogenous PGD$_2$ applied to bronchial airways elucidates many characteristics of an asthmatic response suggesting that PGD$_2$ plays an important pro-inflammatory role in allergic diseases.

PGD$_2$ binds to a number of receptors, which include the thromboxane-type prostanoid (TP) receptor, PGD$_2$ receptor (DP, also known as DP$_1$) and chemoattractant receptor-homologous molecule expressed on Th2 cells (CRTH2; also known as DP$_2$). DP$_2$ is associated with promoting chemotaxis and activation of Th2 lymphocytes, eosinophils and basophils. In particular, PGD$_2$ binds to DP$_2$, and mediates its effects through a G$_i$-dependant elevation in calcium levels and reduction of intracellular cyclic AMP. In Th2 lymphocytes, IL4, IL5 and IL13 cytokine production is stimulated. These cytokines have been implicated in numerous biological actions including, by way of example only, immunoglobulin E production, airway response, mucous secretion, and eosinophil recruitment.

SUMMARY OF THE INVENTION

Described herein is 2-(3-(2-((tert-butylthio)methyl)-4-(2,2-dimethyl-propionylamino)phenoxy)-4-methoxyphenyl) acetic acid (Compound 1) including all pharmaceutically acceptable solvates (including hydrates), prodrugs, polymorphs, amorphous phases and metabolites thereof or a pharmaceutically acceptable salt of Compound 1 including (including hydrates), prodrugs, polymorphs, amorphous phases and metabolites thereof, and methods of uses thereof. Compound 1, as well as the pharmaceutically acceptable salts thereof, are used in the manufacture of medicaments for the treatment or prevention of prostaglandin D$_2$ mediated and/or prostaglandin D$_2$ dependent diseases, disorders, or conditions. Also described are pharmacokinetic and pharmacodynamic properties of such formulations in mammals, including humans. Compound 1 is a DP$_2$ antagonist.

Described herein are pharmaceutical compositions comprising Compound 1, or a pharmaceutically acceptable salt thereof (e.g. the sodium salt) as the active ingredient in the pharmaceutical composition.

In one aspect, provided herein is a crystalline form of 2-(3-(2-((tert-butylthio)methyl)-4-(2,2-dimethyl-propionylamino)phenoxy)-4-methoxyphenyl)acetic acid (Compound 1). In some embodiments, the crystalline form of Compound 1 has an X-ray powder diffraction (XRPD) pattern with characteristic peaks at 11.4° 2-Theta, 16.9° 2-Theta, 17.9° 2-Theta, and 18.9° 2-Theta. In some embodiments, the crystalline form of Compound 1 has an X-ray powder diffraction (XRPD) pattern substantially the same as shown in FIG. 4. In some embodiments, the crystalline form of Compound 1 has a DSC thermogram with endotherms at about 32° C., about 77° C., and about 136° C.

In some embodiments, the crystalline form of Compound 1 has an X-ray powder diffraction (XRPD) pattern with characteristic peaks at 11.5° 2-Theta, 17.9° 2-Theta, 19.0° 2-Theta, and 20.6° 2-Theta. In some embodiments, the X-ray powder diffraction (XRPD) pattern has at least one additional characteristic peak selected from 12.3° 2-Theta, 13.6° 2-Theta, 16.5° 2-Theta, 16.9° 2-Theta, 22.5° 2-Theta, 22.7° 2-Theta, and 23.0° 2-Theta. In some embodiments, the crystalline form of Compound 1 has an X-ray powder diffraction (XRPD) pattern substantially the same as shown in FIG. 5. In some embodiments, the crystalline form of Compound 1 has a DSC thermogram with endotherms at about 52° C. and about 139° C.

In some embodiments, the crystalline form of Compound 1 has an X-ray powder diffraction (XRPD) pattern with characteristic peaks at 8.1° 2-Theta, 11.9° 2-Theta, 18.2° 2-Theta, and 18.9° 2-Theta. In some embodiments, the X-ray powder diffraction (XRPD) pattern has at least one additional characteristic peak selected from 6.3° 2-Theta, 13.5° 2-Theta, 16.3° 2-Theta, 16.5° 2-Theta, 18.7° 2-Theta, 19.5° 2-Theta, 21.5° 2-Theta, and 23.4° 2-Theta. In some embodiments, the crystalline form of Compound 1 has an X-ray powder diffraction (XRPD) pattern substantially the same as shown in FIG. 6. In some embodiments, the crystalline form of Compound 1 has a DSC thermogram with endotherms at about 38° C. and about 147° C.

In some embodiments, the crystalline form of Compound 1 has an X-ray powder diffraction (XRPD) pattern with characteristic peaks at 12.3° 2-Theta, 16.5° 2-Theta, 20.6° 2-Theta, and 22.0° 2-Theta. In some embodiments, the X-ray powder diffraction (XRPD) pattern has at least one additional characteristic peak selected from 4.1° 2-Theta, 8.2° 2-Theta, 11.4° 2-Theta, 18.5° 2-Theta, and 24.8° 2-Theta. In some embodiments, the crystalline form of Compound 1 has an X-ray powder diffraction (XRPD) pattern substantially the same as shown in FIG. 7.

In one aspect, provided herein is a crystalline form of 2-(3-(2-((tert-butylthio)methyl)-4-(2,2-dimethyl-propionylamino)phenoxy)-4-methoxyphenyl)acetic acid, sodium salt (Compound 2). In some embodiments, the crystalline form of Compound 2 has an X-ray powder diffraction (XRPD) pattern with characteristic peaks at 3.7° 2-Theta, 13.5° 2-Theta, 17.1° 2-Theta, and 18.8° 2-Theta. In some embodiments, the X-ray powder diffraction (XRPD) pattern has at least one additional characteristic peak selected from 6.8° 2-Theta, 8.7° 2-Theta, 11.1° 2-Theta, 15.7° 2-Theta, 17.5° 2-Theta, and 17.9° 2-Theta. In some embodiments, the crystalline form of Compound 2 has an X-ray powder diffraction (XRPD) pattern substantially the same as shown in FIG. 2. In some embodiments, the crystalline form of Compound 2 has a DSC thermogram with endotherms at about 70° C., about 122° C., and about 138° C. In some embodiments, the crystalline form of Compound 2 has a DSC thermogram substantially the same as FIG. 3.

In one aspect, provided herein is a pharmaceutically acceptable salt of 2-(3-(2-(2-((tert-butylthio)methyl)-4-(2,2-dimethyl-propionylamino)phenoxy)-4-methoxyphenyl)acetic acid (Compound 1). In some embodiments, the pharmaceutically acceptable salt is a calcium salt, potassium salt, sodium salt, ammonium salt, L-arginine salt, L-lysine salt, and N-methyl-D-glucamine salt. In some embodiments, the pharmaceutically acceptable salt is a sodium salt. In some embodiments, the pharmaceutically acceptable salt has the structure of Compound 2:

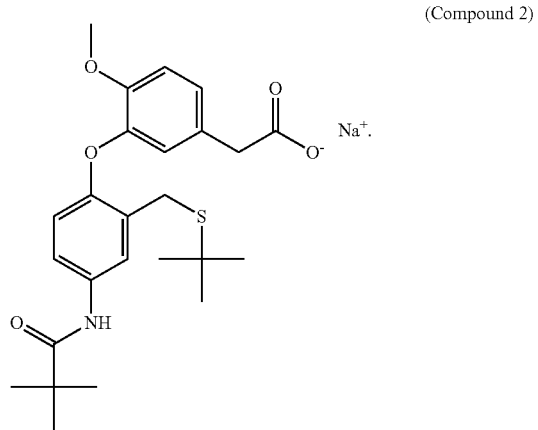

(Compound 2)

In some embodiments, Compound 2 is amorphous.

In some embodiments, Compound 2 is crystalline.

In some embodiments, Compound 2 is crystalline and was obtained from a solution comprising heptane and acetone.

In some embodiments, Compound 2 is crystalline and comprises a detectable amount of heptane or acetone or a combination of heptane and acetone.

In some embodiments, Compound 2 is crystalline and has at least one of the following properties:
(a) an X-ray powder diffraction (XRPD) pattern with characteristic peaks at 3.7° 2-Theta, 13.5° 2-Theta, 17.1° 2-Theta, and 18.8° 2-Theta;
(b) an X-ray powder diffraction (XRPD) pattern substantially the same as shown in FIG. 2;
(c) a DSC thermogram with endotherms at about 70° C., about 122° C., and about 138° C.;
(d) a DSC thermogram substantially the same as FIG. 3.

In some embodiments, Compound 2 is crystalline and has at least two of the properties selected from (a), (b), (c), and (d). In some embodiments, Compound 2 is crystalline and has at least three of the properties selected from (a), (b), (c), and (d). In some embodiments, Compound 2 is crystalline and has properties (a), (b), (c), and (d).

In some embodiments, provided herein is a pharmaceutical composition comprising Compound 1 (amorphous or crystalline) or a pharmaceutically acceptable salt of Compound 1. In some embodiments, the pharmaceutically acceptable salt of Compound 1 is Compound 2 (amorphous or crystalline).

In some embodiments, the pharmaceutical composition comprises at least inactive ingredient selected from pharmaceutically acceptable carriers, diluents and excipients.

In some embodiments, the pharmaceutical composition comprises Compound 2. In some embodiments, the pharmaceutical composition comprises amorphous Compound 2. In some embodiments, the pharmaceutical composition comprises crystalline Compound 2. In some embodiments, Compound 2 is greater than 96% pure. In some embodiments, Compound 2 is greater than 97% pure. In some embodiments, Compound 2 is greater than 98% pure.

In some embodiments, the pharmaceutical composition is in a form suitable for oral administration to a mammal. In some embodiments, the pharmaceutical composition is in the form of a pill, capsule, tablet, aqueous solution, aqueous suspension, non-aqueous solution, or non-aqueous suspension.

In some embodiments, the pharmaceutical composition is in a form suitable for nasal or inhalation administration to a mammal.

In some embodiments, the pharmaceutical composition is in the form of a capsule. In some embodiments, the pharmaceutical composition is in the form of an immediate release capsule or an enteric coated capsule.

In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet.

In some embodiments, the pharmaceutical composition is in the form of an aqueous solution or aqueous suspension.

In some embodiments, a single dose of the pharmaceutical composition comprises about 0.5 mg to about 1000 mg of Compound 2. In some embodiments, a single dose of the pharmaceutical composition comprises about 5 mg to about 500 mg of Compound 2. In some embodiments, a single dose of the pharmaceutical composition when administered to adult human subjects provides about 70-100% inhibition of ex vivo $PGD_2$-stimulated eosinophil shape change in whole blood after about 8 hours following administration. In some embodiments, a single dose of the pharmaceutical composition when administered to adult human subjects provides about 70-100% inhibition of ex vivo $PGD_2$-stimulated eosinophil shape change in whole blood after about 24 hours following administration. In some embodiments, a single dose of the pharmaceutical composition when administered to adult human subjects twice-a-day provides about 70-100% inhibition of ex vivo $PGD_2$-stimulated eosinophil shape change in whole blood after about 24 hours following administration of the first dose. In some embodiments, a single dose of the pharmaceutical composition when administered to adult human subjects provides about 20-60% inhibition of ex vivo $PGD_2$-stimulated eosinophil shape change in whole blood after about 24 hours following administration. In some embodiments, the adult human subjects are in a fasted state. In some embodiments, the adult human subjects are healthy.

In one aspect provided herein is an oral solid dosage form pharmaceutical composition comprising 2-(3-(2-((tert-butylthio)methyl)-4-(2,2-dimethyl-propionylamino)phenoxy)-4-methoxyphenyl)acetic acid (Compound 1) or a pharmaceutically acceptable salt of 2-(3-(2-((tert-butylthio)methyl)-4-(2,2-dimethyl-propionylamino)phenoxy)-4- methoxyphenyl)acetic acid (Compound 1). In some embodiments, the pharmaceutically acceptable salt is a calcium salt, potassium salt, sodium salt, magnesium salt, ammonium salt, L-arginine salt, L-lysine salt, and N-methyl-D-glucamine salt. In some embodiments, the pharmaceutically acceptable salt of Compound 1 is 2-(3-(2-((tert-butylthio)methyl)-4-(2,2-dimethyl-propionylamino) phenoxy)-4-methoxyphenyl)acetic acid, sodium salt (Compound 2).

In some embodiments, the oral solid dosage form is in the form of a tablet, pill or capsule.

In some embodiments, the pharmaceutical composition comprises about 1 mg to about 1000 mg of Compound 2. In some embodiments, the pharmaceutical composition comprises about 1 mg, about 3 mg, about 5 mg, about 10 mg, about 15 mg, about 30 mg, about 50 mg, about 100 mg, about 150 mg, about 200 mg, about 250 mg, about 300 mg, about 500 mg, about 600 mg or about 1000 mg of Compound 2.

In some embodiments, the oral solid dosage form pharmaceutical composition is in the form of a capsule. In some embodiments, the capsule is in the form of a hard gelatine capsule or hypromellose (HPMC) capsule. In some embodiments, the capsule comprises at least one excipient in addition to the hard gelatine capsule or hypromellose (HPMC) capsule. In some embodiments, the capsule is an immediate release capsule or an enteric coated capsule.

In some embodiments, the oral solid dosage form is in the form of a tablet. In some embodiments, the oral solid dosage form is in the form of an immediate release tablet, an enteric coated tablet, or a sustained release tablet. In some embodiments, the oral solid dosage form is in the form of an immediate release tablet.

In some embodiments, provided herein is a pharmaceutical composition that provides at least one metabolite of 2-(3-(2-((tert-butylthio)methyl)-4-(2,2-dimethyl-propionylamino)phenoxy)-4-methoxyphenyl)acetic acid (Compound 1) after administration to a mammal. In some embodiments, the at least one metabolite is selected from among:
  I. 2-(3-(2-(tert-butylsulfinylmethyl)-4-pivalamidophenoxy)-4-methoxyphenyl)acetic acid (M1);
  II. 2-(3-(2-(tert-butylsulfonylmethyl)-4-pivalamidophenoxy)-4-methoxyphenyl)acetic acid (M2);
  III. 2-(3-(2-(tert-butylthiomethyl)-4-pivalamidophenoxy)-4-hydroxyphenyl)acetic acid (M3);
  IV. Acyl-glucuronide of Compound 1 (M4);
  V. 2-(3-(2-(tert-butylsulfinylmethyl)-4-pivalamidophenoxy)-4-hydroxyphenyl)acetic acid (M4); and
  VI. combinations thereof.

Also provided is a method of treating or preventing a respiratory disease or condition, an inflammatory disease or condition or an allergic disease or condition, or combinations thereof, in a mammal comprising administering to the mammal an oral pharmaceutical composition as described herein.

In some embodiments, in any of the pharmaceutical compositions, methods or uses disclosed herein, crystalline Compound 1 is used. In some embodiments, in any of the pharmaceutical compositions, methods or uses disclosed herein, amorphous Compound 1 is used. In some embodiments, in any of the pharmaceutical compositions, methods or uses disclosed herein, a crystalline form of a pharmaceutically acceptable salt of Compound 1 is used. In some embodiments, in any of the pharmaceutical compositions, methods or uses disclosed herein, amorphous pharmaceutically acceptable salt of Compound 1 is used. In some embodiments, in any of the pharmaceutical compositions, methods or uses disclosed herein, crystalline Compound 2 is used. In some embodiments, in any of the pharmaceutical compositions, methods or uses disclosed herein, amorphous Compound 2 is used. In some embodiments, Compound 1 or a pharmaceutically acceptable salt thereof is solvated. In some embodiments, Compound 1 is solvated. In some embodiments, Compound 2 is solvated.

In some embodiments, the respiratory disease or condition, inflammatory disease or condition or allergic disease or condition is asthma, adult respiratory distress syndrome, isocapnic hyperventilation, rhinitis, chronic obstructive pulmonary disease, chronic bronchitis, emphysema, pulmonary hypertension, cystic fibrosis, an allergic ocular disease or condition, an inflammatory ocular disease or condition, an allergic skin disease or condition, or an inflammatory skin disease or condition.

In some embodiments, the respiratory disease or condition, inflammatory disease or condition or allergic disease or condition is asthma, rhinitis, dermatitis, ocular inflammation, or conjunctivitis.

Also provided is a method of treating or preventing asthma in a mammal comprising administering to the mammal an oral pharmaceutical composition as described herein. In some embodiments, the asthma is allergic asthma, non-allergic asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, neutrophilic asthma, occupational asthma, steroid-resistant asthma, or seasonal asthma.

Also provided is a method of treating rhinitis in a mammal comprising administering to the mammal an oral pharmaceutical composition as described herein. In some embodiments, the rhinitis is allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, or rhinopolyposis. In some embodiments, the rhinitis is allergic rhinitis.

Also provided is a method of treating chronic obstructive pulmonary disease (COPD) in a mammal comprising administering to the mammal an oral pharmaceutical composition as described herein.

In some embodiments, the mammal is a human.

In some embodiments, the method further comprises administering the mammal at least one additional pharmaceutical agent selected from inhaled corticosteroids, short acting beta-agonists, long acting beta-agonists, leukotriene modulators, and antihistamines.

In some embodiments, the pharmaceutical composition further comprises at least one additional pharmaceutical agent selected from inhaled corticosteroids, short acting beta-agonists, long acting beta-agonists, leukotriene modulators, and antihistamines.

Also provided is an article of manufacture comprising multiple unit doses of the oral solid dosage form pharmaceutical composition described herein in a high-density polyethylene (HDPE) bottle equipped with a high-density polyethylene (HDPE) cap.

In some embodiments, high-density polyethylene (HDPE) bottle further comprises an aluminum foil induction seal and silica gel desiccant.

Also provided is the use of Compound 1 or a pharmaceutically acceptable salt thereof (e.g. Compound 2) for the manufacture of a medicament for the treatment or prevention of a respiratory disease or condition in a human. In some embodiments, Compound 1 is used and is crystalline. In some embodiments, Compound 2 is used and is crystalline. In some embodiments, Compound 2 is used and is amorphous.

Also provided is the use of Compound 1 or a pharmaceutically acceptable salt thereof (e.g. Compound 2) for the manufacture of a medicament for the treatment of asthma in a human. In some embodiments, the asthma is persistent, uncontrolled asthma.

Also provided is the use of Compound 1 or a pharmaceutically acceptable salt thereof (e.g. Compound 2) for the manufacture of a medicament for the treatment or prevention of rhinitis in a human. In some embodiments, the rhinitis is allergic rhinitis.

Also provided is the use of Compound 1 or a pharmaceutically acceptable salt thereof (e.g. Compound 2) for the manufacture of a medicament for the treatment of chronic obstructive pulmonary disease in a human Also provided is the use of Compound 1 or a pharmaceutically acceptable salt thereof (e.g. Compound 2) for the manufacture of a medicament for the treatment of an ocular disease or condition in a human. In some embodiments, the ocular disease or condition is conjunctivitis.

Also provided is the use of Compound 1 or a pharmaceutically acceptable salt thereof (e.g. Compound 2) for the manufacture for the treatment of a skin disease or condition in a human. In some embodiments, the skin disease or condition is dermatitis.

Described in certain embodiments herein is an oral solid dosage form pharmaceutical composition comprising: (a) Compound 2; and (b) optionally at least one inactive pharmaceutical ingredient. In specific embodiments, the oral solid dosage form pharmaceutical composition is in the form of a capsule. In more specific embodiments, the capsule is a hard gelatine capsule or hypromellose (HPMC) capsule. In various embodiments, the capsules described herein comprise at least one excipient or no excipients.

In one aspect provided are methods for treating PGD$_2$-dependent or PGD$_2$-mediated diseases or conditions in a mammal, comprising administering to the mammal at least once an effective amount of Compound 1, or a pharmaceutically acceptable salt thereof (e.g. Compound 2).

In one aspect provided are methods for treating mammals with an inflammatory and/or allergic condition comprising administering to the mammal at least once an effective amount of Compound 1, or a pharmaceutically acceptable salt thereof (e.g. Compound 2).

In one aspect, provided herein is an oral pharmaceutical composition as described herein comprising Compound 1 or a pharmaceutically acceptable salt thereof as the active ingredient for use in the treatment or prevention of an inflammatory and/or allergic condition in a mammal. In some embodiments, the active ingredient is Compound 1. In other embodiments, the active ingredient is Compound 2.

In one aspect are methods for treating inflammation in a mammal comprising administering to the mammal at least once an effective amount of Compound 1, or a pharmaceutically acceptable salt thereof (e.g. Compound 2).

In one aspect are methods for treating respiratory diseases in a mammal comprising administering to the mammal at least once an effective amount of Compound 1, or a pharmaceutically acceptable salt thereof (e.g. Compound 2). Respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vasomotor rhinitis, vascular responses, endotoxin shock, fibrogenesis, pulmonary fibrosis, allergic diseases, chronic inflammation, and adult respiratory distress syndrome. In a specific embodiment of this aspect, the respiratory disease is asthma.

In one aspect are methods for treating or preventing rhinitis in a mammal comprising administering to the mammal at least once an effective amount of Compound 1, or a pharmaceutically acceptable salt thereof (e.g. Compound 2). Rhinitis includes: allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In one aspect are methods for treating chronic obstructive pulmonary disease in a mammal comprising administering to the mammal at least once an effective amount of Compound 1, or a pharmaceutically acceptable salt thereof (e.g. Compound 2). Chronic obstructive pulmonary disease includes, but is not limited to, chronic bronchitis or emphysema, pulmonary hypertension, interstitial lung fibrosis and/or airway inflammation and cystic fibrosis.

In one aspect are methods for preventing increased mucosal secretion and/or edema in a mammal comprising administering to the mammal at least once an effective amount of Compound 1, or a pharmaceutically acceptable salt thereof (e.g. Compound 2).

In one aspect are methods for preventing eosinophil and/or basophil and/or dendritic cell and/or neutrophil and/or monocyte recruitment in a mammal comprising administering to the mammal at least once an effective amount of Compound 1, or a pharmaceutically acceptable salt thereof (e.g. Compound 2).

In another aspect are methods for preventing ocular disease (for example, ocular inflammation, allergic conjunctivitis, vernal keratoconjunctivitis and papillary conjunctivitis) in a mammal comprising administering to the mammal at least once an effective amount of Compound 1, or a pharmaceutically acceptable salt thereof (e.g. Compound 2).

In another aspect are methods for preventing or treating acute or chronic disorders involving recruitment or activation of eosinophils in a mammal comprising administering to the mammal at least once an effective amount of Compound 1, or a pharmaceutically acceptable salt thereof (e.g. Compound 2).

In any of the aforementioned aspects, the mammal is a human. In any of the aforementioned aspects, the mammal is a human, including embodiments wherein (a) the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, occupational asthma, steroid-resistant asthma, seasonal asthma, allergic rhinitis, non-allergic rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, rhinopolyposis, and chronic obstructive pulmonary disease.

In any of the aforementioned aspects are further embodiments comprising single administrations of the effective amount of Compound 1, or a pharmaceutically acceptable salt thereof (e.g. Compound 2), including further embodiments in which Compound 1, or a pharmaceutically acceptable salt thereof (e.g. Compound 2) is (i) administered once-a-day; (ii) is administered twice-a-day; or (iii) is administered multiple times over the span of one day.

In any of the aforementioned aspects are further embodiments comprising multiple administrations of the effective amount of the compound, including further embodiments in which (i) the compound is administered in a single dose; (ii) the time between multiple administrations is every 6 hours; (iii) the time between multiple administrations is every 8 hours; (iv) the time between multiple administrations is every 12 hours.

In some embodiments, the pharmaceutical composition is administered daily to the mammal.

In some embodiments, the pharmaceutical composition is administered in treatment cycles comprising: (a) a first period during which Compound 2 is administered daily to the mammal; and (b) a second period of at least seven days during which the Compound 1, or a pharmaceutically acceptable salt thereof (e.g. Compound 2) is administered to the mammal in a reduced amount as compared to (a).

In some embodiments, the methods of treatment or prevention disclosed herein comprise a drug holiday, wherein the administration of Compound 1, or a pharmaceutically acceptable salt thereof (e.g. Compound 2) is temporarily suspended or the dose being administered is temporarily reduced; at the end of the drug holiday dosing is resumed. In some embodiments, the length of the drug holiday varies from 2 days to 1 year.

In one aspect, Compound 1, or a pharmaceutically acceptable salt thereof (e.g. Compound 2) is used in the manufacture of medicaments for the treatment of a $PGD_2$-dependent or $PGD_2$-mediated respiratory disease or condition in a mammal whose symptoms of the respiratory disease or condition are not adequately controlled by corticosteroids. In a specific embodiment, the respiratory disease or condition is asthma.

Compound 1, or a pharmaceutically acceptable salt thereof (e.g. Compound 2) for treating any of the diseases or conditions disclosed herein. In some embodiments, Compound 1 is crystalline. In some embodiments, Compound 2 is crystalline. In some embodiments, Compound 2 is amorphous.

A pharmaceutical composition comprising Compound 1, or a pharmaceutically acceptable salt thereof (e.g. Compound 2) for use in any of the uses and methods disclosed herein.

Use of Compound 1, or a pharmaceutically acceptable salt thereof (e.g. Compound 2) in the manufacture of a medicament for treating or preventing any of the diseases disclosed herein in a mammal. In one aspect, Compound 1 or a pharmaceutically acceptable salt thereof (e.g. Compound 2) is used in the treatment of a respiratory disease or condition in a mammal.

In one aspect is the use of Compound 1 or a pharmaceutically acceptable salt thereof (e.g. Compound 2) for the manufacture of a medicament for the treatment of asthma in a human. In one aspect is the use of Compound 1 or a pharmaceutically acceptable salt thereof (e.g. Compound 2) for the manufacture of a medicament for the treatment or prevention of allergic rhinitis in a human. In one aspect is the use of Compound 1 or a pharmaceutically acceptable salt thereof (e.g. Compound 2) for the manufacture of a medicament for the treatment of chronic obstructive pulmonary disease in a human. In one aspect is the use of Compound 1 or a pharmaceutically acceptable salt thereof (e.g. Compound 2) for the manufacture of a medicament for the treatment of ocular disease in a human. In one aspect is the use of Compound 1 or a pharmaceutically acceptable salt thereof (e.g. Compound 2) for the manufacture of a medicament for the treatment of skin disease in a human.

In one aspect, described herein is a method of increasing the bioavailability of an orally administered dose of Compound 1, or a pharmaceutically acceptable salt thereof (e.g. Compound 2) in healthy human patients comprising orally administering to a mammal: (1) a dose of Compound 1, or a pharmaceutically acceptable salt thereof (e.g. Compound 2); and (2) an inhibitor of a UDP-glucuronosyltransferase enzyme normally present in the mammal.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal; and/or (e) measuring inhibition of $PGD_2$-induced eosinophil shape change (ESC) in a mammal; and/or (f) measuring Th2 cytokine levels in a mammal.

Also described herein are process for the preparation of Compound 1 and pharmaceutically acceptable salts thereof. In one aspect, the pharmaceutically acceptable salt of Compound 1 is the sodium salt (Compound 2).

In one aspect, described is a process for the preparation of crystalline Compound 2 comprising the steps of:
(1) dissolving Compound 2 in acetone;
(2) adding heptane to the acetone solution of Compound 2; and
(3) isolating the solids that are formed from step (2) to provide crystalline Compound 2.

The disclosed processes provide for the synthesis of Compound 1 and pharmaceutically acceptable salts thereof (e.g. Compound 2). The processes disclosed herein are particularly applicable to large scale chemical production of Compound 1 and pharmaceutically acceptable salts thereof. Also described herein are processes for the preparation of Compound 2, in good yield that have good solubility and good oral bioavailability.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

DETAILED DESCRIPTION OF THE INVENTION

Figure 1:
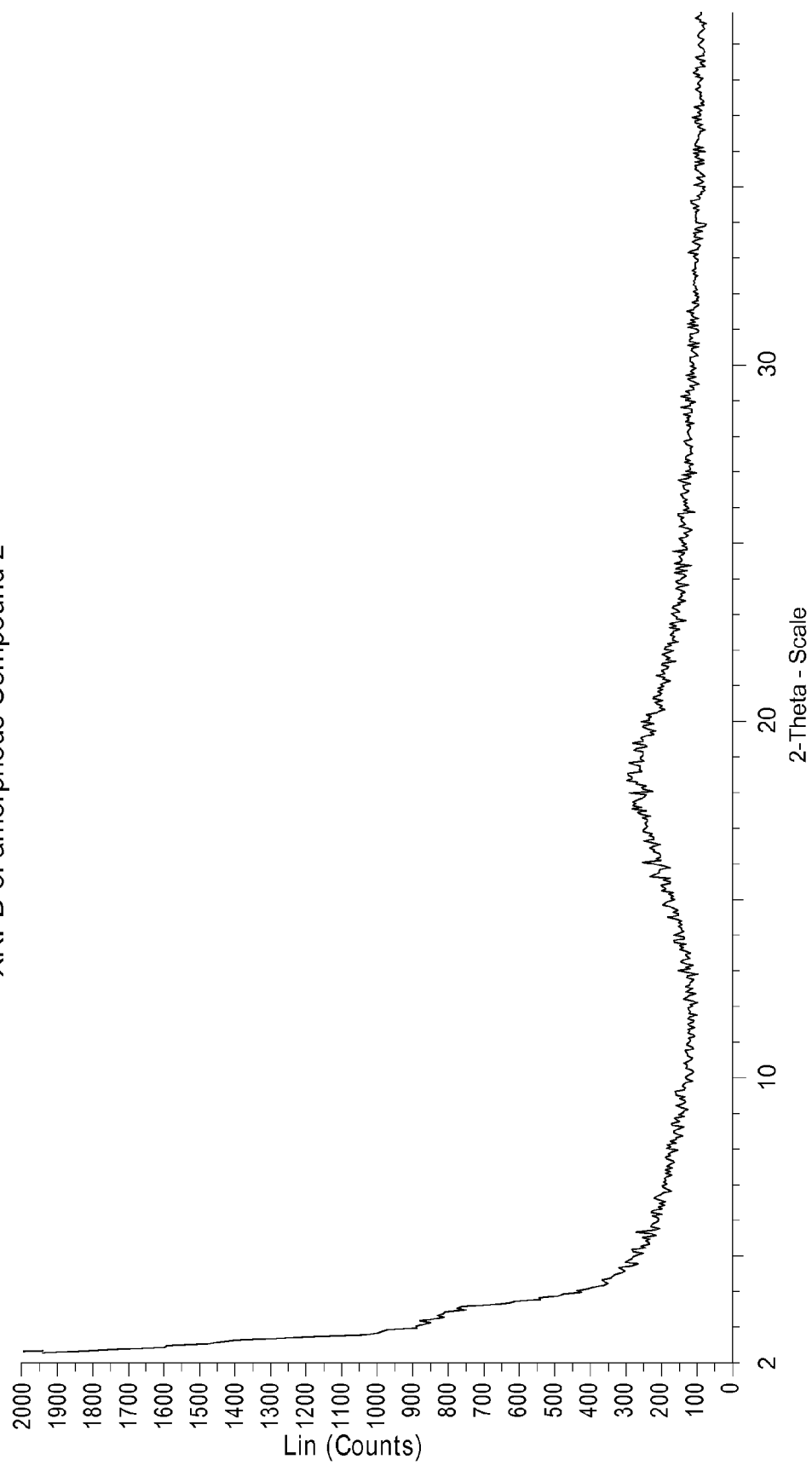
FIG. 1 illustrates the XRPD of amorphous Compound 2.

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and Th2 lymphocytes in response to local tissue damage as well as in response allergic inflammation observed in diseases such as asthma, rhinitis, and atopic dermatitis. More specifically, exogenous $PGD_2$ applied to bronchial airways elicits many responses that are characteristic of acute asthma.

$PGD_2$ is a major mast cell product that acts via two receptors, the D-type prostanoid (DP, also known as $DP_1$) and the chemoattractant receptor-homologous molecule expressed on Th2 cells (CRTH2, also known as $DP_2$) receptors. $DP_2$ mediates the chemotaxis of eosinophils, basophils, and Th2 lymphocytes, and $DP_1$ receptor plays an important role in eosinophil trafficking. $DP_1$ antagonists do not inhibit the release of eosinophils when induced by the $DP_2$-selective agonists. However, eosinophils in human bone marrow specimens express $DP_1$ and $DP_2$ receptors at similar levels and human peripheral blood expresses both $DP_1$ and $DP_2$, but the $DP_1$ receptor is expressed at lower levels. In agreement with this, the chemotaxis of human peripheral blood eosinophils is inhibited by both $DP_1$ and $DP_2$ antagonists. Accordingly, $DP_1$, $DP_2$ and dual $DP_1/DP_2$ antagonists are useful in the treatment of allergic inflammation.

Activation of $DP_2$ is associated with chemotaxis and activation of Th2 lymphocytes, eosinophils and basophils. In particular, $PGD_2$ binds to $DP_2$ and mediates many of its effects through a $G_i$-dependent elevation of intracellular calcium levels and reduction of cyclic AMP. In Th2 lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

The terms CRTH2 and $DP_2$, refer to the same receptor and are used interchangeably herein. Likewise, another common name for DP is $DP_1$, and the two terms are used interchangeably herein. $DP_2$ and $DP_2$ receptor are used interchangeably.

In asthma and other allergic inflammatory conditions, mast cells produce $PGD_2$, an inflammatory mediator in the prostaglandin pathway which mediates a number of signs of asthma. The $DP_2$ receptor mediates pro-inflammatory responses of $PGD_2$ that are important in asthma including the activation and chemotaxis of eosinophils, basophils, Th2 cells, and the release of Th2 cytokines such as IL-4, IL-5, and IL-13.

In patients with cystic fibrosis, the $DP_2$ receptor is expressed on sputum neutrophils and not on circulating neutrophils (Tirouvanziam, R., et al., 2008. *Proc. Nat. Acad. Sci. USA* 105:4335-4339), which indicate a role for $DP_2$ in neutrophil-mediated airway inflammation such as observed in severe, non-allergic asthma, corticosteroid-resistant asthma, and chronic obstructive pulmonary disease (COPD).

Blocking the $PGD_2$-mediated activation of the $DP_2$ receptor has not been associated with any specific safety concerns in preclinical studies using $DP_2$ antagonists. Knock-out mice are healthy and fertile, and multiple studies have shown the $DP_2$ deficient mice to be protected from allergic inflammatory responses (Pettipher, R., et al., 2007. *Nature Drug Discovery* 6: 313-325).

Although there are a number of selective $DP_2$ antagonists in clinical trials for asthma, allergic rhinitis, and COPD, there is no marketed selective $DP_2$ antagonist.

A number of selective $DP_2$ antagonists are in Phase 2 clinical trials for asthma, allergic rhinitis, and COPD. Some of these selective $DP_2$ antagonists have been reported to inhibit in vitro $PGD_2$ responses as well as allergic responses in animal models of asthma and allergic rhinitis. Treatment for 8 days with a $DP_2$ antagonist was shown to improve nasal symptom scores in allergic rhinitis patients following nasal allergen challenge (Patent Applications WO2009/063202 and WO2009/063215). In this study, a protective effect on nasal symptom scores was reported to last up to 4 weeks post treatment. It was proposed that the $DP_2$ antagonist caused desensitization of the allergic response through the inhibition of the $DP_2$-mediated anti-apoptotic effect of $PGD_2$ on Th2 cells.

Compound 1 is a selective, orally bioavailable, small molecule DP2 antagonist. Compound 1 binds to $DP_2$ with high affinity ($IC_{50}$=19.7 nM in the presence of 0.5% serum albumin), and is a full antagonist. Compound 1 inhibits the functional activity of $DP_2$ as measured by inhibition of $PGD_2$-induced eosinophil shape change (ESC) in human whole blood ($IC_{50}$=1.5 nM).

Compound 1 has been shown to be active in preclinical pharmacology models of allergic rhinitis, asthma, COPD, and DK-$PGD_2$-stimulated leukocyte recruitment. In one embodiment, the data support a once a day oral administration. In another embodiment, the data support twice-a-day oral administration.

Diseases or Conditions

Compound 1, or a pharmaceutically salt thereof (e.g. Compound 2), is used in the treatment or prevention of $PGD_2$-dependent or $PGD_2$-mediated diseases or conditions in mammals. The term "$PGD_2$-dependent", as used herein, refers to conditions or disorders that would not occur, or would not occur to the same extent, in the absence of $PGD_2$. The term "$PGD_2$-mediated", as used herein, refers to refers to conditions or disorders that might occur in the absence of $PGD_2$ but can occur in the presence of $PGD_2$.

In one aspect, $PGD_2$-dependent or $PGD_2$-mediated diseases or conditions include, but are not limited to, asthma, rhinitis, allergic conjunctivitis, atopic dermatitis, chronic obstructive pulmonary disease (COPD), pulmonary hypertension, interstitial lung fibrosis, cystic fibrosis, arthritis, allergy, psoriasis, inflammatory bowel disease, adult respiratory distress syndrome, myocardial infarction, stroke, arthritis, wound healing, endotoxic shock, cancer, pain, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, uveitis, angioedema, anaphylaxia, chronic cough and Churg Strauss syndrome.

In some embodiments, Compound 1, or a pharmaceutically salt thereof (e.g. Compound 2), is used in the treatment of respiratory disease or conditions, allergic diseases or conditions, and/or inflammatory diseases or conditions in a mammal. In some embodiments, Compound 2 is used in the treatment of respiratory disease or conditions, allergic diseases or conditions, and/or inflammatory diseases or conditions in a mammal. In some embodiments, Compound 2 is crystalline.

In some embodiments, Compound 1, or a pharmaceutically salt thereof (e.g. Compound 2), is used in the treatment of respiratory diseases or conditions in a mammal. In some embodiments, Compound 2 is used in the treatment of respiratory diseases or conditions in a mammal. In some embodiments, Compound 2 is used in the treatment of asthmas in a human. In some embodiments, Compound 2 is crystalline.

The term "respiratory disease," as used herein, refers to diseases affecting the organs that are involved in breathing, such as the nose, throat, larynx, eustachian tubes, trachea, bronchi, lungs, related muscles (e.g., diaphragm and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, neutrophilic asthma, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In some embodiments, respiratory disease or condition is asthma. The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause. In some embodiments, the type of asthma is allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, child-onset asthma, adult-onset asthma, cough-variant asthma, neutrophilic asthma, occupational asthma, steroid-resistant asthma, or seasonal asthma.

Asthma is a chronic inflammatory disorder of the airways in which many cells and cellular elements play a role. The chronic inflammation associated with airway hyperresponsiveness leads to recurrent episodes of wheezing, breathlessness, chest tightness, and coughing, particularly at night or in the early morning. These episodes are usually associated with widespread, but variable, airflow obstruction that is often reversible either spontaneously, or with treatment.

There are still significant medical needs in persistent, mild, moderate, and severe asthma. The control of asthma is not always achieved despite the step-wise approach to treatment. In the long-term, pulmonary function can be modified with the development of non-reversible obstruction. The evolution of the disease can be unpredictable, precipitating admission to the emergency room. The patients who are uncontrolled on inhaled or oral corticosteroids exhibit many of the following signs: symptoms at least twice weekly, limitations on activity, frequent nocturnal symptoms and awakenings, frequent use of a rescue inhaler, exacerbations up to once in a week, and reduced lung function (FEV1<80% predicted). There is a need for novel, oral controller medicine to provide new treatment options for patients with uncontrolled asthma.

Because of the mechanism of action of Compound 1 on allergic inflammation, Compound 1 is a therapeutic option for patients with allergic asthma who are not adequately controlled with current therapies. In some embodiments, a treatment effect is obtained in non-allergic asthma.

In one embodiments, Compound 1, or a pharmaceutically salt thereof (e.g. Compound 2), is used in the chronic treatment of persistent, uncontrolled asthma. Persistent, uncontrolled asthma is characterized as asthma that is not adequately controlled with current therapies (e.g. steroid resistant asthma).

In some embodiments, Compound 1, or a pharmaceutically salt thereof (e.g. Compound 2), is used in the treatment of allergic diseases or conditions in a mammal. In some embodiments, Compound 2 is used in the treatment of allergic diseases or conditions in a mammal. In some embodiments, Compound 2 is crystalline.

Allergic diseases or conditions include, but are not limited to, ocular inflammation and conjunctivitis, vernal keratoconjunctivitis, papillary conjunctivitis, rhinitis, asthma, dermatitis.

In some embodiments, Compound 1, or a pharmaceutically salt thereof (e.g. Compound 2), is used in the treatment of ocular diseases or conditions. The term "ocular disease or condition" as used herein, refers to diseases or conditions which affect the eye or eyes and potentially the surrounding tissues as well. Ocular disease or condition includes, but is not limited to, ocular inflammation, conjunctivitis, retinitis, scleritis, uveitis, allergic conjunctivitis, vernal conjunctivitis, papillary conjunctivitis, uveoretinitis.

In one aspect, the allergic disease or condition is rhinitis. The term "rhinitis" as used herein refers to any disorder of the nose in which there is inflammation of the mucous lining of the nose by whatever cause (intrinsic, extrinsic or both; allergic or non-allergic). In some embodiments, the rhinitis includes, but is not limited to, allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In one embodiment, Compound 1, or a pharmaceutically salt thereof (e.g. Compound 2), is used in the treatment of allergic rhinitis in a mammal. In one embodiment, Compound 2 is used in the treatment of allergic rhinitis in a mammal.

In one embodiment, Compound 1, or a pharmaceutically salt thereof (e.g. Compound 2), is used in the treatment of type I hypersensitivity in a mammal. Type I hypersensitivity is an allergic reaction provoked by exposure to an allergen. Exposure may be by ingestion, inhalation, injection, or direct contact. Non-limiting examples of type I hypersensitivity include allergic asthma, allergic conjunctivitis, allergic rhinitis, anaphylaxis, angioedema, allergic dermatitis, urticaria, eosinophilia, penicillin allergy, cephalosporin allergy, food allergy.

In one embodiment, Compound 1, or a pharmaceutically salt thereof (e.g. Compound 2), is used in the treatment of skin disease in a mammal. In one embodiment, Compound 2 is used in the treatment of skin disease in a mammal. Skin disease includes but is not limited to eczema, psoriasis, pruritis, uticaria, pemphigus, allergic dermatitis, atopic dermatitis, neurodermatitis, exfoliative dermatitis, irritant dermatitis, seborrheic dermatitis, thermal induced dermatitis, drug induced dermatitis, atopic eczema, seborrhoeic dermatitis, dyshidrotic dermatitis (also known as Pompholyx), papular urticaria (a pattern of dermatitis often presenting after insect bite reactions), and hypersensitivity reactions Allergic dermatitis is typically a result of contact with external compounds, preservatives, fragrances, or plants.

In some embodiments, Compound 1, or a pharmaceutically salt thereof (e.g. Compound 2), is used in the treatment of chronic obstructive pulmonary disease in a mammal. In some embodiments, Compound 2 is used in the treatment of chronic obstructive pulmonary disease in a mammal.

Chronic obstructive pulmonary disease includes, but is not limited to, chronic bronchitis and/or emphysema, pulmonary hypertension, interstitial lung fibrosis and/or airway inflammation and cystic fibrosis.

In one aspect, Compound 1, or a pharmaceutically acceptable salt thereof is used in the treatment of neutrophilic inflammation in a mammal. In one aspect, Compound 2 is used in the treatment of neutrophilic inflammation in a mammal. Neutrophilic inflammation is involved in many inflammatory diseases or conditions. Neutrophilic inflammation is involved in many inflammatory diseases or conditions, such as respiratory diseases or conditions or allergic diseases or conditions.

In one aspect, assays described herein diagnose individuals as suitable candidates for therapy with $DP_2$ antagonist compounds. In one aspect, the individuals include those individuals with an inflammatory disease or condition. In one aspect, the inflammatory disease or condition is a respiratory disease or condition. In another aspect, the inflammatory disease or condition is an allergic disease or condition.

In some embodiments, Compound 1, or a pharmaceutically salt thereof (e.g. Compound 2), is used in the treatment of an inflammatory disease or condition in a mammal. In some embodiments, Compound 2 is used in the treatment of an inflammatory disease or condition in a mammal. "Inflammatory disease or condition" refers to those diseases or conditions that are characterized by one or more of the signs of pain, heat, redness, swelling, and loss of function (temporary or permanent). In one aspect, the inflammatory disease or condition is triggered by $PGD_2$.

Inflammation takes many forms and includes, but is not limited to, inflammation that is characterized by one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative.

Inflammatory diseases or conditions include those affecting the blood vessels (polyarteritis, temporal arteritis); joints (arthritis: crystalline, osteo-, psoriatic, reactive, rheumatoid, Reiter's); gastrointestinal tract (colitis); skin (dermatitis); organs (lungs, liver, pancreas); or multiple organs and tissues (systemic lupus erythematosus).

Inflammatory diseases or conditions include, but are not limited to, respiratory diseases or conditions, allergic diseases or conditions, psoriasis, inflammatory bowel disease, adult respiratory distress syndrome, myocardial infarction, congestive heart failure, stroke, arthritis, wound healing, endotoxic shock, cancer, pain, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, uveitis, angioedema, anaphylaxia, chronic cough, Churg Strauss syndrome, rheumatoid arthritis, ankylosing spondylitis, osteoarthritis, lupus, graft versus host disease, tissue transplant rejection, ischemic conditions, epilepsy, Alzheimer's disease, Parkinson's disease, vitiligo, Wegener's granulomatosis, gout, eczema, dermatitis, coronary infarct damage, chronic inflammation, smooth muscle proliferation disorders, multiple sclerosis, and acute leukocyte-mediated lung injury. In some embodiments, inflammatory conditions are immune or anaphylactic disorders associated with infiltration of leukocytes into inflamed tissues or organs. In other embodiments, inflammatory conditions are associated with T-lymphocyte activation.

In some embodiments, Compound 1, or a pharmaceutically salt thereof (e.g. Compound 2), is used to desensitize the immune system of a mammal to one or more allergens responsible for an allergic disease or condition. In some embodiments, Compound 2 is used to desensitize the immune system of a mammal to one or more allergens responsible for an allergic disease or condition. Desensitizing the immune system to one or more allergens refers to the reduction in the atopic state of the patient. A reduction in the atopic state of the patient is achieved by, e.g. a reduction in the levels of cells reactive to allergen the body of the mammal.

In some embodiments, described herein is a method for preventing and/or treating eosinophil and/or basophil and/or dendritic cell and/or neutrophil and/or monocyte recruitment in comprising administering at least once to the mammal an effective amount of Compound 1, or a pharmaceutically acceptable salt thereof (e.g. Compound 2).

Described herein are compositions, pharmaceutical compositions, methods for treating, methods for formulating, methods for producing, methods for manufacturing, treatment strategies, pharmacokinetic strategies using Compound 1, or pharmaceutically acceptable salts thereof.

Compound 1, and Pharmaceutically Acceptable Salts Thereof

"Compound 1" or "2-(3-(2-((tert-butylthio)methyl)-4-(2,2-dimethyl-propionylamino)phenoxy)-4-methoxyphenyl) acetic acid" or "2-(3-(2-(tert-butylthiomethyl)-4-pivalamidophenoxy)-4-methoxyphenyl)acetic acid" refers to the compound with the following structure:

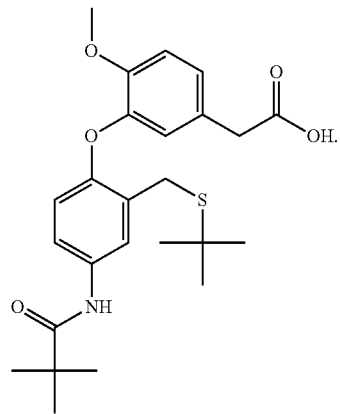 [SMILES: COc1ccc(CC(=O)O)cc1Oc1ccc(NC(=O)C(C)(C)C)cc1CSC(C)(C)C]

"Compound 2" or 2-(3-(2-((tert-butylthio)methyl)-4-(2,2-dimethyl-propionylamino)phenoxy)-4-methoxyphenyl)acetic acid, sodium salt" or "sodium 2-(3-(2-((tert-butylthio)methyl)-4-(2,2-dimethyl-propionylamino)phenoxy)-4-methoxyphenyl)acetate" or "2-(3-(2-(tert-butylthiomethyl)-4-pivalamidophenoxy)-4-methoxyphenyl)acetic acid sodium salt" refers to the compound with the following structure:

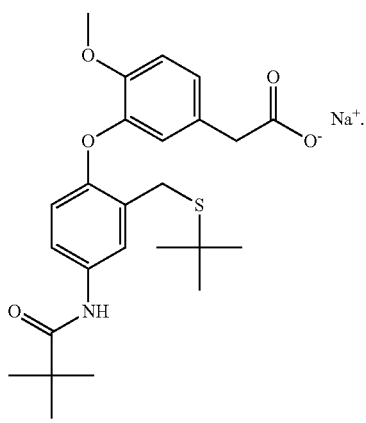

A wide variety of pharmaceutically acceptable salts are formed from Compound 1 and include:
- salts formed when the acidic proton of the carboxylic acid of Compound 1 is replaced by a metal ion, such as for example, an alkali metal ion (e.g. lithium, sodium, potassium), an alkaline earth ion (e.g. magnesium, or calcium), or an aluminum ion, or is replaced by an ammonium cation ($NH_4^+$);
- salts formed by reacting Compound 1 with a pharmaceutically acceptable organic base, which includes alkylamines, such as choline, ethanolamine, diethanolamine, triethanolamine, tromethamine, N-methylglucamine, dicyclohexylamine, tris(hydroxymethyl)methylamine, and salts with amino acids, such as arginine, lysine, and the like.

In some embodiments, Compound 1 is treated with an amino acid to form a salt.

In other embodiments, Compound 1 is treated with choline, ethanolamine, diethanolamine, triethanolamine, tromethamine, N-methylglucamine, arginine, lysine, ammonium hydroide, calcium hydroxide, potassium hydroxide, sodium carbonate, sodium hydroxide, and the like to form a salt.

The term "pharmaceutically acceptable salt" in reference to Compound 1 refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methyl tert-butyl ether, isopropanol, acetonitrile, heptane, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In one embodiment, solvates of Compound 1, or salts thereof, are conveniently prepared or formed during the processes described herein. In addition, Compound 1, or salts thereof, exist in unsolvated form.

In yet other embodiments, Compound 1, or a pharmaceutically acceptable salt thereof (e.g. Compound 2) is prepared in various forms, including but not limited to, amorphous phase, milled forms and nano-particulate forms.

Amorphous Compound 1

In some embodiments, Compound 1 is amorphous. In some embodiments, Amorphous Phase of Compound 1 has an XRPD pattern showing a lack of crystallinity.

Compound 1—Pattern 1

Figure 4:
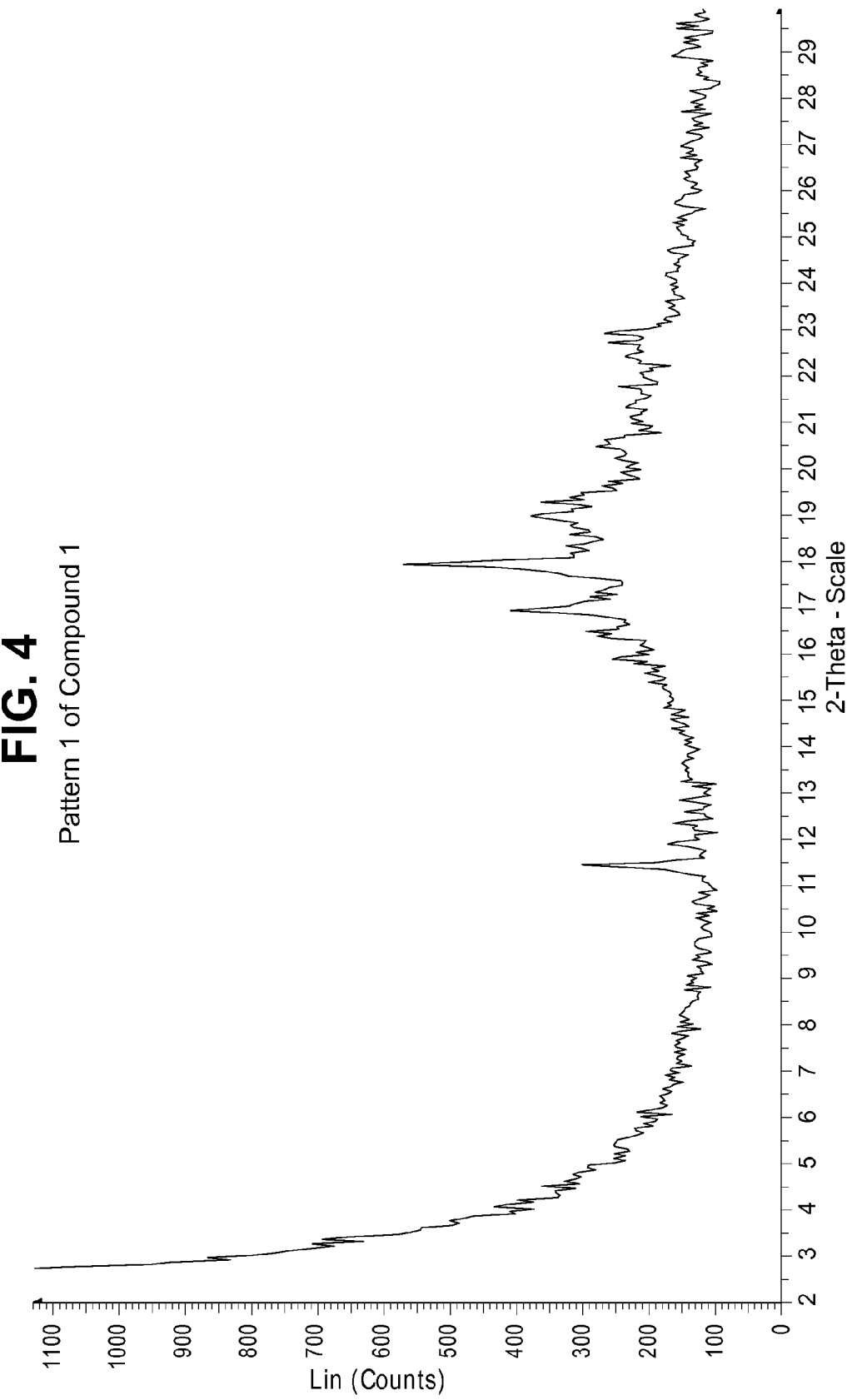
FIG. 4 illustrates the XRPD of Pattern 1 of Compound 1.

In some embodiments, Compound 1 is crystalline. In some embodiments, Compound 1 is crystalline Pattern 1. Crystalline Pattern 1 of Compound 1 is characterized as having at least one of the following properties:
(a) an X-ray powder diffraction (XRPD) pattern with characteristic peaks at 11.4° 2-Theta, 16.9° 2-Theta, 17.9° 2-Theta, and 18.9° 2-Theta;
(b) an X-ray powder diffraction (XRPD) pattern substantially the same as shown in FIG. 4;
(c) a DSC thermogram with endotherms at about 32° C., about 77° C., and about 136° C.

In some embodiments, Crystalline Pattern 1 of Compound 1 is characterized as having at least two of the properties selected from (a) to (c). In some embodiments, Crystalline Pattern 1 of Compound 1 is characterized as having properties (a), (b), and (c).

Compound 1—Pattern 2

Figure 5:
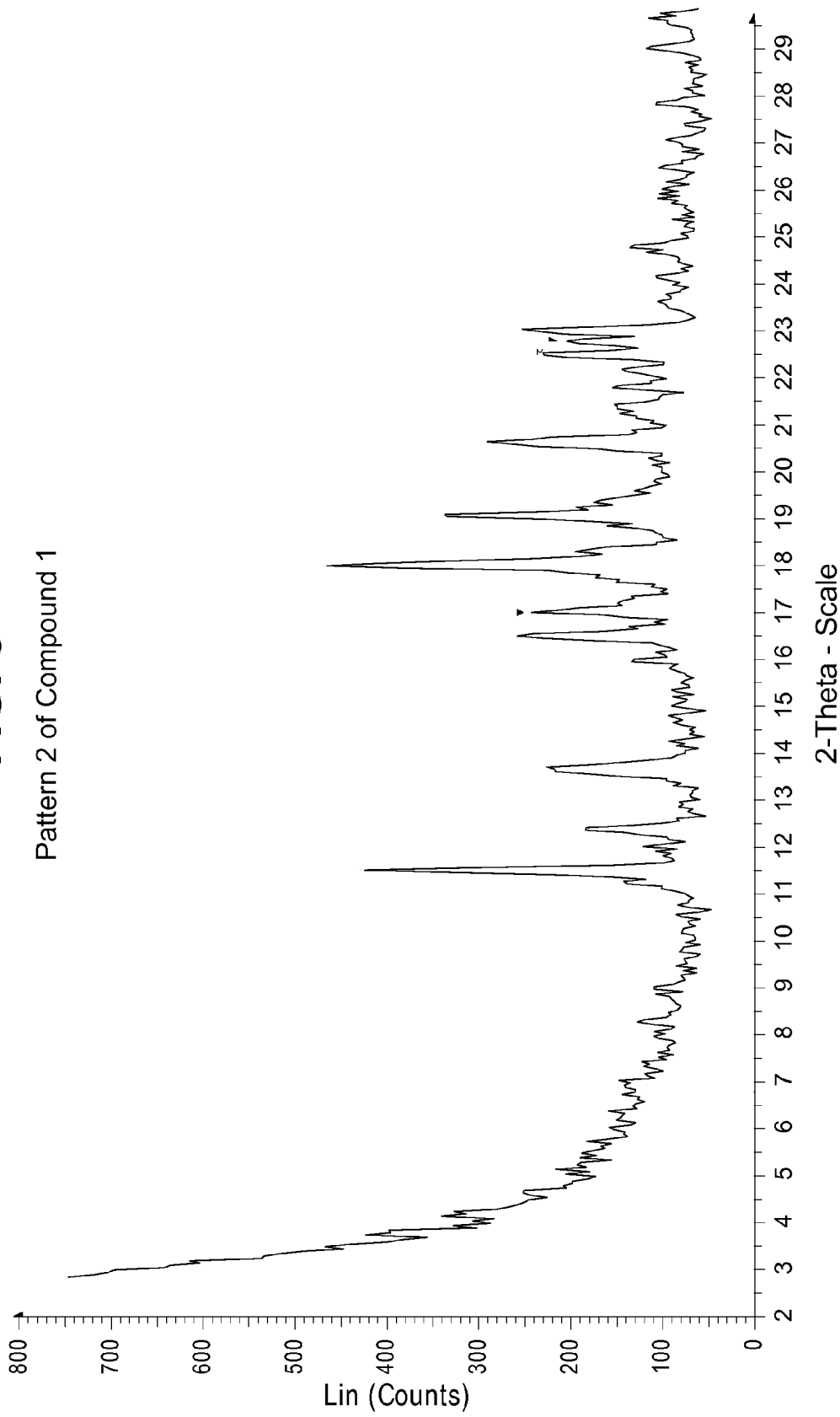
FIG. 5 illustrates the XRPD of Pattern 2 of Compound 1.

In some embodiments, Compound 1 is crystalline. In some embodiments, Compound 1 is crystalline Pattern 2. Crystalline Pattern 2 of Compound 1 is characterized as having at least one of the following properties:
(a) an X-ray powder diffraction (XRPD) pattern with characteristic peaks at 11.5° 2-Theta, 17.9° 2-Theta, 19.0° 2-Theta, and 20.6° 2-Theta.
(b) an X-ray powder diffraction (XRPD) pattern with characteristic peaks at 11.5° 2-Theta, 17.9° 2-Theta, 19.0° 2-Theta, and 20.6° 2-Theta and at least one additional characteristic peak selected from 12.3° 2-Theta, 13.6° 2-Theta, 16.5° 2-Theta, 16.9° 2-Theta, 22.5° 2-Theta, 22.7° 2-Theta, and 23.0° 2-Theta.
(c) an X-ray powder diffraction (XRPD) pattern substantially the same as shown in FIG. 5.
(d) a DSC thermogram with endotherms at about 52° C. and about 139° C.

In some embodiments, Crystalline Pattern 2 of Compound 1 is characterized as having at least two of the properties selected from (a) to (d). In some embodiments, Crystalline Pattern 2 of Compound 1 is characterized as having at least three of the properties selected from (a) to (d). In some embodiments, Crystalline Pattern 2 of Compound 1 is characterized as having properties (a), (b), (c), and (d).

Compound 1—Pattern 3

Figure 6:
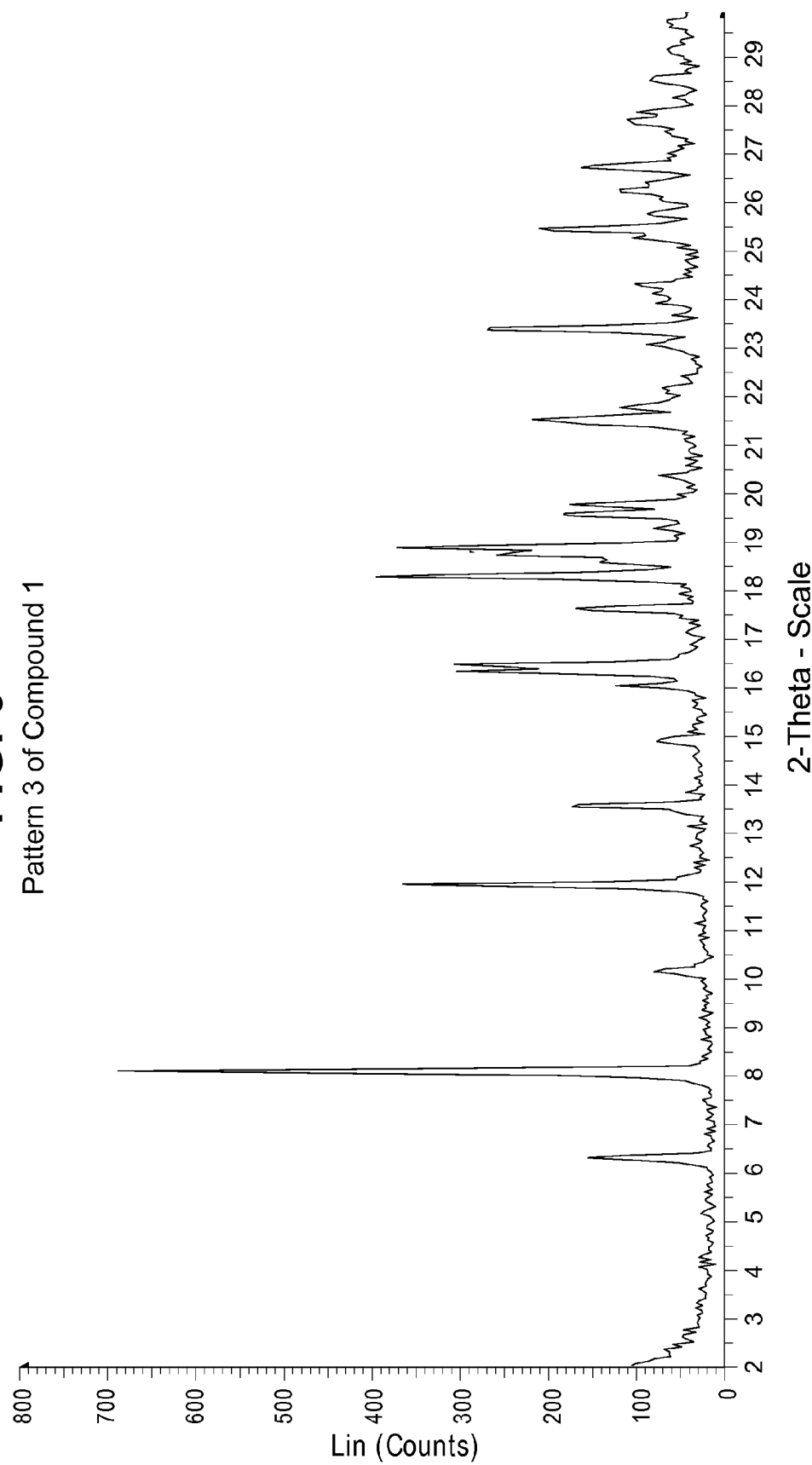
FIG. 6 illustrates the XRPD of Pattern 3 of Compound 1.

In some embodiments, Compound 1 is crystalline. In some embodiments, Compound 1 is crystalline Pattern 3. Crystalline Pattern 3 of Compound 1 is characterized as having at least one of the following properties:
(a) an X-ray powder diffraction (XRPD) pattern with characteristic peaks at 8.1° 2-Theta, 11.9° 2-Theta, 18.2° 2-Theta, and 18.9° 2-Theta.
(b) an X-ray powder diffraction (XRPD) pattern with characteristic peaks at 8.1° 2-Theta, 11.9° 2-Theta, 18.2° 2-Theta, and 18.9° 2-Theta and at least one additional characteristic peak selected from 6.3° 2-Theta, 13.5° 2-Theta, 16.3° 2-Theta, 16.5° 2-Theta, 18.7° 2-Theta, 19.5° 2-Theta, 21.5° 2-Theta, and 23.4° 2-Theta.
(c) an X-ray powder diffraction (XRPD) pattern substantially the same as shown in FIG. 6.
(d) a DSC thermogram with endotherms at about 38° C. and about 147° C.

In some embodiments, Crystalline Pattern 3 of Compound 1 is characterized as having at least two of the properties selected from (a) to (d). In some embodiments, Crystalline Pattern 3 of Compound 2 is characterized as having at least three of the properties selected from (a) to (d). In some embodiments, Crystalline Pattern 3 of Compound 1 is characterized as having properties (a), (b), (c), and (d).

Compound 1—Pattern 4

Figure 7:
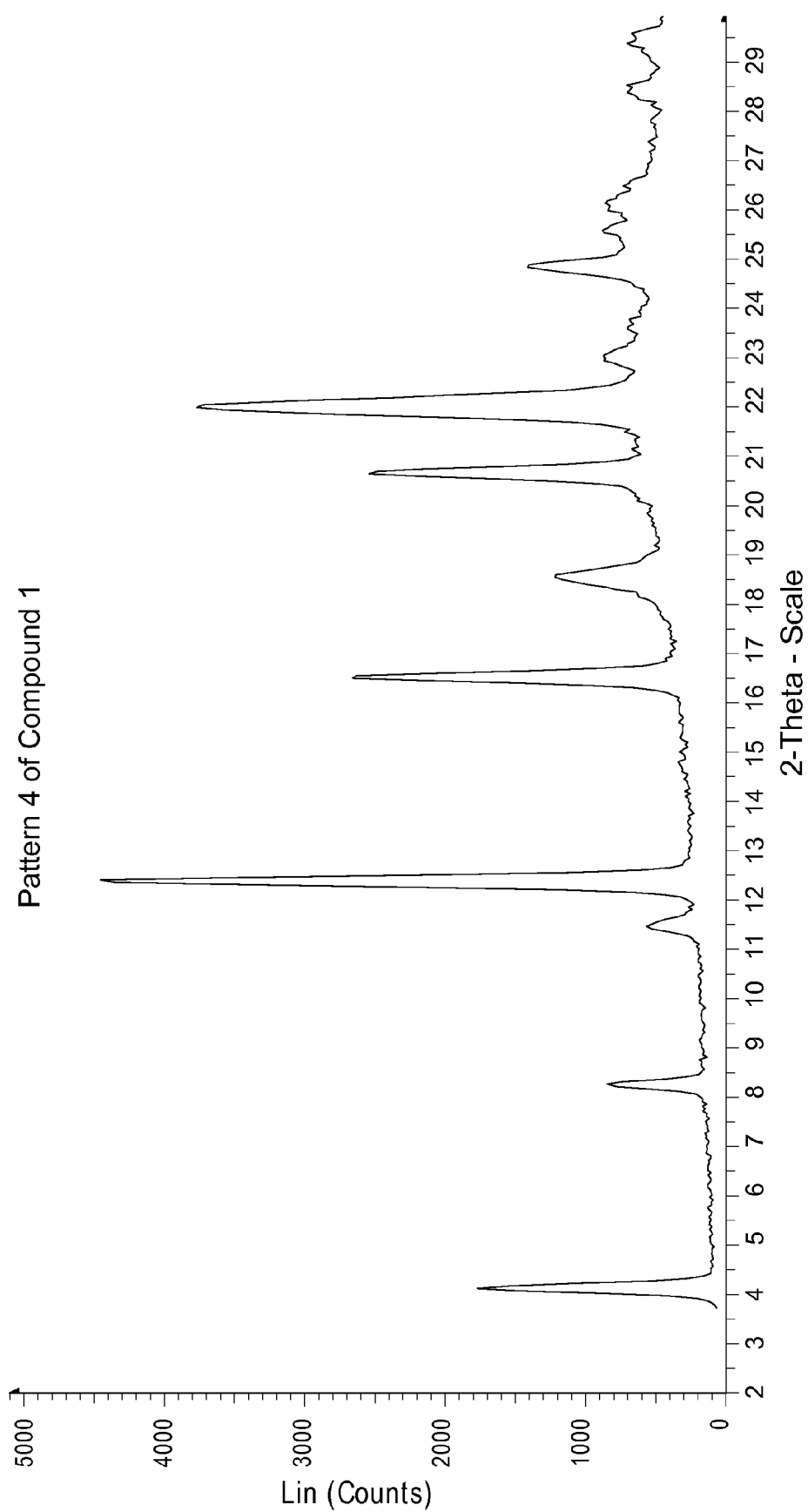
FIG. 7 illustrates the XRPD of Pattern 4 of Compound 1.

In some embodiments, Compound 1 is crystalline. In some embodiments, Compound 1 is crystalline Pattern 4. Crystalline Pattern 4 of Compound 1 is characterized as having at least one of the following properties:
(a) an X-ray powder diffraction (XRPD) pattern with characteristic peaks at 12.3° 2-Theta, 16.5° 2-Theta, 20.6° 2-Theta, and 22.0° 2-Theta.
(b) an X-ray powder diffraction (XRPD) pattern with characteristic peaks at 12.3° 2-Theta, 16.5° 2-Theta, 20.6° 2-Theta, and 22.0° 2-Theta and at least one additional characteristic peak selected from 4.1° 2-Theta, 8.2° 2-Theta, 11.4° 2-Theta, 18.5° 2-Theta, and 24.8° 2-Theta.
(c) an X-ray powder diffraction (XRPD) pattern substantially the same as shown in FIG. 7.

In some embodiments, Crystalline Pattern 4 of Compound 2 is characterized as having at least two of the following properties selected from (a) to (c). In some embodiments, Crystalline Pattern 4 of Compound 1 is characterized as having properties (a), (b), and (c).

Amorphous Compound 2

In some embodiments, Compound 2 is amorphous. In some embodiments, Amorphous Phase of Compound 2 has an XRPD pattern showing a lack of crystallinity.

In some embodiments, Amorphous Phase of Compound 2 provides crystalline Pattern 1 of Compound 2 post GVS.

Compound 2—Pattern 1

Figure 2:
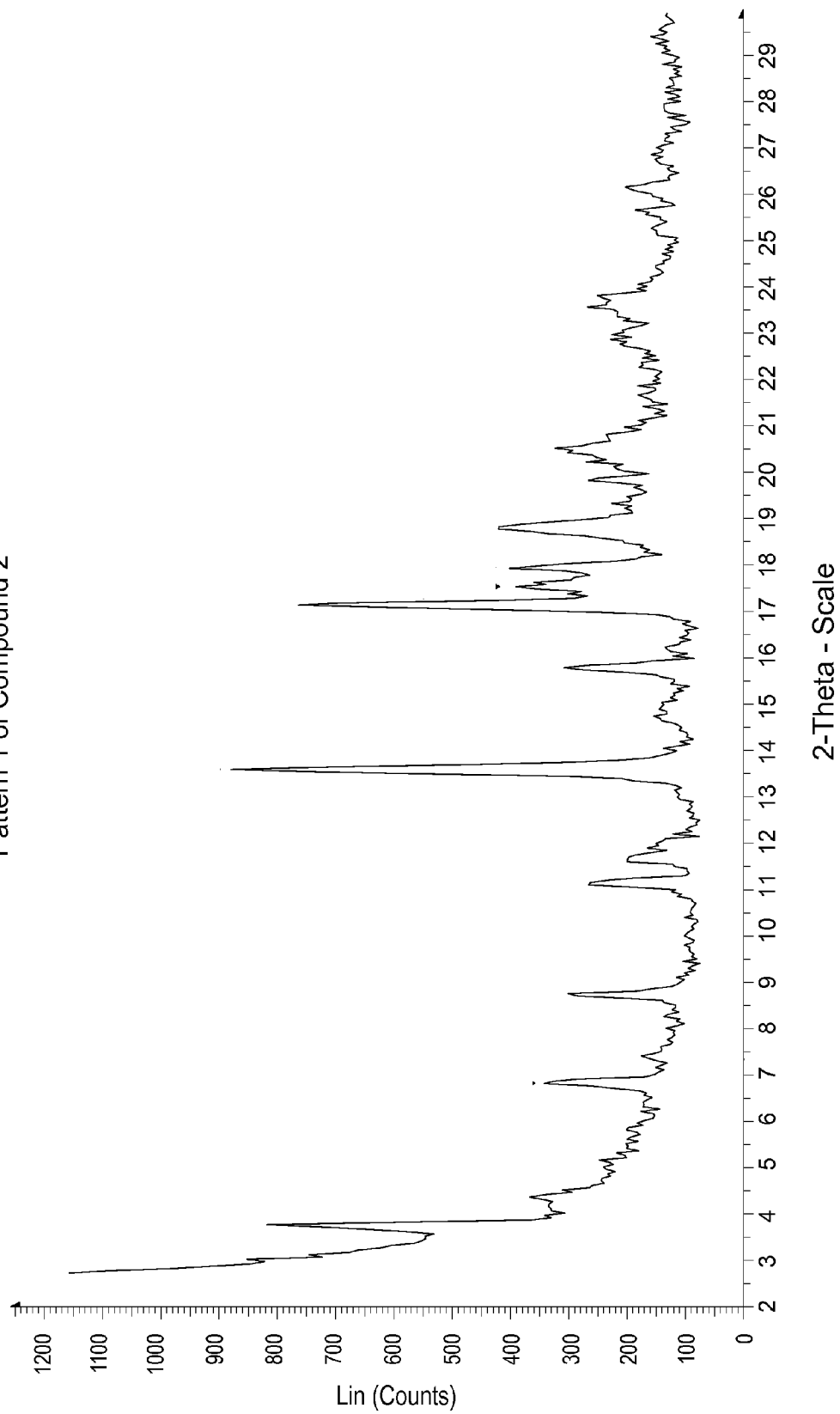
FIG. 2 illustrates the XRPD of Pattern 1 of Compound 2.
Figure 3:
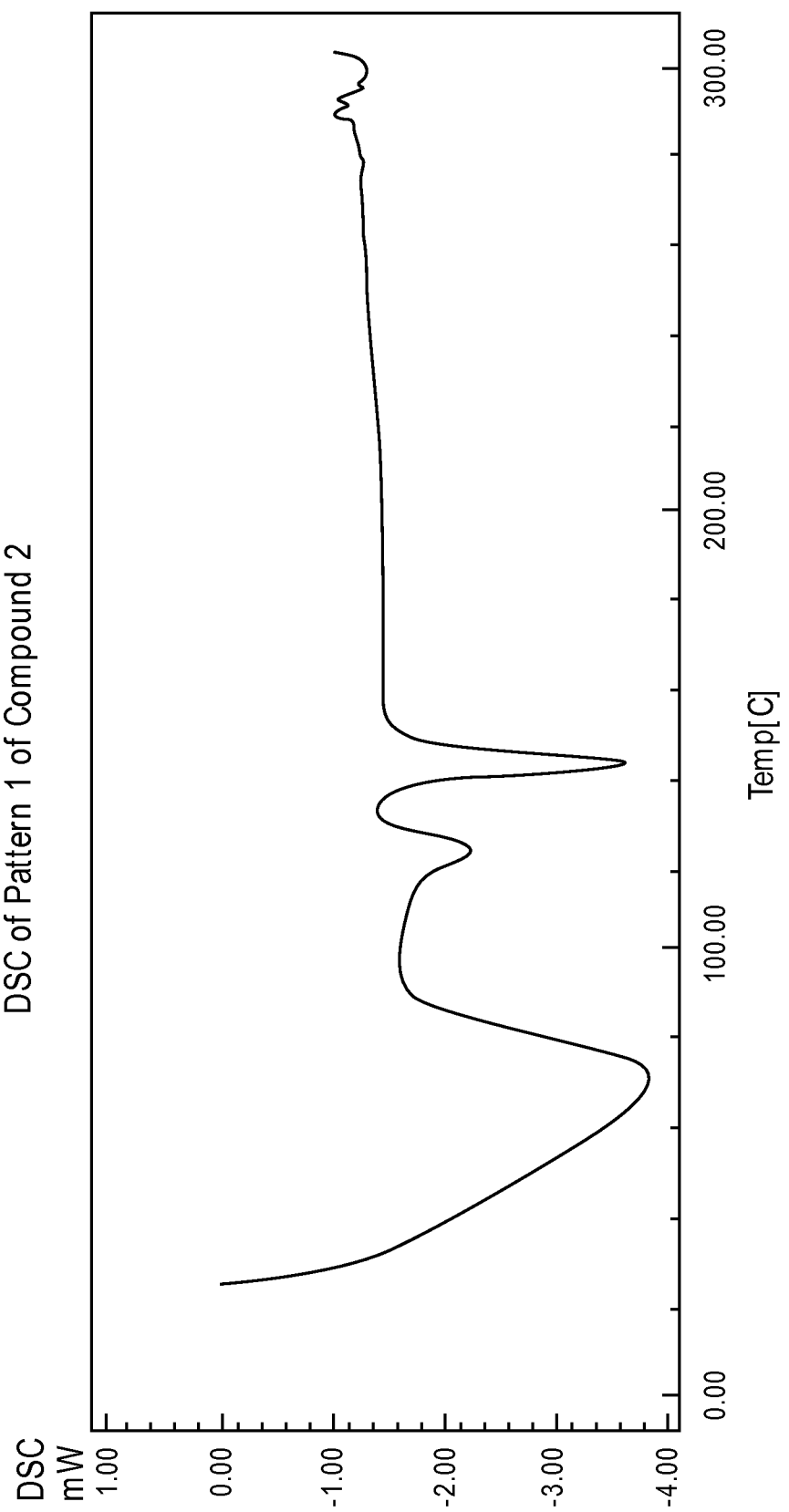
FIG. 3 illustrates the DSC of Pattern 1 of Compound 2.

In some embodiments, Compound 2 is crystalline. In some embodiments, Compound 2 is crystalline Pattern 1. Crystalline Pattern 1 of Compound 2 is characterized as having at least one of the following properties:
(a) an X-ray powder diffraction (XRPD) pattern with characteristic peaks at 3.7° 2-Theta, 13.5° 2-Theta, 17.1° 2-Theta, and 18.8° 2-Theta;
(b) an X-ray powder diffraction (XRPD) pattern with characteristic peaks at 3.7° 2-Theta, 13.5° 2-Theta, 17.1° 2-Theta, and 18.8° 2-Theta and at least one additional characteristic peak selected from 6.8° 2-Theta, 8.7° 2-Theta, 11.1° 2-Theta, 15.7° 2-Theta, 17.5° 2-Theta, and 17.9° 2-Theta;
(c) an X-ray powder diffraction (XRPD) pattern substantially the same as shown in FIG. 2;
(d) a DSC thermogram with endotherms at about 70° C., about 122° C., and about 138° C.;
(e) a DSC thermogram substantially the same as FIG. 3.

In some embodiments, Crystalline Pattern 1 of Compound 2 is characterized as having at least two of the properties selected from (a) to (e). In some embodiments, Crystalline Pattern 1 of Compound 2 is characterized as having at least three of the properties selected from (a) to (e). In some embodiments, Crystalline Pattern 1 of Compound 2 is characterized as having at least four of the properties selected from (a) to (e).

In some embodiments, Crystalline Pattern 1 of Compound 2 is characterized as having property (a) and (c). In some embodiments, Crystalline Pattern 1 of Compound 2 is characterized as having property (d) and (e). In some embodiments, Crystalline Pattern 1 of Compound 2 is characterized as having property (a) or (c) and property (d) or (e). In some embodiments, Crystalline Pattern 1 of Compound 2 is characterized as having properties (a), (b), (c), (d), and (e).

Prodrugs of Compound 1

In some embodiments, Compound 1 is prepared as a prodrug.

A "prodrug of Compound 1" refers to a compound that is converted into Compound 1 in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, prodrugs facilitate transmittal across a cell membrane where water solubility is detrimental to mobility but which then is metabolically hydrolyzed to the carboxylic acid, the active entity, once inside the cell where water-solubility is beneficial. An example, without limitation, of a prodrug would be an ester of Compound 1 (the "prodrug"). A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of Compound 1 increases the bioavailability of Compound 1 when orally administered. In some embodiments, the prodrug of Compound 1 has improved solubility in pharmaceutical compositions over Compound 1.

In some embodiments, a prodrug of Compound 1 is an alkyl ester of Compound 1, such as, for example, methyl ester, ethyl ester, n-propyl ester, iso-propyl ester, n-butyl ester, sec-butyl ester, tert-butyl ester.

Non-limiting examples of prodrugs of Compound 1 include:

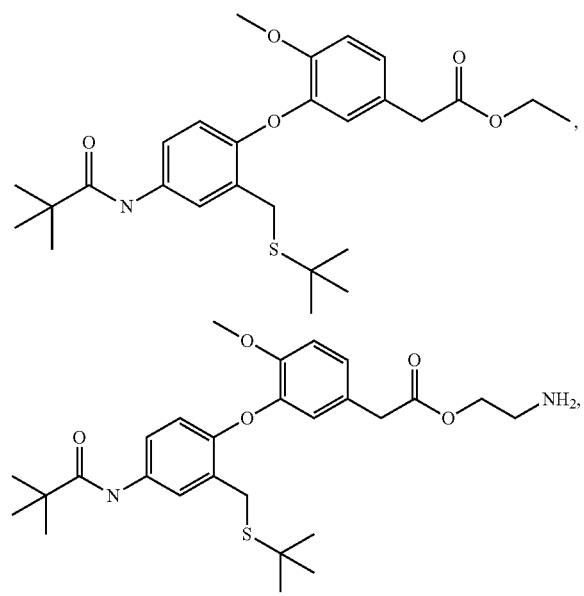

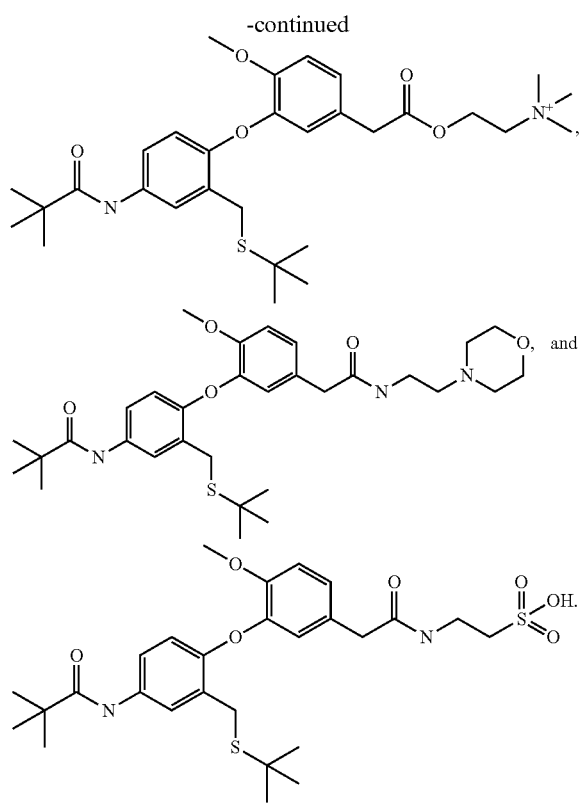

Metabolites of Compound 1

Compound 1 metabolites formed during incubation of Compound 1 with rat, dog, and human liver microsomes, rat and human hepatocytes, as well as those generated in vivo and isolated from rat bile and rat and dog plasma have been investigated. Authentic standards of the majority of the metabolites have been chemically synthesized. The identity of the in vitro and in vivo metabolites were confirmed by comparison with the authentic standard and/or by the fragmentation pattern observed following LC-MS/MS analysis.

The following metabolites of Compound 1 were observed both in vitro and in vivo:
M1—2-(3-(2-(tert-butylsulfinylmethyl)-4-pivalamidophenoxy)-4-methoxyphenyl)acetic acid;
M2—2-(3-(2-(tert-butylsulfonylmethyl)-4-pivalamidophenoxy)-4-methoxyphenyl)acetic acid;
M3—2-(3-(2-(tert-butylthiomethyl)-4-pivalamidophenoxy)-4-hydroxyphenyl)acetic acid;
M4—Acyl-glucuronide of Compound 1;
M5—2-(3-(2-(tert-butylsulfinylmethyl)-4-pivalamidophenoxy)-4-hydroxyphenyl)acetic acid;
M6—Acyl-glucuronide of M3;
M7—Acyl-glucuronide of M1;
M8—Acyl-glucuronide of M2.

Metabolites M1, M2, M3, and M5 are active metabolites of Compound 1.

In some embodiments, sites on Compound 1 are susceptible to various metabolic reactions. Therefore incorporation of appropriate substituents on Compound 1 will reduce, minimize or eliminate this metabolic pathway. In specific embodiments, the appropriate substituent to decrease or eliminate the susceptibility of the aromatic ring to metabolic reactions is, by way of example only, a halogen, deuterium or an alkyl group (e.g. methyl, ethyl).

In some embodiments, Compound 1 is isotopically labeled (e.g. with a radioisotope) or by another other means, including, but not limited to, the use of chromophores or fluorescent moieties, bioluminescent labels, or chemiluminescent labels. In some embodiments, Compound 1 is isotopically-labeled, which is identical to Compound 1 but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on Compound 1 are deuterated. In some embodiments, substitution with deuterium affords certain therapeutic advantages resulting from greater metabolic stability, such as, for example, increased in vivo half-life or reduced dosage requirements.

In one aspect, described is a compound with the following structure:

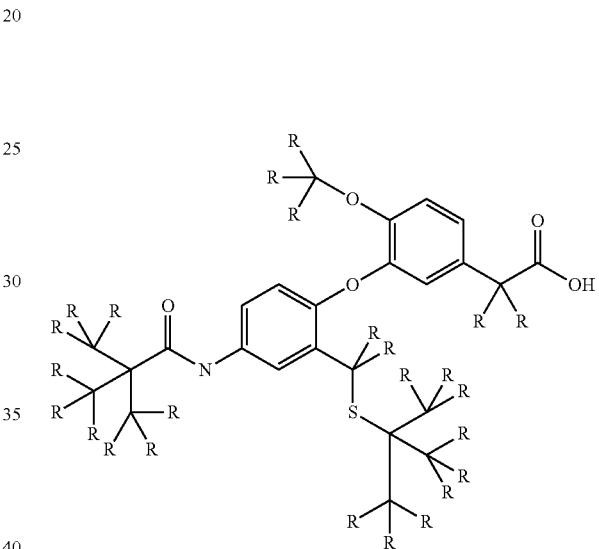

wherein, each R is independently selected from hydrogen or deuterium, or a pharmaceutically acceptable salt thereof.

In some embodiments, each R is independently selected from hydrogen or deuterium such that the compound has one of the following structures:

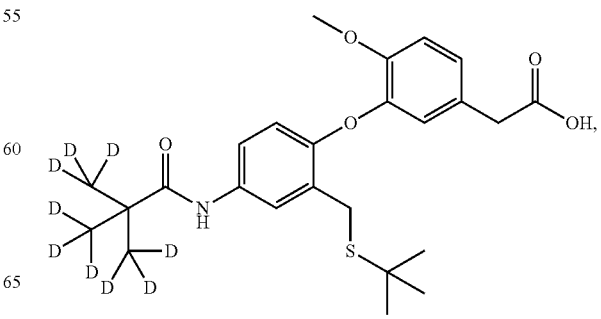

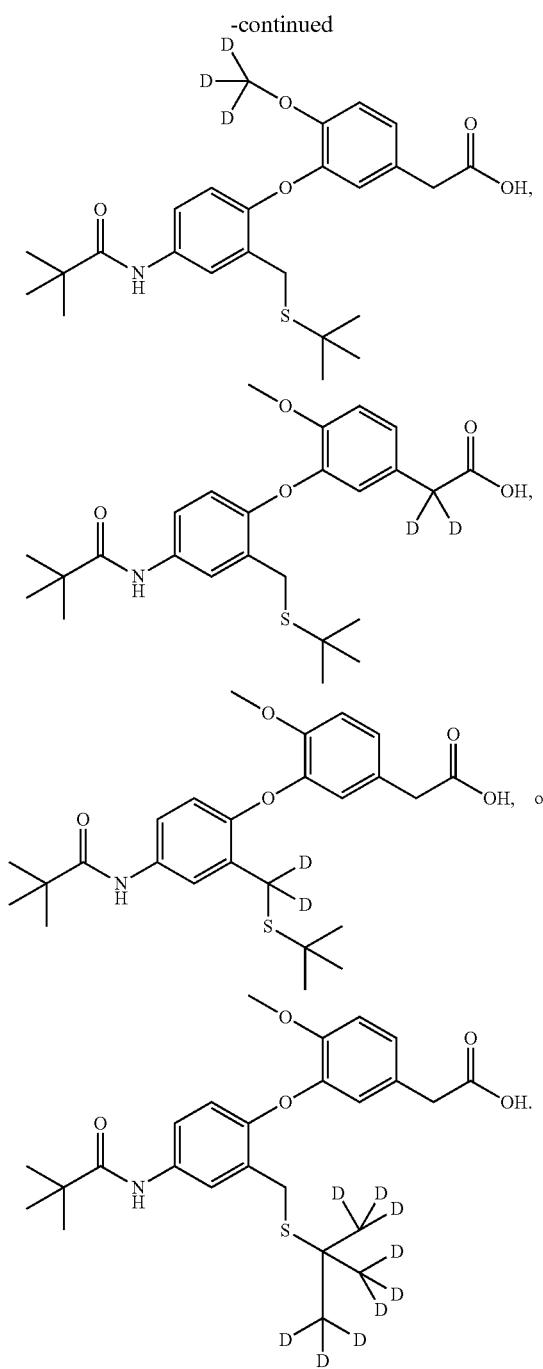

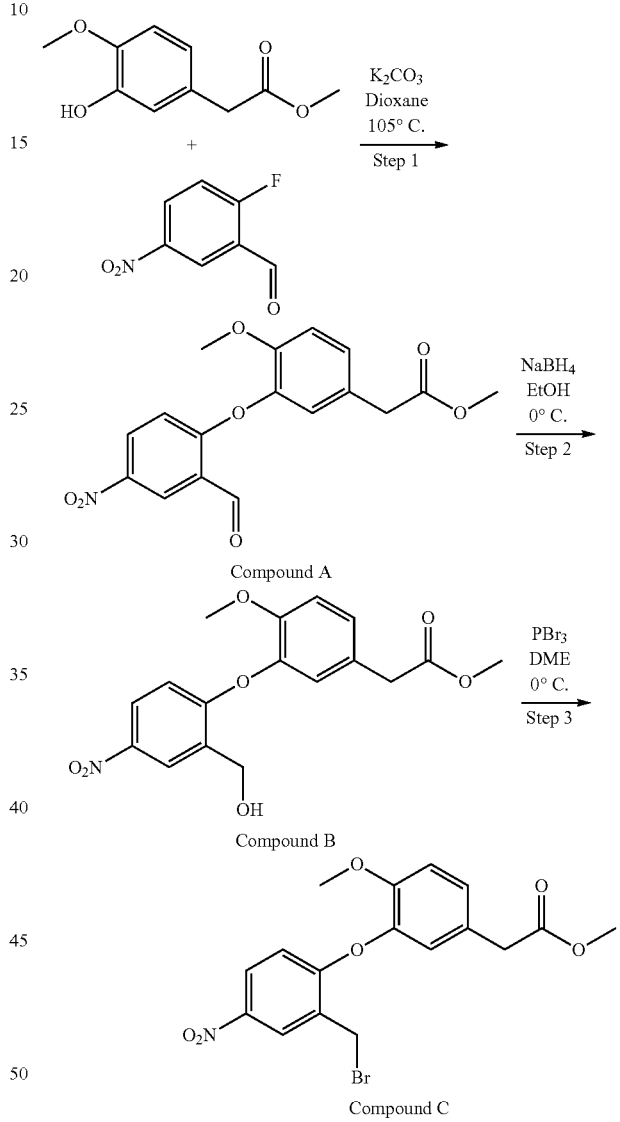

In some embodiments, the pharmaceutically acceptable salt of the compound is a sodium salt.

Synthesis of Compound 1, and Pharmaceutically Acceptable Salts Thereof

Compound 1, and pharmaceutically acceptable salts thereof (e.g. Compound 2), are synthesized as described herein. In additions, solvents, temperatures and other reaction conditions presented herein may vary.

Described herein are processes for the preparation of Compound 1, and pharmaceutically acceptable salts thereof (e.g. Compound 2). In some embodiments, a linear eight step synthetic process starting with 3-hydroxy-4-methoxyphenyl acetic acid methyl ester is used. In some embodiments, 3-hydroxy-4-methoxyphenyl acetic acid is converted to the methyl ester, or other alkyl ester (e.g. ethyl ester, propyl ester, butyl ester, etc).

In one aspect, the preparation of Compound 1, or pharmaceutically acceptable salts thereof (e.g. sodium salt) begins with the steps outlined in Scheme 1.

Step 1: In this step, a SNAr coupling is employed to couple 3-hydroxy-4-methoxyphenyl acetic acid methyl ester and 2-fluoro-5-nitro-benzaldehyde to provide Compound A. To the reactor is added 3-hydroxy-4-methoxyphenyl acetic acid methyl ester, a base, 2-fluoro-5-nitro-benzaldehyde, and a suitable solvent. In some embodiments, the base is potassium carbonate. In some embodiments, the suitable solvent is 1,4-dioxane. The reactor is heated to 70° C.

Methods of forming diaryl ethers include those described herein or described in the art including but not limited to the Ulman Ether synthesis, Chan-Lam coupling, and Buchwald-Hartwig synthesis (D. Ma, Q. Cai, *Org. Lett.*, 2003, 5, 3799-3802; C. G. Bates, et al., *Org. Lett.*, 2002, 4, 2803-2806; C. H. Burgos, et al., *Angew. Chem. Int. Ed.*, 2006, 45, 4321-4326; C. H. Burgos, et al., *Angew. Chem. Int. Ed.,* 2006, 45, 4321-4326; D. M. T. Chan, et al., *Tetrahedron Lett.,* 1998, 39, 2933-2936; Z. Liu, R. C. Larock, *J. Org. Chem.,* 2006, 71, 3198-3209; Y.-J. Chen, H.-H. Chen, *Org. Lett.,* 2006, 8, 5609-5612; F. Li, Q. et al., *Org. Lett.,* 2003, 5, 2169-2171; D. A. Evans, et al., *Tetrahedron Letters,* 1998, 39, 2937-2940; C.-E. Yeom, et al., *Synlett,* 2007, 146-150).

Step 2: In this step, the aldehyde moiety of Compound A is reduced to the alcohol to provide Compound B. In some embodiments, the aldehyde group is reduced with sodium borohydride. Suitable solvents for the reduction of the aldehyde with sodium borohydride include, but are not limited to, 1,4-dioxane and tetrahydrofuran.

Step 3: In this step, the alcohol group of Compound B is converted to the corresponding bromide to provide Compound C. The reactor is charged with Compound B and a suitable solvent followed by the addition of phosphorous tribromide. In some embodiments, the suitable solvent is 1,2-dimethoxyethane.

In some embodiments, Compound C is prepared as outlined in Scheme 2.

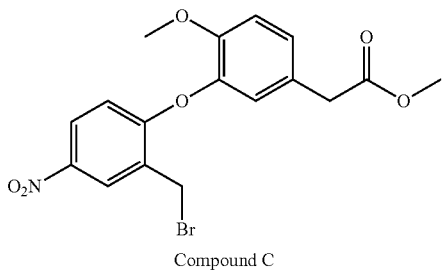

Compound C

Step 1: In this alternative step, a SNAr coupling is employed to couple 3-bromo-4-methoxyphenyl acetic acid methyl ester and 2-hydroxy-5-nitro-benzaldehyde to provide Compound A.

Steps 2 and 3 are then performed as described for Scheme 1 to provide Compound C.

In some embodiments, Compound C is then elaborated into Compound 1, and pharmaceutically acceptable salts thereof (e.g. Compound 2) as described in Scheme 3.

Scheme 2.

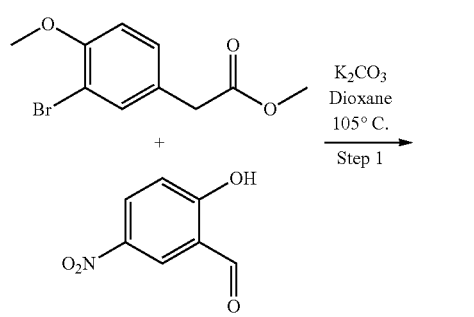

Compound A

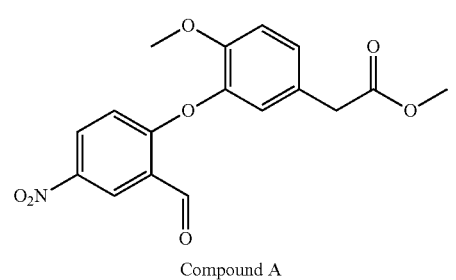

Compound B

Scheme 3.

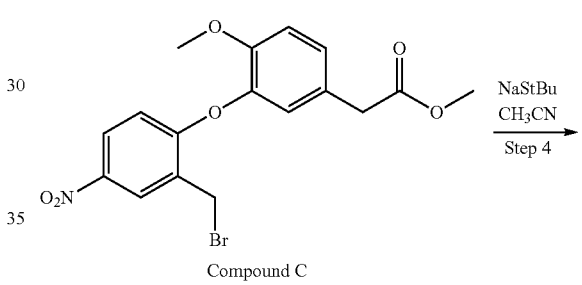

Compound C

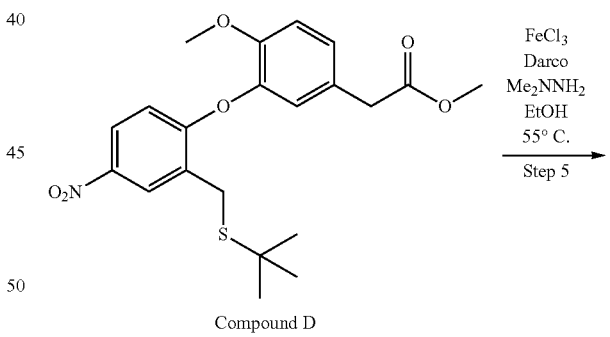

Compound D

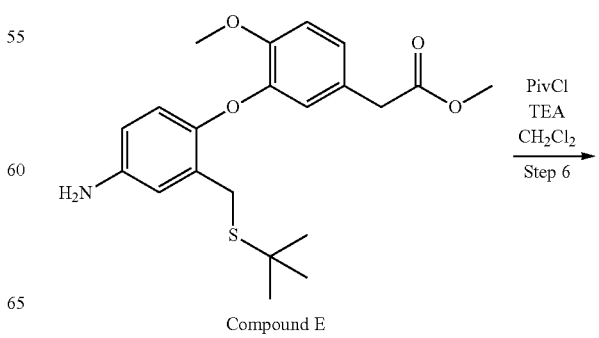

Compound E

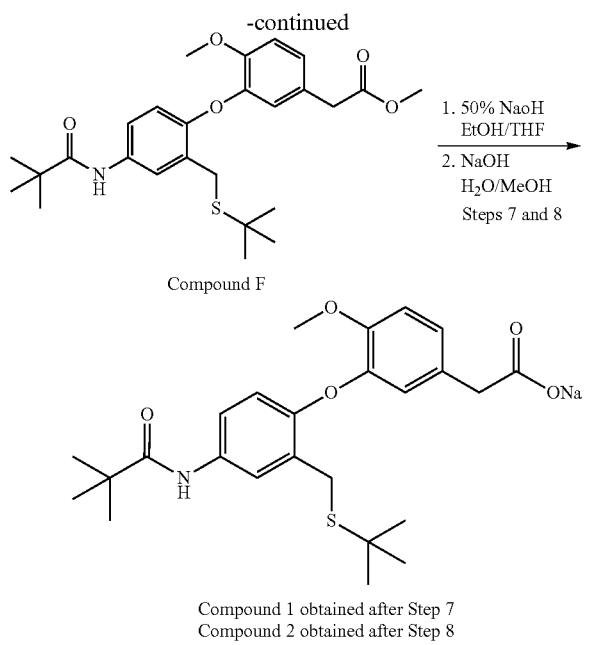

Compound F

Compound 1 obtained after Step 7
Compound 2 obtained after Step 8

Step 4: In this step, a $S_N2$ reaction is used to install the thiol moiety in Compound D. In some embodiments, a reactor is charged with Compound C, a suitable solvent, and 2-methyl-2-propanethiol and mixed at 0° C. for approximately 1 hour. A suitable base is added to the reactor. In some embodiments, the suitable solvent is tetrahydrofuran. In some embodiments, the suitable base is sodium hydride.

Step 5: In this step, the nitro group of Compound D is reduced to the corresponding amine to provide Compound E. In some embodiments, a reactor is charged with Compound D, activated charcoal, a suitable solvent, and 1,1-dimethylhydrazine. In some embodiments, the suitable solvent is methanol. The reaction mixture is heated. Ferric chloride is added in portions.

Other conditions for the reduction of nitro groups to amines include: treatment with iron trichloride in the presence of hydrazine; catalytic hydrogenation using palladium-on-carbon (Bavin, P. M. G. (1973). Org. Synth.; Coll. Vol. 5: 30), platinum oxide, or Raney nickel (Allen, C. F. H.; VanAllan, J. (1955)). Org. Synth.; Coll. Vol. 3: 63), iron in acidic media (Fox, B. A.; Threlfall, T. L. (1973). Org. Synth.; Coll. Vol. 5: 346), sodium hydrosulfite (Redemann, C. T.; Redemann, C. E. (1955). Org. Synth.; Coll. Vol. 3: 69), sodium sulfide (or hydrogen sulfide and base), tin(II) chloride, titanium(III) chloride, and zinc.

Step 6: In this step, the amino group of Compound E is acylated with trimethylacetylchloride. In some embodiments, the reactor is charged with Compound E, a suitable solvent, and a suitable base. Trimethylacetyl chloride is then added. In some embodiments, the suitable solvent is dichloromethane. In some embodiments, the suitable base is triethylamine.

Step 7: In this step, the ester group of Compound F is hydrolyzed to the carboxylic acid. In some embodiments, a reactor is charged with Compound F, a suitable solvent and a suitable base. In some embodiments, the hydrolysis reaction is performed in a mixture of tetrahydrofuran, methanol and water. In some embodiments, the suitable base is sodium hydroxide. Other suitable bases include lithium hydroxide and potassium hydroxide.

Step 8: In this step, the carboxylic acid of Compound 1 is converted to the sodium carboxylate. In some embodiments, a reactor is charged with a suitable solvent or solvent mixture, Compound 1 and sodium hydroxide. In some embodiments, the solvent mixture is methanol and tetrahydrofuran. In some embodiments, a 50% aqueous sodium hydroxide solution is added. When a pH of approximately 9 to 10 is achieved, the solution is concentrated to exchange solvents with MTBE. The mixture is warmed to approximately 55° C. until a clear solution is formed. The mixture is cooled to 25° C., charged with heptane, and agitated. The slurry is filtered, and washed with heptane, and then dried to a constant weight. This process generates an amorphous form of Compound 2.

In some embodiments, the amorphous form of Compound 2 is added to a reactor with acetone and warmed to 40° C. until dissolved. Heptane is then added and then warmed again to reflux (~60° C.). The mixture is agitated and cooled to 20° C. Additional heptane is then added to form the slurry. The material is filtered, and washed with heptane, and then dried to a constant weight. In some embodiments, Compound 2 is then passed through a 10 mesh screen. This process provides Pattern 1 of Compound 2.

The last step is the formation of the sodium salt that isolates the drug substance in an acetone/heptane solvent system to ensure crystalline solids.

Although the methyl ester is shown in Schemes 1 to 3, other alkyl ester are contemplated. In some embodiments, other alkyl esters include ethyl esters, n-propyl esters, iso-propyl esters, n-butyl esters, sec-butyl esters, tert-butyl esters, and the like.

In some embodiments, Compound 1 is treated with potassium hydroxide in a solvent to form Compound 1, potassium salt. In some embodiments, Compound 1 is treated with lithium hydroxide in a solvent to form Compound 1, lithium salt. In some embodiments, Compound 1 is treated with calcium hydroxide in a solvent to form Compound 1, calcium salt.

In some embodiments, Compound 1 is treated with dicyclohexylamine in a solvent to form the corresponding salt. In some embodiments, Compound 1 is treated with N-methyl-D-glutamine in a solvent to form the corresponding salt. In some embodiments, Compound 1 is treated with choline in a solvent to form the corresponding salt. In some embodiments, Compound 1 is treated with tris(hydroxymethyl)methylamine in a solvent to form the corresponding salt.

In some embodiments, Compound 1 is treated with arginine in a solvent to form the corresponding salt. In some embodiments, Compound 1 is treated with lysine in a solvent to form the corresponding salt.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising salts of Compound 1 comprise an organic solvent(s). In some embodiments, compositions comprising salts of Compound 1 comprise a residual amount of an organic solvent(s). In some embodiments, compositions comprising salts of Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising a salt of Compound 1 include a detectable amount of an organic solvent. In some embodiments, the salt of Compound 1 is a sodium salt (i.e. Compound 2). In some embodiments, the organic solvent is a Class 3 solvent.

In one aspect, the salt of Compound 1 is a sodium salt, potassium salt, lithium salt, calcium salt, magnesium salt, ammonium salt, choline salt, protonated dicyclohexylamine salt, protonated N-methyl-D-glucamine salt, protonated tris (hydroxymethyl)methylamine salt, arginine salt, or lysine salt. In one aspect, the salt of Compound 1 is a sodium salt.

In other embodiments are compositions comprising Compound 2, wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound 2, wherein the composition comprises a detectable amount of solvent which is less than about 5000 ppm. In yet a further embodiment are compositions comprising Compound 2, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Certain Terms

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, organic synthesis, biochemistry, recombinant DNA techniques and pharmacology, within the skill of the art are employed. In this application, the use of "or" means "and/or" unless stated otherwise. Furthermore, use of the term "including" as well as other forms, such as "include", "includes," and "included," is not limiting.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is Compound 1. In some embodiments, an API is Compound 2. Provided herein is an active pharmaceutical ingredient (API), Compound 1, or pharmaceutically acceptable salt thereof (e.g. Compound 2), with a purity of greater than 80%, greater than 85%, greater than 90%, greater than 95%, greater than 96%, greater than 97%, greater than 98%, greater than 98%, or greater than 99%. In specific embodiments, provided herein is an active pharmaceutical ingredient (API), Compound 2, with a purity of greater than 80%, greater than 85%, greater than 90%, greater than 95%, greater than 96%, greater than 97%, greater than 98%, or greater than 99%. In some embodiments, the API is solvated. In some embodiments, the API is hydrated.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1 or a pharmaceutically acceptable salt, and a co-agent, are both administered to a patient simultaneously in the form of a single entity or dosage. The term "non-fixed combination" means that the active ingredients, e.g. Compound 1 or a pharmaceutically acceptable salt, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of Compound 1, or pharmaceutically acceptable salt and/or solvate thereof, with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

An "alkyl" group refers to an aliphatic hydrocarbon group. The alkyl moiety is branched, straight chain, or cyclic. The alkyl group may be designated as "$C_1$-$C_6$alkyl". In one aspect, an alkyl is selected from methyl, ethyl, propyl, isopropyl, butyl, isobutyl, tert-butyl, pentyl, neopentyl, hexyl, ethenyl, propenyl, allyl, butenyl, cyclopropyl, cyclobutyl, cyclopentyl, cyclohexyl, and the like.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231> Method II, etc) (ICH guidances, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount. The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study The terms "co-administration" or the like, as used herein, are meant to encompass administration of the selected therapeutic agents to a single patient, and are intended to include treatment regimens in which the agents are administered by the same or different route of administration or at the same or different time.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized (biotransformed). The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases (UGT) catalyze the transfer of an activated glucuronic-acid molecule to aromatic alcohols, aliphatic alcohols, carboxylic acids, amines and free sulphydryl groups (e.g. conjugation reactions). In some embodiments, compounds disclosed herein are metabolite to provide taurine metabolites. Further information on metabolism is available in The Pharmacological Basis of Therapeutics, 9th Edition, McGraw-Hill (1996). In one embodiment, metabolites of the compounds disclosed herein are identified either by administration of compounds to a host and analysis of tissue samples from the host, or by incubation of compounds with hepatic cells in vitro and analysis of the resulting compounds.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Non-competitive antagonists (also known as allosteric antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

Partial agonists are defined as drugs which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

The term "subject" or "patient" encompasses mammals. In one aspect, the mammal is a human. In another aspect, the mammal is a non-human primate such as chimpanzee, and other apes and monkey species. In one aspect, the mammal is a farm animal such as cattle, horse, sheep, goat, or swine. In one aspect, the mammal is a domestic animal such as rabbit, dog, or cat. In one aspect, the mammal is a laboratory animal, including rodents, such as rats, mice and guinea pigs, and the like.

"Bioavailability" refers to the percentage of the weight of Compound 1, or a pharmaceutically acceptable salt and/or solvate thereof, dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which Compound 1, or a pharmaceutically acceptable salt and/or solvate thereof, is absorbed into the general circulation when the pharmaceutical composition is taken orally as compared to intravenous injection.

"Blood plasma concentration" refers to the concentration Compound 1, in the plasma component of blood of a mammal. It is understood that the plasma concentration of Compound 1 may vary significantly between subjects, due to variability with respect to metabolism and/or interactions with other therapeutic agents. In one aspect, the blood plasma concentration of Compound 1 varies from subject to subject. Likewise, values such as maximum plasma concentration ($C_{max}$) or time to reach maximum plasma concentration ($T_{max}$), or total area under the plasma concentration time curve ($AUC_{(0-\infty)}$) vary from subject to subject. Due to this variability, in one embodiment, the amount necessary to constitute "a therapeutically effective amount" of Compound 1 varies from subject to subject.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

"Serum concentration" or "Plasma concentration" describes the blood serum or blood plasma concentration, typically measured in mg, µg, or ng of therapeutic agent per ml, dl, or 1 of blood serum, absorbed into the bloodstream after administration. Plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

"Treat" or "treatment" as used herein refers to any treatment of a disorder or disease, such as preventing the disorder or disease from occurring in a subject predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder either prophylactically and/or therapeutically. Thus, as used herein, the term "treat" is used synonymously with the term "prevent."

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

In some embodiments, for oral administration, Compound 1, or a pharmaceutically acceptably salt thereof (e.g. Compound 2), are formulated by combining the active compound with pharmaceutically acceptable carriers or excipients. Such carriers enable Compound 1, or a pharmaceutically acceptably salt thereof (e.g. Compound 2) to be formulated as tablets, powders, pills, dragees, capsules, liquids, gels, syrups, elixirs, slurries, suspensions and the like, for oral ingestion by a patient to be treated. In some embodiments, for oral administration, Compound 1, or a pharmaceutically acceptably salt thereof (e.g. Compound 2), is formulated without combining the active compound with pharmaceutically acceptable carriers or excipients and is placed directly into a capsule for administration to a mammal.

In some embodiments, the pharmaceutical compositions will include at least one pharmaceutically acceptable carrier, diluent or excipient and Compound 1 as an active ingredient in free-acid or free-base form, or in a pharmaceutically acceptable salt form. In some embodiments, the pharmaceutical compositions will include at least one pharmaceutically acceptable carrier, diluent or excipient and Compound 2.

The pharmaceutical compositions described herein include Compound 1, or a pharmaceutically acceptable salt thereof (e.g. Compound 2). In some embodiments, the pharmaceutical compositions described herein include Compound 1. In some embodiments, the pharmaceutical compositions described herein include amorphous Compound 1. In some embodiments, the pharmaceutical compositions described herein include crystalline Compound 1. In some embodiments, the pharmaceutical compositions described herein include Compound 2. In some embodiments, the pharmaceutical compositions described herein include amorphous Compound 2. In some embodiments, the pharmaceutical compositions described herein include crystalline Compound 2.

In some embodiments, the pharmaceutical compositions described herein include: (a) Compound 1, or a pharmaceutically acceptable salt thereof (e.g. Compound 2); and one or more of the following: (b) binders; (c) disintegrants; (d) fillers (diluents); (e) lubricants; (f) glidants (flow enhancers); (g) compression aids; (h) colors; (i) sweeteners; (j) preservatives; (k) suspensing/dispersing agents; (l) film formers/coatings; (m) flavors; (O) printing inks; (p) solubilizers; (q) alkalizing agents; (r) buffering agents; (s) antioxidants; (t) effervescent agents.

In some embodiments, the pharmaceutical compositions described herein include: (a) Compound 1, or a pharmaceutically acceptable salt thereof (e.g. Compound 2); and (b) a capsule shell.

In some embodiments, pharmaceutical compositions described herein include one or more of the following in addition to Compound 1, or a pharmaceutically acceptable salt thereof (e.g. Compound 2): (a) magnesium stearate; (b) lactose; (c) microcrystalline cellulose; (d) silicified microcrystalline cellulose; (e) mannitol; (f) starch (corn); (g) silicon dioxide; (h) titanium dioxide; (i) stearic acid; (j) sodium starch glycolate; (k) gelatin; (l) talc; (m) sucrose; (n) aspartame; (o) calcium stearate; (p) povidone; (q) pregelatinized starch; (r) hydroxy propyl methylcellulose; (s) OPA products (coatings & inks); (t) croscarmellose; (u) hydroxy propyl cellulose; (v) ethylcellulose; (w) calcium phosphate (dibasic); (x) crospovidone; (y) shellac (and glaze); (z) sodium carbonate; (aa) hypromellose.

In one embodiment, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, silicified microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate.

In one embodiment, the pharmaceutical compositions described herein are formulated into any suitable dosage form, including but not limited to, aqueous oral dispersions, solid oral dosage forms, fast melt formulations, effervescent formulations, lyophilized formulations, tablets, capsules, pills, controlled release formulations, enteric coated tablets, inhaled powder, inhaled dispersion, IV formulations.

In further embodiments, the pharmaceutical compositions provided herein may be provided as compressed tablets, tablet triturates, rapidly dissolving tablets, multiple compressed tablets, or enteric-coated tablets, sugar-coated, or film-coated tablets.

Pharmaceutical dosage forms can be formulated in a variety of methods and can provide a variety of drug release profiles, including immediate release, sustained release, and delayed release. In some cases it may be desirable to prevent drug release after drug administration until a certain amount of time has passed (i.e. timed release), to provide substantially continuous release over a predetermined time period (i.e. sustained release) or to provide release immediately following drug administration (i.e., immediate release).

In some embodiments, formulations provide a therapeutically effective amount of Compound 1, or a pharmaceutically acceptable salt thereof (e.g. Compound 2), enabling, for example, once a week, twice a week, three times a week, four times a week, five times a week, once every other day, once-a-day, twice-a-day (b.i.d.), or three times a day (t.i.d.) administration if desired. In one embodiment, the formulation provides a therapeutically effective amount of Compound 1, or a pharmaceutically acceptable salt thereof (e.g. Compound 2) enabling once-a-day administration.

In one embodiment, Compound 1, or a pharmaceutically acceptable salt thereof (e.g. Compound 2) is formulated into an immediate release form that provides for once-a-day administration. Generally speaking, one will desire to administer an amount of Compound 1, or a pharmaceutically acceptable salt thereof (e.g. Compound 2) that is effective to achieve a plasma level commensurate with the concentrations found to be effective in vivo for a period of time effective to elicit a therapeutic effect.

In some embodiments, Compound 1, or a pharmaceutically acceptable salt thereof (e.g. Compound 2) and one or more excipients are dry blended and compressed into a mass, such as a tablet, having a hardness sufficient to provide a pharmaceutical composition that substantially disintegrates within less than about 10 minutes, less than about 15 minutes, less than about 20 minutes, less than about 25 minutes, less than about 30 minutes, less than about 35 minutes, or less than about 40 minutes, after oral administration, thereby releasing the Compound 1, or a pharmaceutically acceptable salt thereof (e.g. Compound 2) formulation into the gastrointestinal fluid.

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia.). Immediate release pharmaceutical compositions include capsules, tablets, pills, oral solutions, powders, beads, pellets, particles, and the like.

Excipients used in pharmaceutical compositions should be selected on the basis of compatibility with Compound 1, or a pharmaceutically acceptable salt thereof (e.g. Compound 2) and the release profile properties of the desired dosage form. Exemplary excipients include, e.g., binders, suspending agents, disintegration agents, filling agents, surfactants, solubilizers, stabilizers, lubricants, wetting agents, diluents, and the like.

Binders impart cohesiveness to solid oral dosage form formulations: for powder filled capsule formulation, they aid in plug formation that is filled into soft or hard shell capsules and for tablet formulation, they ensure the tablet remaining intact after compression and help assure blend uniformity prior to a compression or fill step.

In some embodiments, the binder(s) are selected from starches, sugars, povidone, cellulose or modified cellulose such as microcrystalline cellulose, hydroxypropyl methyl cellulose, lactose, or sugar alcohols like xylitol, sorbitol or maltitol. In some embodiments, the binder is hydroxypropyl methyl cellulose. In some embodiments, the binder is hypromellose (e.g., Methocel E5).

In general, binder levels of 20-70% are used in powderfilled gelatin capsule formulations. Binder usage level in tablet formulations varies whether direct compression, wet granulation, roller compaction, or usage of other excipients such as fillers which itself acts as moderate binder.

Dispersing agents, and/or viscosity modulating agents include materials that control the diffusion and homogeneity of a drug through liquid media or a granulation method or blend method. In some embodiments, these agents also facilitate the effectiveness of a coating or eroding matrix.

Diluents increase bulk of the composition to facilitate compression or create sufficient bulk for homogenous blend for capsule filling.

The term "disintegrate" includes both the dissolution and dispersion of the dosage form when contacted with gastrointestinal fluid. "Disintegration agents or disintegrants" facilitate the breakup or disintegration of a substance. In some embodiments, one aspect, solid oral dosage forms include up to 15% w/w of disintegrant. In some embodiments, the disintegrant is croscarmellose sodium. In another aspect, the disintegrant is sodium starch glycolate or crospovidone.

Filling agents include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In one aspect, the filler is lactose (e.g. monohydrate). In another aspect, the filler is mannitol, or dicalcium phosphate. In another aspect, the filler is mannitol, microcrystalline cellulose, dicalcium phosphate or sorbitol.

Gastrointestinal fluid is the fluid of stomach secretions of a subject or the saliva of a subject after oral administration of a composition described herein, or the equivalent thereof. An "equivalent of stomach secretion" includes, e.g., an in vitro fluid having similar content and/or pH as stomach secretions such as a 1% sodium dodecyl sulfate solution or 0.1N HCl solution in water. In addition, simulated intestinal fluid (USP) is an aqueous phosphate buffer system at pH 6.8.

Lubricants and glidants are compounds that prevent, reduce or inhibit adhesion or friction of materials. In one aspect, solid oral dosage forms include about 0.25% w/w to about 2.5% w/w of lubricant. In another aspect solid oral dosage forms include about 0.5% w/w to about 1.5% w/w of lubricant.

In some embodiments, the solid dosage forms described herein are in the form of a tablet, (including an immediate release tablet, an extended release tablet, a sustained release tablet, a enteric coated tablet, a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, multiparticulate dosage forms, pellets, or granules.

In other embodiments, the pharmaceutical formulation is in the form of a powder. In still other embodiments, the pharmaceutical formulation is in the form of a tablet, including but not limited to, an immediate release tablet. Additionally, pharmaceutical formulations described herein are administered as a single dosage or in multiple dosages. In some embodiments, the pharmaceutical formulation is administered in two, or three, or four tablets.

In some embodiments, solid dosage forms, e.g., tablets, effervescent tablets, and capsules, are prepared by mixing Compound 1, or a pharmaceutically acceptable salt thereof (e.g. Compound 2) with one or more pharmaceutical excipients to form a bulk blend composition. When referring to these bulk blend compositions as homogeneous, it is meant that the Compound 1, or a pharmaceutically acceptable salt thereof (e.g. Compound 2) particles are dispersed evenly throughout the composition so that the composition is capable of being readily subdivided into equally effective unit dosage forms, such as tablets, pills, or capsules. In one embodiment, the individual unit dosages also include film coatings, which disintegrate upon oral ingestion or upon contact with diluent. In one embodiment, these formulations are manufactured by conventional techniques.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

Compressed tablets are solid dosage forms prepared by compacting the bulk blend formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings comprising Opadry® typically range from about 1% to about 5% of the tablet weight. In other embodiments, the compressed tablets include one or more excipients.

Provided herein are pharmaceutical compositions in film-coated dosage forms, which comprise a combination of an active ingredient, or a pharmaceutically acceptable salt, solvate, or prodrug thereof; and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating.

Further provided herein are pharmaceutical compositions in enteric coated dosage forms, which comprise a combination of an active ingredient, or a pharmaceutically acceptable salt, solvate, or prodrug thereof; and one or more release controlling excipients for use in an enteric coated dosage form. The pharmaceutical compositions also comprise non-release controlling excipients.

Enteric-coatings are coatings that resist the action of stomach acid but dissolve or disintegrate in the intestine.

In one aspect, the oral solid dosage form disclosed herein include an enteric coating(s). Enteric coatings include one or more of the following: cellulose acetate phthalate; methyl acrylate-methacrylic acid copolymers; cellulose acetate succinate; hydroxy propyl methyl cellulose phthalate; hydroxy propyl methyl cellulose acetate succinate (hypromellose acetate succinate); polyvinyl acetate phthalate (PVAP); methyl methacrylate-methacrylic acid copolymers; methacrylic acid copolymers, cellulose acetate (and its succinate and phthalate version); styrol maleic acid co-polymers; polymethacrylic acid/acrylic acid copolymer; hydroxyethyl ethyl cellulose phthalate; hydroxypropyl methyl cellulose acetate succinate; cellulose acetate tetrahydrophtalate; acrylic resin; shellac.

An enteric coating is a coating put on a tablet, pill, capsule, pellet, bead, granule, particle, etc. so that it doesn't dissolve until it reaches the small intestine.

Sugar-coated tablets are compressed tablets surrounded by a sugar coating, which may be beneficial in covering up objectionable tastes or odors and in protecting the tablets from oxidation.

Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets. In some embodiments, tablets are coated with water soluble, pH independent film coating which allows for immediate disintegration for fast, active release (e.g. Opadry products).

In some embodiments, the pharmaceutical compositions provided herein are in the form of a controlled release dosage form. As used herein, the term "controlled release" refers to a dosage form in which the rate or place of release of the active ingredient(s) is different from that of an immediate dosage form when orally administered. Controlled release dosage forms include delayed-, extended-, prolonged-, sustained-, pulsatile-, modified-, targeted-, programmed-release. The pharmaceutical compositions in controlled release dosage forms are prepared using a variety of modified release devices and methods including, but not limited to, matrix controlled release devices, osmotic controlled release devices, multiparticulate controlled release devices, ion-exchange resins, enteric coatings, multilayered coatings, and combinations thereof. The release rate of the active ingredient(s) can also be modified by varying the particle sizes.

In contrast to immediate release compositions, controlled release compositions allow delivery of an agent to a human over an extended period of time according to a predetermined profile. Such release rates can provide therapeutically effective levels of agent for an extended period of time and thereby provide a longer period of pharmacologic response. Such longer periods of response provide for many inherent benefits that are not achieved with the corresponding immediate release preparations. In one aspect, controlled release compositions of Compound 1, or a pharmaceutically acceptable salt thereof, provide therapeutically effective levels of Compound 1 for an extended period of time and thereby provide a longer period of pharmacologic response.

Delayed release as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above.

In some embodiments, the pharmaceutical compositions provided herein is in a modified release dosage form that is fabricated using a matrix controlled release device (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

In some embodiments, a matrix controlled release system includes an enteric coating so that no drug is released in the stomach.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include bottles of tablets or capsules.

In other embodiments a powder comprising the Compound 1, or a pharmaceutically acceptable salt thereof (e.g. Compound 2) formulations described herein are formulated to include one or more pharmaceutical excipients and flavors. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In still other embodiments, effervescent powders are prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid.

The method of preparation of the effervescent granules described herein employs three basic processes: wet granulation, dry granulation and fusion. The fusion method is used for the preparation of most commercial effervescent powders. It should be noted that, although these methods are intended for the preparation of granules, the formulations of effervescent salts described herein, in one embodiment, are also prepared as tablets, according to technology for tablet preparation.

In one embodiment, pharmaceutical preparations which are used orally include push-fit capsules made of gelatin, as well as soft, sealed capsules made of gelatin and a plasticizer, such as glycerol or sorbitol. In one embodiment, the push-fit capsules contain the active ingredients in admixture with filler such as lactose, binders such as starches, and/or lubricants such as talc or magnesium stearate and, optionally, stabilizers. In one embodiment, the push-fit capsules contain the active ingredient only without additional inactive ingredients. In one embodiment, in soft capsules, the active compounds are dissolved or suspended in suitable liquids, such as fatty oils, liquid paraffin, or liquid polyethylene glycols. In addition, in one embodiment, stabilizers are added. In other embodiments, the formulation is placed in a sprinkle capsule, wherein the capsule is swallowed whole or the capsule is opened and the contents sprinkled on food prior to eating.

All formulations for oral administration should be in dosages suitable for such administration.

In some embodiments, pharmaceutical formulations are provided comprising Compound 1, or a pharmaceutically acceptable salt thereof (e.g. Compound 2) and at least one dispersing agent or suspending agent for oral administration to a subject. In one embodiment, the formulation is a powder and/or granules for suspension, and upon admixture with water, a substantially uniform suspension is obtained.

A suspension is "substantially uniform" when it is mostly homogenous, that is, when the suspension is composed of approximately the same concentration of Compound 1, or a pharmaceutically acceptable salt thereof (e.g. Compound 2) at any point throughout the suspension (USP Chapter 905).

Liquid formulation dosage forms for oral administration are aqueous suspensions or non-aqueous suspensions.

Liquid formulation dosage forms for oral administration are aqueous suspensions selected from, but not limited to, pharmaceutically acceptable aqueous oral dispersions, emulsions, solutions, and syrups. See, e.g., Singh et al., *Encyclopedia of Pharmaceutical Technology*, $2^{nd}$ Ed., pp. 754-757 (2002). In addition to including Compound 1, or a pharmaceutically acceptable salt thereof (e.g. Compound 2), the liquid dosage forms include additives, such as: (a) disintegrating agents; (b) dispersing agents; (c) wetting agents; (d) preservatives; (e) viscosity enhancing agents; (f) sweetening agents; (g) flavoring agents; (h) solibizing agents (bioavailability enhancers).

In one embodiment, the aqueous suspensions and dispersions described herein remain in a homogenous state, as defined above by USP Chapter 905, for at least 4 hours.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is aqueous.

Liquid compositions illustratively take the form of a liquid where the agent (e.g. Compound 1, or a pharmaceutically acceptable salt thereof (e.g. Compound 2)) is present in solution, in suspension or both. In one embodiment, the liquid composition is non-aqueous.

In one embodiment, the aqueous suspension also contains one or more polymers as suspending agents. Useful polymers include water-soluble polymers such as cellulosic polymers, e.g., hydroxypropyl methylcellulose, and water-insoluble polymers such as cross-linked carboxyl-containing polymers. In one embodiment, useful compositions also comprise an mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

In one embodiment, pharmaceutical compositions also include one or more pH adjusting agents or buffering agents, including acids such as acetic, boric, citric, lactic, phosphoric and hydrochloric acids; bases such as sodium hydroxide, sodium phosphate, sodium borate, sodium carbonate, sodium citrate, sodium acetate, sodium lactate and trishydroxymethylaminomethane; and buffers such as citrate/dextrose, sodium carbonate, sodium bicarbonate and ammonium chloride. Such acids, bases and buffers are included in an amount required to maintain pH of the composition in an acceptable range.

In one embodiment, liquid pharmaceutical compositions also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In one embodiment, pharmaceutical compositions also include one or more preservatives to inhibit microbial activity.

Still other compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other compositions include one or more antioxidants to enhance chemical stability where required. Suitable antioxidants include, by way of example only, ascorbic acid, tocopherol, and sodium metabisulfite.

In one embodiment, aqueous compositions are packaged in single-dose non-reclosable containers. Alternatively, multiple-dose reclosable containers are used, in which case it is typical to include a preservative in the composition.

In some embodiments, aqueous pharmaceutical compositions do not include a preservative and are used within 24 hours of preparation.

In some embodiments, aqueous pharmaceutical compositions include one or more solubilizers which aid in enhancing the bioavailability of the active pharmaceutical ingredient. In some embodiments, the solubilizer is selected from Labrasol, Lutrol (macrogels, poloxamers), and others known in the art.

The oral pharmaceutical solutions described herein are beneficial for the administration to infants (less than 2 years old), children under 10 years of age and any patient group that is unable to swallow or ingest solid oral dosage forms.

For buccal or sublingual administration, in one embodiment, the compositions take the form of tablets, lozenges, or gels formulated in a conventional manner (see e.g. U.S. Pat. Nos. 4,229,447, 4,596,795, 4,755,386, and 5,739,136).

In one embodiment, dragee cores are prepared with suitable coatings. For this purpose, concentrated sugar solutions are used, which optionally contain gum arabic, talc, polyvinylpyrrolidone, carbopol gel, polyethylene glycol, and/or titanium dioxide, lacquer solutions, and suitable organic solvents or solvent mixtures. In one embodiment, dyestuffs or pigments are added to the tablets or dragee coatings for identification or to characterize different combinations of active compound doses.

It should be understood that many carriers and excipients may serve several functions, even within the same formulation.

In some embodiments, Compound 1, or a pharmaceutically acceptable salt thereof (e.g. Compound 2) is formulated in the form of a pharmaceutical composition that is suitable for inhalation/nasal delivery. In some embodiments, the pharmaceutical composition is in the form of a solution, suspension, emulsion, colloidal dispersion, spray, dry powder, aerosol, or combinations thereof. In some embodiments, the pharmaceutical composition comprises at least one pharmaceutically acceptable excipient that is commonly used in nasal/inhalable pharmaceutical compositions. In some embodiments, the pharmaceutical composition is administered with an atomizer, an insufflator, a nebulizer, a vaporizer, or a metered dose inhaler. In some embodiments, the pharmaceutical composition is inhaled nasally or orally. In some embodiments, crystalline Compound 1 is used in the pharmaceutical composition. In some embodiments, crystalline Compound 2 is used in the pharmaceutical composition. In some embodiments, amorphous Compound 1 is used in the pharmaceutical composition. In some embodiments, amorphous Compound 2 is used in the pharmaceutical composition.

Representative nasal/inhalation formulations are described in, for example, Ansel, H. C. et al., Pharmaceutical Dosage Forms and Drug Delivery Systems, Sixth Ed. (1995); REMINGTON: THE SCIENCE AND PRACTICE OF PHARMACY, 21st edition, 2005.

In some embodiments, Compound 1, or a pharmaceutically acceptable salt thereof (e.g. Compound 2) is formulated in the form of a nasal spray, nasal mist, and the like.

For administration by inhalation, Compound 1, or a pharmaceutically acceptable salt thereof (e.g. Compound 2) is formulated for use as an aerosol, a mist or a powder.

In some embodiments, pharmaceutical compositions suitable for nasal/inhalation administration are conveniently delivered in the form of an aerosol spray presentation from pressurized packs or a nebuliser, with the use of a suitable propellant. Capsules and cartridges for use in an inhaler or insufflator may be formulated containing a powder mix of the compound described herein and a suitable powder base such as lactose or starch.

In some embodiments, the pharmaceutical composition is in the form of a powder for nasal/inhalation delivery to a mammal. In some embodiments, powders comprise micronized and/or nano-sized particles of Compound 1, or a pharmaceutically acceptable salt thereof (e.g. Compound 2), blended with larger carrier particles that prevent aggregation. For example, in one embodiment a dry powder formulation is prepared as follows: Compound 1 or a pharmaceutically acceptable salt thereof (e.g. Compound 2) is jet milled. Lactose is jet milled and the two ingredients are mixed and the final mixture is packaged in sterile insufflators. In some instances powder inhalable formulations described herein comprise crystalline particles of Compound 1. In some instances powder inhalable formulations described herein comprise crystalline particles of Compound 2. In some embodiments, powder inhalable formulations described herein comprise amorphous particles of Compound 1. In some embodiments, powder inhalable formulations described herein comprise amorphous particles of Compound 2.

Dose Amounts

In certain embodiments, the effective amount of Compound 1, or a pharmaceutically acceptable salt thereof (e.g. Compound 2) is about 0.3 mg to about 1.5 g per dose, 0.3 mg to about 1 g per dose, about 1 mg to about 1 g per dose, about 5 mg to about 600 mg per dose or about 5 mg to about 500 mg per dose. In some embodiments, the effective amount of Compound 1, or a pharmaceutically acceptable salt thereof (e.g. Compound 2) is about 1 mg to about 5 g per day, about 5 mg to about 2 g per day, about 5 mg to about 1 g per day, about 5 mg to about 0.6 g per day, or about 5 mg to about 0.5 g per day.

In one embodiment, the effective amount of Compound 1, or a pharmaceutically acceptable salt thereof (e.g. Compound 2) is about 1 mg per dose, about 5 mg per dose, about 10 mg per dose, about 15 mg per dose, about 30 mg per dose, about 45 mg per dose, about 60 mg per dose, about 100 mg per dose, about 150 mg per dose, about 200 mg per dose, about 300 mg per dose, about 400 mg per dose, about 500 mg per dose, about 600 mg per dose, or about 1000 mg per dose.

In some embodiments, oral pharmaceutical solutions include about 0.015 mg/ml to about 20 mg/ml of Compound 2. In some embodiments, oral pharmaceutical solutions include about 1 mg/ml to about 20 mg/ml of Compound 2.

In one aspect, immediate release tablets include about 5% w/w to about 50% w/w of Compound 1, or a pharmaceutically acceptable salt thereof (e.g. Compound 2). In some embodiments, immediate release tablets include about 5% w/w to about 40% w/w, or about 5% w/w to about 30% w/w of Compound 1, or a pharmaceutically acceptable salt thereof (e.g. Compound 2). In some embodiments, immediate release tablets include about 5% w/w, about 10% w/w, about 15% w/w, about 20% w/w, about 25% w/w, about 30% w/w, about 33% w/w, about 35% w/w, about 40% w/w of Compound 1, or a pharmaceutically acceptable salt thereof (e.g. Compound 2).

In one aspect, immediate release capsules include about 1.25% w/w to about 50% w/w of Compound 1, or a pharmaceutically acceptable salt thereof (e.g. Compound 2). In some embodiments, immediate release capsules include Compound 1, or a pharmaceutically acceptable salt thereof (e.g. Compound 2) and the capsule shell only.

Methods of Dosing and Treatment Regimens

In one embodiment, the pharmaceutical compositions including Compound 1, or a pharmaceutically acceptable salt thereof (e.g. Compound 2), described herein is administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, compositions containing Compound 1, or a pharmaceutically acceptable salt thereof (e.g. Compound 2), described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compounds, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, Compound 1, or a pharmaceutically acceptable salt thereof (e.g. Compound 2) has a long lasting effect in mammals. In some embodiments, the long lasting effect of Compound 1, or a pharmaceutically acceptable salt thereof (e.g. Compound 2) is a result of the effect of the compound on apoptosis of Th2 cells.

In some embodiments, Compound 1, or a pharmaceutically acceptable salt thereof (e.g. Compound 2) is administered to a mammal with the following treatment cycle: (a) a first period during which Compound 1, or a pharmaceutically acceptable salt thereof (e.g. Compound 2) is administered to the mammal; and (b) a second period of at least seven days during which the Compound 1, or a pharmaceutically acceptable salt thereof (e.g. Compound 2) is administered to the mammal in a reduced amount. In some embodiments, the mammal is experiencing at least one symptom of an allergic disease or condition. In further embodiments, the allergic disease or condition is induced by the presence of an allergen. In yet further embodiments, the allergen is presented or suspected to be present during the treatment period. In some embodiments, the first period includes 1 to 10 days. In some embodiments, the first period comprises daily administration of Compound 1, or a pharmaceutically acceptable salt thereof (e.g. Compound 2). In some embodiments, the first period comprises once a day administration Compound 1, or a pharmaceutically acceptable salt thereof (e.g. Compound 2). In some embodiments, the first period comprises twice a day administration Compound 1, or a pharmaceutically acceptable salt thereof (e.g. Compound 2). In some embodiments, the second period includes at least 2 days. In some embodiments, the second period includes at least 7 days, at least 14 days, at least 21 days or at least 28 days. In some embodiments, the daily amount of Compound 1, or a pharmaceutically acceptable salt thereof (e.g. Compound 2) that is administered in the second period is reduced by at least 50% as compared to the first period. In some embodiments, the administration of Compound 1, or a pharmaceutically acceptable salt thereof (e.g. Compound 2) is discontinued in the second period.

In some embodiments, the treatment cycle is used once. In other embodiments, the treatment cycle is repeated until treatment is no longer needed.

In some embodiments, the compounds, compositions or therapies described herein are administered in at least one priming dose, followed by at least one maintenance dose. In certain embodiments, a priming dose of the agent(s) is administered until the symptoms of the disorder, disease or condition treated have been reduced (e.g., to a satisfactory level). Upon reduction, a maintenance dose of the compounds, compositions or therapies described herein is administered if desired or if necessary. In some embodiments, the maintenance dose comprises administration of the agent(s) described herein in an amount sufficient to at least partially maintain the reduction achieved by administration of the priming dose. In various embodiments, the maintenance dose, compared to the priming dose, includes a decrease in dosage and/or frequency of administration of the agent or one or more of the agents administered in the method. In certain embodiments, however, intermittent treatment with increased frequency and/or dosage amounts may be necessary upon any recurrence of symptoms.

In certain embodiments, the amount of a given agent that corresponds to a priming or maintenance amount varies depending upon factors including, by way of non-limiting example, the specific agent(s) utilized, the disease condition and its severity, the identity (e.g., weight) of the subject or host in need of treatment, and/or the route of administration. In various embodiments, the desired dose is conveniently presented in a single dose or in divided doses administered simultaneously (or over a short period of time) or at appropriate intervals, for example as two, three, four or more sub-doses per day.

Pharmacokinetic and Pharmacodynamic Analysis

In one embodiment, any standard pharmacokinetic protocol is used to determine blood plasma concentration profile in humans following administration of a formulation described herein (that include Compound 1, or a pharmaceutically acceptable salt thereof (e.g. Compound 2)). For example, a randomized single-dose crossover study is performed using a group of healthy adult human subjects. The number of subjects is sufficient to provide adequate control of variation in a statistical analysis, and is typically about 10 or greater, although for certain purposes a smaller group suffices. Each subject receives administration at time zero a single dose of a formulation of Compound 1, or a pharmaceutically acceptable salt thereof (e.g. Compound 2) (e.g., a dose containing about 0.3 mg, about 3 mg, about 5 mg, about 10 mg, about 15 mg, about 30 mg, about 50 mg, about 100 mg, about 150 mg, about 300 mg, or about 500 mg of Compound 1, or a pharmaceutically acceptable salt thereof (e.g. Compound 2)), normally at around 8 am following an overnight fast. The subjects continue to fast and remain in an upright position for about 2 hours after administration of the formulation. Blood samples are collected from each subject prior to administration (e.g., 15 minutes) and at several intervals after administration. In certain instances, several samples are taken within the first hour and taken less frequently thereafter. Illustratively, blood samples are collected at 0 (pre-dose), 0.25, 0.5, 1, 2, 3, 4, 6, 8, 12, and 16 hours after administration and, 24, 36, 48, 60 and 72 hours after administration. If the same subjects are to be used for study of a second test formulation, a period of at least 10 days should elapse before administration of the second formulation. Plasma is separated from the blood samples by centrifugation and the separated plasma is analyzed for Compound 1 by a validated high performance liquid chromatography/tandem weight spectrometry (LC/APCI-MS/MS) procedure such as, for example, Ramu et al., *Journal of Chromatography B*, 751 (2001) 49-59).

Any formulation giving the desired pharmacokinetic profile is suitable for administration according to the present methods.

Pharmacodynamic effects following administration of Compound 1, or a pharmaceutically acceptable salt thereof (e.g. Compound 2) can be assessed by a variety of methods. In some embodiments, the $PGD_2$-induced eosinophil shape change (ESC) in human whole blood is used as a pharmacodymanic marker. $DP_2$ is highly expressed on eosinophils, Th2 cells and basophils and has been shown to mediate a proinflammatory and chemotactic effect of $PGD_2$ on these cells. Compounds which antagonize the binding of $PGD_2$ are expected to inhibit the chemotactic and proinflammatory responses induced by $PGD_2$. Blood is collected from the subjects prior to dosing and at various time intervals after dosing. $PGD_2$ is added to the blood, and the blood sample is processed for evaluation of eosinophil shape change by measuring forward scatter using flow cytometry. The inhibition of eosinophil shape change relates to the blood concentration of Compound 1, providing a pharmacodynamic assessment for Compound 1, or a pharmaceutically acceptable salt thereof (e.g. Compound 2), following oral administration.

In some embodiments, pharmacodynamic effects are assessed by allergen skin prick tests. In some embodiments, assessment of pharmacodynamic effects is performed in a Vienna Challenge Chamber experiment in which patients carry out self-assessment and scoring of their symptoms on a scale of 0 to 3. Separate scores may be given for eye symptoms, nasal symptoms (including nasal obstruction, nasal itch, sneeze and rhinorrhea) and other symptoms. Although the symptom score for each patient is subjective, if a sufficient number of patients is used, the total scores are meaningful.

In some embodiments, asthma symptoms are quantified using measurements of lung function such as forced expiratory volume in one second (FEV1) or peak expiratory flow rate (PEF) or using the Juniper quality of life scale.

In some embodiments, the severity of atopic dermatitis symptoms are assessed using the scoring atopic dermatitis (SCORAD) or six area six sign atopic dermatitis (SASSAD) systems.

Combination Therapies

In certain instances, it is appropriate to administer Compound 1, or a pharmaceutically acceptable salt thereof (e.g. Compound 2) in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, the compounds are administered concurrently (e.g., simultaneously, essentially simultaneously or within the same treatment protocol) or sequentially, depending upon the nature of the disease, the condition of the patient, and the actual choice of compounds used. In certain embodiments, the determination of the order of administration, and the number of repetitions of administration of each therapeutic agent during a treatment protocol, is based upon evaluation of the disease being treated and the condition of the patient.

Contemplated pharmaceutical compositions provide a therapeutically effective amount of Compound 1, or a pharmaceutically acceptable salt thereof (e.g. Compound 2) enabling, for example, once-a-day, twice-a-day, three times a day, etc. administration. In one aspect, pharmaceutical compositions provide an effective amount of Compound 1, or a pharmaceutically acceptable salt thereof (e.g. Compound 2) enabling once-a-day dosing.

In specific embodiments, in a treatment for asthma involving administration of Compound 1, or a pharmaceutically acceptable salt thereof (e.g. Compound 2), increased therapeutic benefit results by also providing the patient with other therapeutic agents or therapies for asthma. In various embodiments, administration to an individual of Compound 1, or a pharmaceutically acceptable salt thereof (e.g. Compound 2) in combination with a second agent provides the individual with, e.g., an additive or synergistic benefit.

Therapeutically-effective dosages vary when the drugs are used in treatment combinations. Determination of therapeutically-effective dosages of drugs and other agents when used in combination treatment regimens is achieved in any manner. For example, the use of metronomic dosing, i.e., providing more frequent, lower doses in order to minimize toxic side effects can be utilized. In certain instances, the combination therapy allows for either or both of the Compound 1, or a pharmaceutically acceptable salt thereof (e.g. Compound 2) and the second agent to have a therapeutically effective amount that is lower than would be obtained when administering either agent alone.

A combination treatment regimen encompasses, by way of non-limiting example, treatment regimens in which administration of Compound 1, or a pharmaceutically acceptable salt thereof (e.g. Compound 2) is initiated prior to, during, or after treatment with a second agent, and continues until any time during treatment with the second agent or after termination of treatment with the second agent. It also includes treatments in which Compound 1, or a pharmaceutically acceptable salt thereof (e.g. Compound 2) and the second agent being used in combination are administered simultaneously or at different times and/or at decreasing or increasing intervals during the treatment period. Combination treatment further includes periodic treatments that start and stop at various times to assist with the clinical management of the patient.

In some embodiments, combination therapies described herein are used as part of a specific treatment regimen intended to provide a beneficial effect from the co-action of a DP2 antagonist, e.g Compound 1, or a pharmaceutically acceptable salt thereof (e.g. Compound 2), and a concurrent treatment. It is understood that in certain embodiments, the dosage regimen to treat, prevent, or ameliorate the condition (s) for which relief is sought, is modified, in one embodiment, in accordance with a variety of factors. These factors include, by way of non-limiting example, the type of disease or condition being from which the subject suffers, as well as the age, weight, sex, diet, and/or medical condition of the subject. Thus, in some embodiments, the dosage regimen employed, varies and/or deviates from the dosage regimens set forth herein.

In some embodiments, provided herein are compositions, and methods of administering compositions comprising Compound 1, or a pharmaceutically acceptable salt thereof (e.g. Compound 2) in combination with an therapeutic agent selected from: 5-lipoxygenase-activating protein inhibitors, 5-lipoxygenase inhibitors, CYSLTR1 antagonists, CYSLTR2 antagonists, LTA$_4$H inhibitors, BLT1 antagonists, BLT2 antagonists, thromboxane antagonists, DP1 receptor antagonists, DP1 receptor agonists, IP receptor agonists, anti-IgE, chemokine receptor antagonists, IL5 antibody, bronchodilators, theophylline, leukotriene receptor antagonists, leukotriene formation inhibitors, decongestants, antihistamines, mucolytics, corticosteroids, glucocorticoids, anticholinergics, antitussives, analgesics, expectorants, and β-2 agonists.

In some embodiments, provided herein are compositions, and methods of administering compositions comprising Compound 1, or a pharmaceutically acceptable salt thereof (e.g. Compound 2) in combination with a therapeutic agent useful for treating respiratory conditions. Therapeutic agents useful for treating respiratory conditions and disorders, include: glucocorticoids; leukotriene modifiers; mast cell stabilizers; antimuscarinics/anticholinergics; methylxanthines; antihistamines; omalizumab, olapatidine and azelastine; an IgE blocker; beta2-adrenergic receptor agonists, such as: short acting beta2-adrenergic receptor agonists, and long-acting beta2-adrenergic receptor agonists.

In some embodiments, Compound 1, or a pharmaceutically acceptable salt thereof (e.g. Compound 2) is used in combination with one or more other therapeutic agents selected from anti-inflammatory agents, anticholinergic agents (particularly an $M_1/M_2/M_3$ receptor antagonist), β₂-adrenoreceptor agonists, antiinfective agents, antihistamines, PDE-4 inhibitors, H1 antagonist, H3 antagonist (and/or inverse agonist), H1/H3 dual antagonist (and/or inverse agonist), PDE4 inhibitor, β₂-adrenoreceptor agonist, corticosteroid, non-steroidal GR agonist, anticholinergic, antihistamine, leukotriene receptor antagonists, a $CysLT_1$ receptor antagonist, dual $CysLT_1/CysLT_2$ receptor antagonist, NSAIDs and NO-donors or NSAIDs and proton-pump inhibitors, inhibitors of UDP-glucuronosyltransferase (UGT).

In some embodiments, the other therapeutic ingredient(s) are used in the form of salts (e.g. as alkali metal or amine salts or as acid addition salts), or prodrugs (including esters (e.g. alkyl esters)), or as solvates, (e.g. hydrates). In one aspect, if appropriate, the therapeutic ingredients will be used in optically pure form or in racemic form.

The individual compounds of such combinations are administered either sequentially or simultaneously in separate or combined pharmaceutical formulations.

In one aspect, Compound 1, or a pharmaceutically acceptable salt thereof (e.g. Compound 2) is combined with or administered in combination with: one or more agents used to treat used to treat asthma (including, but not limited to: combination Inhalers; inhaled Beta-2 agonists; inhaled corticosteroids; leukotriene modifiers; mast cell stabilizers; monoclonal antibodies; oral Beta-2 agonists; bronchodilator); one or more agents used to treat allergy (including, but not limited to: antihistamine and decongestant combinations; antihistamines; decongestants; leukotriene modifiers; nasal anticholinergics; nasal corticosteroids; nasal decongestants; nasal mast cell stabilizers); one or more agents used to treat chronic obstructive pulmonary disease (COPD) (including, but not limited to: anticholinergics; combination Inhalers; corticosteroids; inhaled Beta-2 Agonists; inhaled Corticosteroids; mukolytics; oral Beta-2 agonists; bronchodilator).

In any of the compositions, combinations, methods of treating or combination methods of treating described herein Compound 2 is used. In any of the compositions, combinations, methods of treating or combination methods of treating described herein crystalline Compound 2 is used.

In any of the compositions, combinations, methods of treating or combination methods of treating described herein Compound 1 (free acid) is used.

In certain embodiments, co-administration of a UGT inhibitor allows for lower doses of Compound 1, or a pharmaceutically acceptable salt thereof (e.g. Compound 2) to be administered.

Therapeutic agents useful for treating respiratory conditions and disorders, include, by way of non-limiting example: glucocorticoids, such as, ciclesonide, beclomethasone dipropionate, budesonide, flunisolide, fluticasone propionate, fluticasone furoate, mometasone furoate, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamines, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, olapatidine and azelastine; an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, indacaterol and bambuterol.

In some embodiments, provided herein are combinations therapies that combine treatment with Compound 1, or a pharmaceutically acceptable salt thereof (e.g. Compound 2), with treatment with an inhibitor of leukotriene synthesis or with a leukotriene receptor antagonist.

In some embodiments, the second therapeutic agent is a FLAP inhibitor compound. In some embodiments, the FLAP inhibitor is selected from compounds described in U.S. patent application Ser. No. 11/538,762 (issued as U.S. Pat. No. 7,405,302); U.S. patent application Ser. No. 12/131,828; U.S. patent application Ser. No. 11/553,946 (published as 2007/0105866); U.S. patent application Ser. No. 11/925,841; U.S. patent application Ser. No. 12/089,706; U.S. patent application Ser. No. 12/089,707; U.S. patent application Ser. No. 12/092,570; U.S. patent application Ser. No. 11/744,555 (published as 2007/0219206); U.S. patent application Ser. No. 11/746,010 (published as 2007/0225285); U.S. patent application Ser. No. 11/745,387 (published as 2007/0244128); U.S. patent application Ser. No. 12/257,876; U.S. patent application No. 61/055,887; U.S. patent application No. 61/055,899; International Patent Application no. PCT/US07/86188; WO 07/047,207; WO07/056,021; WO07/056,220; WO07/056,228; International Patent Application no. PCT/US08/62310; International Patent Application no. PCT/US08/062,793; International Patent Application no. PCT/US08/62580; International Patent Application no. PCT/US2008/052960; International Patent Application no. PCT/US08/81190; International Patent Application no. PCT/US08/76225; each of which is herein incorporated by reference in its entirety.

In some embodiments, the second therapeutic agent is a FLAP inhibitor that is selected from: MK886 (also known as 3-[3-tert-butylsulfanyl-1-(4-chloro-benzyl)-5-isopropyl-1H-indol-2-yl]-2,2-dimethyl-propionic acid); MK591 (also known as 3-[3-tert-butylsulfanyl-1-(4-chloro-benzyl)-5-(quinolin-2-ylmethoxy)-1H-indol-2-yl]-2,2-dimethyl-propionic acid); and DG031 (also known as BAY X1005; cyclopentyl[4-(quinolin-2-ylmethoxy)-phenyl]-acetic acid), (3-[3-tert-Butylsulfanyl-1-[4-(5-methoxy-pyrimidin-2-yl)-benzyl]-5-(5-methyl-pyridin-2-ylmethoxy)-1H-indol-2-yl]-2,2-dimethyl-propionic acid); (3-[3-tert-Butylsulfanyl-1-[4-(5-methoxy-pyrimidin-2-yl)-benzyl]-5-(5-methyl-pyrazin-2-ylmethoxy)-1H-indol-2-yl]-2,2-dimethyl-propionic acid); (3-{5-((S)-1-Acetyl-2,3-dihydro-1H-indol-2-ylmethoxy)-3-tert-butylsulfanyl-1-[4-(5-methoxy-pyrimidin-2-yl)-benzyl]-1H-indol-2-yl}-2,2-dimethyl-propionic acid); (3-[3-tert-Butylsulfanyl-1-[4-(6-methoxy-pyridin-3-yl)-benzyl]-5-(pyridin-2-ylmethoxy)-1H-indol-2-yl]-2,2-dimethyl-propionic acid); (3-[3-tert-Butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid); (3-[3-tert-Butylsulfanyl-1-[4-(5-fluoro-pyridin-2-yl)-benzyl]-5-(quinolin-2-ylmethoxy)-1H-indol-2-yl]-2,2-dimethyl-propionic acid); (2-[3-tert-Butylsulfanyl-1-[4-(5-methoxy-pyrimidin-2-yl)-benzyl]-5-(5-methyl-pyridin-2-ylmethoxy)-1H-indol-2-ylmethyl]-2-ethyl-butyric acid); (3-[3-tert-Butylsulfanyl-1-[4-(6-methoxy-pyridin-3-yl)-benzyl]-5-(5-methyl-pyridin-2-ylmethoxy)-1H-indol-2-yl]-2,2-dimethyl-propionic acid); (3-[5-((S)-1-Acetyl-pyrrolidin-2-ylmethoxy)-3-tert-butylsulfanyl-1-(4-chloro-benzyl)-1H- indol-2-yl]-2,2-dimethyl-propionic acid); (3-[3-tert-butyl-sulfanyl-1-[4-(5-fluoro-pyridin-2-yl)-benzyl]-5-(pyridin-2-ylmethoxy)-1H-indol-2-yl]-2,2-dimethyl-propionic acid), (3-{5-((S)-1-Acetyl-2,3-dihydro-1H-indol-2-ylmethoxy)-3-tert-butylsulfanyl-1-[4-(5-ethoxy-pyrimidin-2-yl)-benzyl]-1H-indol-2-yl}-2,2-dimethyl-propionic acid), or pharmaceutically acceptable salt or N-oxide thereof.

In some embodiments, the FLAP inhibitor is selected from compounds described in U.S. Pat. Nos. 4,929,626; 4,970,215; 5,081,138; 5,095,031; 5,204,344; 5,126,354; 5,221,678; 5,229,516; 5,272,145; 5,283,252; 5,288,743; 5,292,769; 5,304,563; 5,399,699; 5,459,150; 5,512,581; 5,597,833; 5,668,146; 5,668,150; 5,691,351; 5,714,488; 5,783,586; 5,795,900; and 5,843,968, each of which is herein incorporated by reference for the disclosure of such FLAP inhibitors).

In some embodiments described herein, Compound 1, or a pharmaceutically acceptable salt thereof (e.g. Compound 2) is used in combination with leukotriene receptor antagonists including, but are not limited to, $CysLT_1/CysLT_2$ dual receptor antagonists, and $CysLT_1$ receptor antagonists. $CysLT_1$ receptor antagonists include, but are not limited to, zafirlukast, montelukast, prankulast, and derivatives or analogs thereof. In one embodiment, such combinations are used to treat respiratory disorders.

In additional embodiments, provided herein are therapies which combine administration of Compound 1, or a pharmaceutically acceptable salt thereof (e.g. Compound 2) with the administration of an anti-inflammatory agent. In specific embodiments, such therapies are used in the treatment of prostaglandin $D_2$-dependent or prostaglandin $D_2$-mediated diseases or conditions.

In certain aspects, Compound 1, or a pharmaceutically acceptable salt thereof (e.g. Compound 2) is combined with or administered in combination with one or more agents used to treat used to treat asthma, including, but not limited to: combination Inhalers (fluticasone propionate and salmeterol xinafoate, budesonide and formoterol fumarate and indacaterol and mometasone furoate); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, Compound 1, or a pharmaceutically acceptable salt thereof (e.g. Compound 2) is combined with or administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, Compound 1 or a pharmaceutically acceptable salt thereof (e.g. Compound 2) is combined with or administered in combination with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one aspect, Compound 1, or a pharmaceutically acceptable salt thereof (e.g. Compound 2) is used in combination with one or more other therapeutic agents or the pharmaceutical compositions of Compound 1, or a pharmaceutically acceptable salt thereof (e.g. Compound 2) include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, or antihistamines. In one case, antiinfective agents include antibiotics and/or antivirals. In a further aspect, a combination comprising Compound 1, or a pharmaceutically acceptable salt thereof (e.g. Compound 2) includes one or more other therapeutically active agent, where the one or more other therapeutically active agents are selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment encompasses combinations comprising Compound 1, or a pharmaceutically acceptable salt thereof (e.g. Compound 2) together with a $\beta_2$-adrenoreceptor agonist, and/or an anticholinergic, and/or a PDE-4 inhibitor, and/or an antihistamine. Another embodiment encompasses combinations comprising Compound 1, or a pharmaceutically acceptable salt thereof (e.g. Compound 2) together with a corticosteroid or NSAID.

In some embodiments, the other therapeutic ingredient(s) will be used in the form of salts (e.g. as alkali metal or amine salts or as acid addition salts), or prodrugs (such as esters (e.g. alkyl esters)), or as solvates (e.g. hydrates). In one aspect, if appropriate, the therapeutic ingredients will be used in optically pure form. In another aspect, if appropriate, the therapeutic ingredients will be used in racemic form.

Examples of $\beta_2$-adrenoreceptor agonists include salmeterol (as a racemate or a single enantiomer such as the R-enantiomer), salbutamol (as a racemate or a single enantiomer such as the R-enantiomer), formoterol (as a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer.

In one embodiment, Compound 1, or a pharmaceutically acceptable salt thereof (e.g. Compound 2) is combined with or administered in combination with a phosphodiesterase 4 (PDE4) inhibitor, especially in the case of a formulation adapted for inhalation. The PDE4-specific inhibitor useful in this aspect is any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide), oxitropium (for example, as the bromide) and tiotropium (for example, as the bromide). Also of interest are revatropate (for example, as the hydrobromide) and LAS-34273 which is disclosed in WO01/04118. Exemplary compounds for oral administration include pirenzepine, darifenacin (hydrobromide), oxybutynin, terodiline, tolterodine, tolterodine tartrate, otilonium (for example, as the bromide), trospium chloride, solifenacin, and solifenacin succinate.

In one embodiment, Compound 1, or a pharmaceutically acceptable salt thereof (e.g. Compound 2) is combined with or administered in combination with an H1 antagonist. Examples of H1 antagonists include, but are not limited to, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly azelastine, cetirizine, levocetirizine, efletirizine and fexofenadine.

In another embodiment, Compound 1, or a pharmaceutically acceptable salt thereof (e.g. Compound 2) is combined with or administered in combination with an H3 antagonist (and/or inverse agonist).

In another embodiment, Compound 1, or a pharmaceutically acceptable salt thereof (e.g. Compound 2) is combined with or administered in combination with an H1/H3 dual antagonist (and/or inverse agonist).

In another aspect, Compound 1, or a pharmaceutically acceptable salt thereof (e.g. Compound 2) is combined with or administered in combination with a PDE4 inhibitor.

In another aspect, Compound 1, or a pharmaceutically acceptable salt thereof (e.g. Compound 2) is combined with or administered in combination with a $\beta_2$-adrenoreceptor agonist.

In another aspect, Compound 1, or a pharmaceutically acceptable salt thereof (e.g. Compound 2) is combined with or administered in combination with a corticosteroid.

In another aspect, Compound 1, or a pharmaceutically acceptable salt thereof (e.g. Compound 2) is combined with or administered in combination with a non-steroidal GR agonist.

In another aspect, Compound 1, or a pharmaceutically acceptable salt thereof (e.g. Compound 2) is combined with or administered in combination with an anticholinergic.

In another aspect, Compound 1, or a pharmaceutically acceptable salt thereof (e.g. Compound 2) is combined with or administered in combination with an antihistamine.

In another aspect, Compound 1, or a pharmaceutically acceptable salt thereof (e.g. Compound 2) is combined with or administered in combination with a PDE4 inhibitor and a $\beta_2$-adrenoreceptor agonist.

In another aspect, Compound 1, or a pharmaceutically acceptable salt thereof (e.g. Compound 2) is combined with or administered in combination with an anticholinergic and a PDE-4 inhibitor.

In one embodiment, Compound 1, or a pharmaceutically acceptable salt thereof (e.g. Compound 2) is combined with or administered to a patient in combination with inhaled corticosteroids.

In one embodiment, Compound 1, or a pharmaceutically acceptable salt thereof (e.g. Compound 2) is combined with or administered to a patient in combination with beta2-adrenergic receptor agonists. In one embodiment, Compound 1, or a pharmaceutically acceptable salt thereof (e.g. Compound 2) is combined with or administered to a patient in combination with short acting beta2-adrenergic receptor agonists. In one embodiment, Compound 1, or a pharmaceutically acceptable salt thereof (e.g. Compound 2) is combined with or administered to a patient in combination with long-acting beta2-adrenergic receptor agonists.

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, parametasone, prednicarbate, prednisone/prednisolone, rimexolone, tixocortol, triamcinolone, and ulobetasol.

In one embodiment, Compound 1, or a pharmaceutically acceptable salt thereof (e.g. Compound 2) is combined with or administered in combination with one or more agents that are inhibitors of UDP-glucuronosyltransferase (UGT). UGT inhibitors include those described in U.S. 2003/0215462; U.S. 2004/0014648. In some embodiments, co-administration of a UGT inhibitor allows for lower doses of Compound 1, or a pharmaceutically acceptable salt thereof (e.g. Compound 2) to be administered.

The individual compounds of such combinations are administered either sequentially or simultaneously in separate or combined pharmaceutical formulations. In one embodiment, the individual compounds will be administered simultaneously in a combined pharmaceutical formulation. Appropriate doses of known therapeutic agents will be appreciated by those skilled in the art.

The combinations referred to herein are conveniently presented for use in the form of a pharmaceutical compositions together with a pharmaceutically acceptable diluent (s) or carrier(s).

A compound that is N-ethyl-2-(2'-((ethylamino)methyl)-6-methoxy-4'-(trifluoromethyl)biphenyl-3-yl)acetamide; 2-(2'-((ethylamino)methyl)-6-methoxy-4'-(trifluoromethyl) biphenyl-3-yl)acetic acid; ethyl 2-(2'-((ethylamino)methyl)-6-hydroxy-4'-(trifluoromethyl)biphenyl-3-yl)acetate; 2-(2'-((3-benzyl-1-methylureido)methyl)-6-methoxy-4'-(trifluoromethyl)biphenyl-3-yl)acetic acid; 3-(5'-(carboxymethyl)-2'-methoxy-4-(trifluoromethyl)biphenyl-2-yl)-2-(2'-((ethylamino)methyl)-6-methoxy-4'-(trifluoromethyl)biphenyl-3-yl)propanoic acid; 2,2'-(2',2'''-(ethylazanediyl)bis(methylene)bis(6-methoxy-4'-(trifluoromethyl)biphenyl-3,2'-diyl))diacetic acid; methyl 2-(2'-((3-benzyl-1-ethylureido)methyl)-6-methoxy-4'-(trifluoromethyl)biphenyl-3-yl)acetate; ethyl 2-(2'-((3-benzyl-1-ethylureido)methyl)-6-hydroxy-4'-(trifluoromethyl)biphenyl-3-yl)acetate; 2-(2'-((3-benzyl-1-ethylureido)methyl)-6-hydroxy-4'-(trifluoromethyl)biphenyl-3-yl)acetic acid; 2-(2'-((((5'-(2-(benzyloxy)-2-(methylamino)ethyl)-2'-methoxy-4-(trifluoromethyl)biphenyl-2-yl)methyl)(ethyl) amino)methyl)-6-methoxy-4'-(trifluoromethyl)biphenyl-3-yl)acetic acid; or (Z)-2-(2'-((3-benzyl-1-ethylureido) methyl)-6-methoxy-4'-(trifluoromethyl)biphenyl-3-yl)-3-(5'-(carboxymethyl)-2'-methoxy-4-(trifluoromethyl) biphenyl-2-yl)acrylic acid.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by antagonism of DP2 receptors.

For example, the container(s) include Compound 1, or a pharmaceutically acceptable salt thereof (e.g. Compound 2), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

It is to be understood that as used herein, pharmaceutical compositions described as comprising a pharmaceutically acceptable salt described herein, e.g., liquid solutions, encompass pharmaceutical compositions comprising the associated and/or disassociated forms of the salt. Thus, for example, a pharmaceutical composition described herein comprising an aqueous solution of Compound 2 encompasses a composition comprising a population of sodium cations and a population of 2-(3-(2-(((tert-butylthio)methyl)-4-(2,2-dimethyl-propionylamino)phenoxy)-4-methoxyphenyl)acetate anions.

EXAMPLES

The following ingredients, formulations, processes and procedures for practicing the methods disclosed herein correspond to that described above. The procedures below describe with particularity illustrative, non-limiting embodiment of formulations that include a Compound 1, or a pharmaceutically acceptable salt and/or solvate thereof, and pharmacokinetic profiles and pharmacodynamic effects thereof. By way of example only, Compound 1 is optionally prepared as outlined in U.S. patent application Ser. No. 12/497,343, or as outlined herein.

Example 1: Synthesis of Compound 1 and Salts of Compound 1 (e.g. Compound 2)

Preparation of methyl 2-(3-hydroxy-4-methoxyphenyl)acetate

Charged to a 2 L reaction flask, 300 g of 2-(3-hydroxy-4-methoxyphenyl) acetic acid and 900 mL of methanol. To the reaction solution was charged 6.4 mL of concentrated sulfuric acid. The reaction was heated at reflux for 3.5 hours. Upon completion of reaction, the reaction mixture was concentrated to ~600 g. 600 mL of methyl tert-butyl ether (MTBE) was added to the flask and concentrated to ~600 g. 600 mL of MTBE was added to the flask again and concentrated to ~600 g. 1.0 L of MTBE was then added to the flask and washed with 750 mL of saturated sodium bicarbonate, aqueous solution twice. The organics were dried over sodium sulfate and filtered. The filtrates were concentrated to an oil and dried under vacuum to a constant weight. Yield of 2-(3-hydroxy-4-methoxyphenyl)acetic acid methyl ester (301.8 grams; 93%; 99% pure as determined by liquid chromatography).

Purification of methyl
2-(3-hydroxy-4-methoxyphenyl)acetate

Loaded 22 g of methyl 2-(3-hydroxy-4-methoxyphenyl)acetate as an oil onto 110 g of Silica gel in 100 mL hexanes. 5 mL of dichloromethane was used to transfer all of the methyl 2-(3-hydroxy-4-methoxyphenyl)acetate. The plug was eluted with 500 mL 9; 1 hexanes:ethyl acetate followed by 200 mL 85:15 hexanes:ethyl acetate. The product was then collected eluting with 4.5 L 8:2 hexanes:ethyl acetate. All fractions were monitored by thin layer chromatograpgy (TLC: 1:1 hexanes:ethyl acetate) and stained in PMA Fractions containing product were combined and concentrated to oil and dried to a constant weight under high vacuum.

Step 1: Preparation of methyl 2-(3-(2-formyl-4-nitrophenoxy)-4-methoxyphenyl)acetate (Compound A)

Charged to a 12 L reactor, 199 g of 2-fluoro-5-nitrobenzaldehyde, 230.9 g of 2-(3-hydroxy-4-methoxyphenyl) acetic acid methyl ester, 1.15 L of dioxane and 325.3 g of potassium carbonate. The suspension was agitated and heated at 70° C. for 6 hours. Upon reaction completion, the reaction mixture was diluted with 5 volumes of dioxane and filtered at 40° C. The filter cake was washed with warm dioxane twice. The filtrates were slowly charged to a 10 volumes solution of 1:4 1N HCl: water end pH=2-3. The resulting suspension was then filtered and the filter cake was washed with 5 volumes water twice. The resulting white solids are dried at 40° C.

Step 2: Preparation of methyl 2-(3-(2-hydroxymethyl-4-nitrophenoxy)-4-methoxyphenyl)acetate (Compound B)

Charged to a 5 L flask, 333.8 g of Compound A, 1.67 L of tetrahydrofuran (THF) and 1.67 L of dioxane. Charged, 2.74 g of sodium borohydride to the resulting suspension. The suspension was then cooled to 10° C. and held for 30 minutes before charging 2.74 g of sodium borohydride. Agitated for 30 minutes at 10° C. then charged 2.74 g of sodium borohydride. Agitated for 30 minutes at 10° C. then charged 2.74 g of sodium borohydride. Agitated for 6 hours at 10° C. Charged 2.74 g of sodium borohydride, agitated reaction mixture overnight at room temperature. Quenched reaction by charging 519 mL 1N HCl until pH=2. Charged 3.47 L of ethyl acetate and 1.62 L of water. Separated layers and washed organics with 1.62 L of 25% sodium chloride, aqueous solution. Separated layers and dried organics over sodium sulfate. The organics were concentrated to dryness on rotovaps under vacuum at temp <40° C. Compound B was further dried under high vacuum to obtain an orange oil. (Note: The reaction volumes should be increased from 10 volumes THF:Dioxane to 14 volumes of THF:Dioxane and the reaction should run at room temperature).

Step 3: Preparation of methyl 2-(3-(2-bromomethyl-4-nitrophenoxy)-4-methoxyphenyl)acetate (Compound C)

Slowly charged 153.6 mL of phosphorus tribromide to a solution of 377.2 g of Compound B and 1.50 L of 1,2-dimethoxyethane maintaining an internal temperature <25° C. Upon completion of addition, the reaction mixture was heated at 50° C. for 3 hours. Upon completion; the reaction was cooled to room temperature and 3.77 L of water was slowly added. The suspension was agitated for at least 1 hour and filtered. The solids were washed with 754 mL of water twice. The crude 385.5 g Compound C was triturated with 770 mL of MTBE and agitated for 2 hours. The suspension was filtered and the solids were dried under vacuum at 40° C. to a constant weight. Yield Compound C (355.1 grams; 90%; 96% pure by liquid chromatography)

Step 4: Preparation of methyl 2-(3-(2-(tert-butylthiomethyl)-4-nitrophenoxy)-4-methoxyphenyl)acetate (Compound D)

Charged to a 12 L reactor, 355 g of Compound C, 97.4 mL of 2-methyl-2-propanethiol, and 1.8 L of THF cooling the reaction mixture to 0° C. Charged 8.7 g of sodium hydride and held at <15° C. for 10 minutes. Charged, 8.7 g of sodium hydride and held at <15° C. for 10 minutes. Charged, 8.7 g of sodium hydride and held at <15° C. for 10 minutes. Charged, 8.7 g of sodium hydride and held at <15° C. for 2 hours. Charged, 4 mL of 2-methyl-2-propanethiol and 1.5 g of sodium hydride and held at <15° C. for 2.5 hours. Upon completion of the reaction, 7.0 L of water was slowly added maintaining an internal temperature below 22° C. The suspension was allowed to agitate overnight before filtering. The solids were washed with 1.0 L of water two times. The solids were dried to a constant weight under vacuum at 40° C. Yield Compound D (363 grams; 100%; 95% pure by liquid chromatography).

Step 5: Preparation of methyl 2-(3-(4-amino-2-(tert-butylthiomethyl)phenoxy)-4-methoxyphenyl)acetate (Compound E)

Charged to a 12 L flask, 355 g of Compound D, 1.8 L of methanol, 500 mL of 1,1-dimethylhydrazine and 89.5 g of DARCO and heated suspension to 65° C. Charged 6.75 g of ferric chloride and agitated for 1 hour. Charged 6.75 g of ferric chloride and agitated for 1 hour. Charged 6.75 g of ferric chloride and agitated for 1 hour. Charged 6.75 g of ferric chloride and agitated for 7 hours. Upon completion the reaction was cooled to room temperature and filtered through a pad of celite. The celite was washed with 1.0 L of methanol three times. The filtrates were concentrated to dryness to obtain thick oil. The oil was further dried under vacuum to a constant weight. Yield Compound E (381 grams; 116%; 94% pure by liquid chromatography)

Step 6: Preparation of methyl 2-(3-(2-(tert-butylthiomethyl)-4-pivalamidophenoxy)-4-methoxyphenyl) acetate (Compound F)

Charged to a 5 L flask, 329 g of Compound E and 1.4 L of dichloromethane (DCM). To the solution charged, 199 mL of triethylamine and cooled to 15° C. Charged 156 mL of pivaloyl chloride and heated to 40° C. Agitated at 40° C. for 1 hour. Upon completion the reaction mixture was cooled to 0° C. and quenched with 1.6 L of water. Charged 800 mL of DCM and separated the layers. The aqueous layers was re-extracted with 800 mL of DCM. The combined organics were washed with 1.3 L of saturated sodium bicarbonate solution. The organics were dried over sodium sulfate and filtered. The filtrates were concentrated to 885 g and 650 mL of heptane was then charged. Concentrated to 700 g and charged 650 mL of heptane. Concentrated to 600 g and charged 2.1 L of heptane and agitated the mixture for 15 hours. After 15 hours a large mass of solids had formed. The heptane was decanted off and the large solid was broken into smaller pieces. Charged 2 L of heptane and agitated for 5 hours. The suspension was filtered and the solids were washed with heptane. The solids were dried to a constant weight under vacuum at 40° C. Yield Compound F (341.8 grams; 85%; 90% pure by liquid chromatography).

Step 7: Preparation of 2-(3-(2-((tert-butylthio) methyl)-4-(2,2-dimethyl-propionylamino)phenoxy)-4-methoxyphenyl)acetic acid (Compound 1)

Charged 66.4 mL of 50% sodium hydroxide solution slowly to a solution of 299.3 g Compound F, 1.2 L of THF, and 900 mL of methanol; maintaining an internal temperature of <25° C. The reaction mixture agitated at room temperature for 3 hours. 2150 g of reaction mixture was concentrated to 600 g and 2.2 L of water was charged. The aqueous solution was washed with 900 mL of MTBE and repeated for a total of four times. Charged to the aqueous layer containing Compound 1930 mL of ethanol and cooled the solution to 10° C. While maintaining an internal temperature of 10° C. 300 mL of 4M HCl was added slowly until pH=2-3. The oily suspension was allowed to agitate at room temperature for no less than 5 hours before filtering the resulting suspension. The solids were washed with 600 mL of water twice and dried under high vacuum at 40° C. for 72 hours obtain a constant weight. Yield Compound 1 (279 grams; 96%; 98.2% pure by liquid chromatography). (Note: During the addition of 50% NaOH, the reaction mixture should be cooled to <10° C. to avoid the formation of a particular impurity with a relative retention time of 0.68. Upon completion of the addition, the reaction mixture should agitate at room temperature).

Removal of Residual Solvents from Compound 1

Charged 410 mL of ethyl acetate to 82.8 g Compound 1 and heated the suspension to reflux to obtain a solution. Charged 410 mL of heptane slowly until a hazy solution formed which was then heated at reflux until a clear solution was obtained. The solution was allowed to cool to room temperature and further cooled to 0° C. The suspension was filtered and a minimum amount of heptane was used for transferring. The solids were dried to a constant weight under high vacuum at 40° C. XRPD of the solids showed it to be Pattern 1 of Compound 1.

Step 8: Preparation of 2-(3-(2-((tert-butylthio) methyl)-4-(2,2-dimethyl-propionylamino)phenoxy)-4-methoxyphenyl)acetic acid sodium salt (Compound 2)

Charged to the 3 L flask 277.6 g of Compound 1, 833 mL of methanol and 416 mL of THF. The resulting solution was cooled to 10° C. and 25.6 mL of 50% NaOH (0.80 eq) was added slowly. Agitated at room temperature for at least 1 hour before measuring the pH. Reaction is complete when the ~pH=8.9. pH=6.7 was measured. Charged another 0.10 equivalent 3.15 mL 50% NaOH and agitated for 40 minutes. pH=6.8. Charged another 0.05 equivalent, 1.58 mL 50% NaOH and agitated for 30 minutes. pH=8.0. Charged another 0.015 equivalent, 0.50 mL 50% NaOH and agitated for 30 minutes. pH=9.12. Reaction complete after (0.965 equivalent 50% NaOH), concentrated the solution to 450 g. Charged 1.1 L of MTBE and concentrated to 400 g. Charged 1.1 L of MTBE and concentrated to 500 g. Charged 1.1 L of MTBE and concentrated to 400 g. Slowly charged 1.6 L of heptane and agitated for 5 hours. No solids precipitated, concentrated the gummy material to dryness. Dissolved 331 g of Compound 2 in 2.65 L MTBE at reflux. Concentrated the solution to 1860 g and slowly added it dropwise to 19.8 L heptane. Agitated the suspension overnight. The resulting suspension was filtered and dried to a constant weight at 40° C. Yield of Compound 2 (262 grams; 90%; 97% pure by liquid chromatography).

Preparation of Crystalline 2-(3-(2-((tert-butylthio) methyl)-4-(2,2-dimethyl-propionylamino)phenoxy)-4-methoxyphenyl)acetic acid Sodium Salt (Crystalline Compound 2)

Charged to the 12 L flask 260.6 g of Compound 2 (amorphous) and 782 mL of acetone. The resulting mixture was heated to 40° C. to form a solution. Charged to the solution, 1.30 L of heptane slowly through an addition funnel over 35 minutes. The cloudy mixture was heated to reflux until a clear solution was obtained. The solution was allowed to cool to room temperature and agitated for 72 hours. Charged to the suspension, 2.6 L of heptane and continued agitating for 24 hours. The suspension was filtered and the solids were washed with 1.0 L of heptane. The isolated solids were dried at 60° C. under high vacuum for 24 hours. Residual solvent data showed high levels of acetone. The isolated Compound 2 was further dried at 60° C. under high vacuum for 12 days. Yield of Compound 2 (242.5 grams; 93%; 96.8% pure by liquid chromatography). Salts of Compound 1

Salt formation experiments were carried out in 3 solvents (THF, IPA and ACN) using 5 bases. The experimental procedure used was: 50 mg of Compound 1 (free acid) was weighted into 2 cm³ vials and 10 vol (500 µl) of THF, IPA or ACN was added to obtain a homogeneous solution. At ambient, 1 equivalent of the appropriate aqueous solution of base was added in each vial. The clear solutions were cooled at 4° C., if no precipitate was obtained, the samples were cooled further to −20° C. prior to slow evaporation at ambient. The suspensions were subjected to a series of heat/cool cycles from RT to 50° C. (8 hour cycles) for 8 days.

KOH was used to form the potassium salt of Compound 1.

NaOH was used to form the sodium salt of Compound 1.

L-Arginine was used to form the L-Arginine salt of Compound 1.

L-Lysine was used to form the L-Lysine salt of Compound 1.

N-methylglucamine was used to form the N-methylglucamine salt of Compound 1.

No crystalline salt was obtained after maturation and cooling. The solids filtered from the samples containing KOH and NaOH were amorphous after 5 days of maturation. Only glassy materials were obtained after solvent evaporation at RT and no sign of crystallisation was observed under polarised light for any of the samples.

Example 2: Crystallisation Study of Compound 1 and Compound 2

An investigation into the propensity for Compound 1 and Compound 2 to crystallise and/or to form polymorphs, solvates and hydrates was carried out using a variety of procedures, as follows: partially crystalline Compound 1 (Pattern 1) and amorphous Compound 2 were used in the following experiments (in up to 14 solvents):
Maturation cycles from RT to 50° C.
Cooling of concentrated solutions from RT to 4° C. then to −20° C.
Solvent evaporation from concentrated solution at RT.
Compound 1
The following experimental procedure was used throughout. 25-30 mg of Compound 1 (Pattern 1) was weighted into 2 cm$^3$ vials and the appropriate volume of solvent was added [DCM (5 volumes), Chlorobenzene (20 volumes), Toluene (20 volumes), Anisole (20 volumes), Heptane (20 volumes), tert-Butylmethyl ether (20 volumes), Ethyl acetate (10 volumes), Acetone (5 volumes), Ethanol (5 volumes), Methanol (5 volumes), Acetonitrile (10 volumes), Tetrahydrofuran (5 volumes), Water (20 volumes), Nitromethane (20 volumes)]. On shaking at ambient, suspensions were obtained except in samples containing DCM, acetone, ethanol, methanol and tetrahydrofuran. The suspensions were then subjected to a series of heat/cool cycles from RT to 50° C. (8 hour cycles) for 8 days with an intermediate XRPD analysis of the filtered solid after 5 days. All clear solutions obtained at ambient were cooled to 4° C. prior to being evaporated if no precipitate was obtained.

XRPD Pattern 1 was also obtained from solids recovered after solvent evaporation in ethyl acetate, acetone, and nitromethane.

XRPD Pattern 2 was recorded after 5 days of maturation in chlorobenzene, toluene, tert-butylmethyl ether, and water.

XRPD Pattern 3 was obtained after 5 days of storage at 4° C. in ethanol and methanol.

XRPD Pattern 4 was recorded after maturation and cooling at 4° C. in: chlorobenzene after 8 days of maturation or DCM after 5 days of storage at 4° C.

Compound 2
Another series of experiments was performed with amorphous material of Compound 2 in the same range of class 2 and 3 solvents using the following procedure. 25-30 mg of amorphous Compound 2 was weighted into 2 cm$^3$ vials and the appropriate solvent was added: DCM (5 volumes), Chlorobenzene (5 volumes), Toluene (5 volumes), Anisole (5 volumes), Heptane (20 volumes), tert-Butylmethyl ether (5 volumes), Ethyl acetate (5 volumes), Acetone (5 volumes), Ethanol (5 volumes), Methanol (5 volumes), Acetonitrile (5 volumes), Tetrahydrofuran (5 volumes), Water (5 volumes), Nitromethane (5 volumes).

On shaking at ambient, homogeneous solutions were obtained except in the sample containing heptane (no dissolution of Compound 2): this sample was then subjected to a series of heat/cool cycles from RT to 50° C. (8 hour cycles) over a 5 days period. All the clear solutions were cooled to 4° C. If no precipitate was obtained the samples were cooled further to −20° C. prior to being slowly evaporated at ambient.

Compound 2 was completely dissolved in 5 vol at ambient for almost all the commonest class 2 and 3 solvents, the exception being heptane. In this solvent Compound 2 was not dissolved in 20 vol at 50° C. and remained in suspension as an amorphous material after 5 days of maturation cycles. Mixtures of an amorphous gum and crystalline material were obtained after evaporation of samples containing acetone and methanol. These samples showed birefringence under polarised light and a slight crystallinity was detected on the X-Ray diffractogram recorded on the solid obtained after evaporation of acetone: Pattern 1 of the sodium salt. After evaporation, these 2 samples were subjected to maturation under stirring at RT with the addition of 0.5 mL of heptane (as anti-solvent) in order to crystallise the amorphous portions of these samples. After 12 hours, the solids were filtered under vacuum and XRPD analyses showed the same crystalline profile (Pattern 1 of the sodium salt) with a significant increase in crystallinity.

Pattern 1 of Compound 2 is also obtained from amorpohous Compound 2 by one of the following methods:
after maturation (RT-50° C./8 hour cycles) in chlorobenzene & EtOAc/heptane mixtures;
GVS @ 25° C.;
storage @ 40° C./75% R.H;
after slow evaporation @ RT in acetone and methanol and then 12 hours of maturation with heptane.

Example 3: X-Ray Powder Diffraction (XRPD)

X-Ray powder diffraction patterns were collected on a Bruker AXS/Siemens D5000 or Bruker AXS C2 GADDS or Bruker AXS D8 Advance diffractometer.

Bruker AXS/Siemens D5000
X-Ray Powder Diffraction patterns were collected on a Siemens D5000 diffractometer using Cu Ka radiation (40 kV, 40 mA), 0-0 goniometer, divergence of V20 and receiving slits, a graphite secondary monochromator and a scintillation counter. The instrument is performance checked using a certified Corundum standard (NIST 1976). The software used for data collection was Diffrac Plus XRD Commander v2.3.1 and the data were analyzed and presented using Diffrac Plus EVA v 11,0.0.2 or v 13.0.0.2.
Ambient Conditions
Samples run under ambient conditions were prepared as flat plate specimens using powder. Approximately 10 mg of the sample was gently packed into a cavity cut into polished, zero-background (510) silicon wafer. The sample was rotated in its own plane during analysis.
The details of the data collection are:
Angular range: 2 to 42° 2θ
Step size: 0.05° 2θ
Collection time: 4 s·step$^{-1}$
Bruker AXS C2 GADDS
X-Ray Powder Diffraction patterns were collected on a Bruker AXS C2 GADDS diffractometer using Cu Ka radiation (40 kV, 40 mA), automated XYZ stage, laser video microscope for auto-sample positioning and a HiStar 2-dimensional area detector. X-ray optics consists of a single Gobel multilayer mirror coupled with a pinhole collimator of 0.3 mm. The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Bruker AXS D8 Advance

X-Ray Powder Diffraction patterns were collected on a Bruker D8 diffractometer using Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v 11,0.0.2 or v 13.0.0.2. Samples were run under ambient conditions as flat plate specimens using powder. Approximately 10 mg of the sample was gently packed into a cavity cut into polished, zerobackground (510) silicon wafer. The sample was rotated in its own plane during analysis. The details of the data collection are:

Angular range: 2 to 42° 2θ
Step size: 0.05° 2θ
Collection time: 0.5 s·step$^{-1}$ XRPD on Amorphous Compound 2

FIG. 1 illustrates the XRPD of amorphous Compound 2.

XRPD on Pattern 1 of Crystalline Compound 2 (Post GVS at 25° C.)

The X-Ray powder diffraction pattern for Pattern 1 is displayed in FIG. 2 and characteristic peaks were tabulated in Table 1.

TABLE 1

XRPD pattern peak data for Pattern 1 of Crystalline Compound 2

| Angle 2-Theta ° | Intensity % |
|---|---|
| 3.75 | 91.5 |
| 6.80 | 39.7 |
| 8.72 | 37.9 |
| 11.11 | 32.2 |
| 13.59 | 100.0 |
| 15.78 | 36.3 |
| 17.13 | 87.6 |
| 17.54 | 46.4 |
| 17.94 | 47.3 |
| 18.81 | 50.7 |

XRPD on Pattern 1 Free Acid

The X-Ray powder diffraction pattern for Pattern 1 of Compound 1 is displayed in FIG. 4 and characteristic peaks were tabulated in Table 2.

TABLE 2

XRPD pattern peak data for Pattern 1 of Crystalline Compound 1

| Angle 2-Theta ° | Intensity % |
|---|---|
| 11.43 | 53.5 |
| 16.93 | 71.5 |
| 17.93 | 100.0 |
| 18.95 | 66.9 |

XRPD on Pattern 2 Free Acid (from Water)

The X-Ray powder diffraction pattern for Pattern 2 of Compound 1 is displayed in FIG. 5 and characteristic peaks were tabulated in Table 3.

TABLE 3

XRPD pattern peak data for Pattern 2 of Crystalline Compound 1

| Angle 2-Theta ° | Intensity % |
|---|---|
| 11.23 | 32.9 |
| 11.50 | 91.6 |
| 12.34 | 41.3 |
| 13.67 | 50.5 |
| 16.51 | 57.9 |
| 16.99 | 53.7 |
| 17.99 | 100.0 |
| 19.07 | 73.3 |
| 20.62 | 63.8 |
| 22.50 | 51.3 |
| 22.77 | 45.5 |
| 23.04 | 56.2 |

XRPD on Pattern 3 Free Acid (from Methanol)

The X-Ray powder diffraction pattern for Pattern 3 of Compound 1 is displayed in FIG. 6 and characteristic peaks were tabulated in Table 4.

TABLE 4

XRPD pattern peak data for Pattern 3 of Crystalline Compound 1

| Angle 2-Theta ° | Intensity % |
|---|---|
| 6.30 | 24.6 |
| 8.10 | 100.0 |
| 10.15 | 12.9 |
| 11.95 | 54.8 |
| 13.56 | 27.5 |
| 14.91 | 14.1 |
| 16.04 | 19.4 |
| 16.36 | 46.0 |
| 16.50 | 47.1 |
| 17.63 | 25.9 |
| 18.29 | 61.3 |
| 18.75 | 39.7 |
| 18.91 | 55.8 |
| 19.59 | 31.1 |
| 19.80 | 27.5 |
| 21.54 | 33.3 |
| 23.42 | 40.9 |
| 25.47 | 32.3 |

XRPD on Pattern 4 Free Acid (from Chlorobenzene)

The X-Ray powder diffraction pattern for Pattern 4 of Compound 1 is displayed in FIG. 7 and characteristic peaks were tabulated in Table 5.

TABLE 5

XRPD pattern peak data for Pattern 4 of Crystalline Compound 1

| Angle 2-Theta ° | Intensity % |
|---|---|
| 4.11 | 41.2 |
| 8.26 | 21.7 |
| 11.46 | 15.7 |
| 12.38 | 100.0 |
| 16.52 | 60.9 |
| 18.57 | 30.7 |
| 20.65 | 60.1 |
| 22.00 | 86.1 |
| 24.87 | 34.3 |

Example 4: Differential Scanning Calorimetry (DSC) and Thermogravimetric Analysis (TGA)

DSC data were collected on a Mettler DSC 823e equipped with a 50 position autosampler. The instrument was calibrated for energy and temperature using certified indium. Typically 0.5-1.5 mg of each sample, in a pin-holed aluminium pan, was heated at 10° C.·min$^{-1}$ from 25° C. to 300° C. A nitrogen purge at 50 ml·min-1 was maintained over the sample. The instrument control and data analysis software was STARe v9.10.

TGA data were collected on a Mettler TGA/SDTA 851e equipped with a 34 position autosampler. The instrument was temperature calibrated using certified indium. Typically 3-10 mg of each sample was loaded onto a pre-weighed aluminium crucible and was heated at 10° C.·min$^{-1}$ from ambient temperature to 350° C. A nitrogen purge at 50 ml·min-1 was maintained over the sample. The instrument control and data analysis software was STARe v9.10.

Amorphous Compound 2

One mass loss was recorded at 4.45% w/w associated with the presence of residual solvent. A possible glass transition was noted at 109° C. (midpoint).

Pattern 1 of Crystalline Compound 2 (Post GVS at 25° C.)

In the DSC endothermic peaks were observed at about 70.45° C., 122.26° C., and 138.06° C.

TGA-DSC performed on the sample of amorphous Compound 2 after 1 week of storage at 40° C./75% R.H. showed a mass loss at 5.57% w/w associated with a desolvation peak in DSC at 31.8° C. The melt was recorded at 130.1° C. and the degradation occurred from ~260° C.

Pattern 1 Free Acid 2 mass losses were observed in TGA at 1.51 and 6.91% w/w associated with 2 endothermic events in DSC recorded at 32.7 and 77.8° C. (onset) which could correspond to desolvation phenomena. A third endotherm was recorded at 136.4° C. (onset) corresponding to the melt of the product. The degradation occurred from ~260° C.

Pattern 2 Free Acid

A mass loss of 2.61% w/w was recorded from a sample obtained from toluene associated with a broad desolvation peak in DSC at 138.7° C. (onset)

A mass loss of 2.56% w/w was recorded from a sample obtained from water associated with a desolvation peak measured in DSC at 52.1° C. (onset). A second endotherm associated to the melt was recorded at 139.2° C. (onset). The degradation occurred from ~260° C.

Pattern 3 Free Acid (from Methanol)

A mass loss of 1.95% w/w was recorded from a sample obtained from methanol associated with an endothermic peak in DSC at 38.9° C. (onset). A second endotherm associated to the melt was recorded at 147.3° C. The degradation occurred from ~260° C.

The sample obtained from methanol was dried at 80° C. in a vacuum oven. After 2 hours, the sample was analyzed by TGA/DSC. A mass loss was recorded at 1.1% w/w in the TGA associated with a weak endothermic event in the DSC. A second endotherm associated to the melt was recorded at 148.5° C. (onset). The degradation occurred from ~260° C.

Example 5: Gravimetric Vapour Sorption (GVS)

Sorption isotherms were obtained using a SMS DVS Intrinsic moisture sorption analyzer, controlled by SMS Analysis Suite software. The sample temperature was maintained at 25° C. by the instrument controls. The humidity was controlled by mixing streams of dry and wet nitrogen, with a total flow rate of 200 ml·min-1. The relative humidity was measured by a calibrated Rotronic probe (dynamic range of 1.0-100% RH), located near the sample. The weight change, (mass relaxation) of the sample as a function of % RH was constantly monitored by the microbalance (accuracy ±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0.5-90% RH range

TABLE 6

Method Parameters for SMS DVS Intrinsic Experiments

| Parameters | Values |
|---|---|
| Adsorption - Scan 1 | 40-90 |
| Desorption/Adsorption - Scan 2 | 85-Dry, Dry-40 |
| Intervals (% RH) | 10 |
| Number of Scans | 2 |
| Flow rate (ml · min−1) | 200 |
| Temperature (° C.) | 25 |
| Stability (° C. · min−1) | 0.2 |
| Sorption Time (hours) | 6 hour time out |

Pattern 1 of Compound 1

The mass change was more than 12% w/w between 0-90% R.H. (it is not known how much of this uptake is associated with the crystalline part of the material). The material is hygroscopic. No significant changes were observed in the XRPD after GVS analysis.

Amorphous Compound 2

Sample deliquesced (mass change >30% w/w at 80% R.H.). The intersection between the 1st sorption/desorption curves was due to a crystallization phenomenon. A crystalline solid was observed by XRPD post GVS (Pattern 1 of the sodium salt).

Example 6: Thermodynamic Aqueous Solubility

Aqueous solubility was determined by suspending sufficient compound in water to give a maximum final concentration of ≥20 mg·ml-1 of the parent free-form of the compound. The suspension was equilibrated at 25° C. for 24 hours then the pH was measured. The suspension was then filtered through a glass fibre C filter into a 96 well plate unless stated otherwise. The filtrate was then diluted by a factor of 101. Quantitation was by HPLC with reference to a standard solution of approximately 0.25 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

TABLE 7

HPLC Method Parameters for Solubility Measurements

| | |
|---|---|
| Type of method: | Reverse phase with gradient elution |
| Column: | Phenomenex Luna, C18 (2) 5 µm 50 × 4.6 mm |
| Column Temperature (° C.): | 25 |
| Standard Injections (µl): | 1, 2, 3, 5, 7, 10 |
| Test Injections (µl): | 1, 2, 3, 10, 20, 50 |

TABLE 7-continued

HPLC Method Parameters for Solubility Measurements

| | |
|---|---|
| Detection: Wavelength, Bandwidth (nm): | 260, 80 |
| Flow Rate (ml · min$^{-1}$): | 2 |
| Phase A: | 0.1% TFA in water |
| Phase B: | 0.085% TFA in acetonitrile |

| Timetable: | Time (min) | % Phase A | % Phase B |
|---|---|---|---|
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.02.01-SR1.

TABLE 8

Solubility results

| Sample | Test Solvent | pH of Unfiltered Saturated solution | Solubility mg/ml Free Base equivalent | Appearance |
|---|---|---|---|---|
| Compound 1 Pattern 1 | pH 1.5 | 2.04 | 0.013 | Residual Solid |
| Compound 1 Pattern 1 | pH 4.0 | 4.23 | 0.0059 | Residual Solid |
| Compound 1 Pattern 1 | pH 5.0 | 5.23 | 0.027 | Residual Solid |
| Compound 1 Pattern 1 | pH 6.5 | 6.72 | 0.39 | Suspension |
| Compound 1 Pattern 1 | pH 7.4 | 7.63 | 7.6 | Suspension |
| Compound 2 Pattern 1 | pH 1.5 | 2.73 | 0.0058 | Residual Solid |
| Compound 2 Pattern 1 | pH 4.0 | 4.67 | 0.0023 | Residual Solid |
| Compound 2 Pattern 1 | pH 5.0 | 5.88 | 0.04 | Suspension |
| Compound 2 Pattern 1 | pH 6.5 | 7.06 | 4.1 | Suspension/ Residual Solid |
| Compound 2 Pattern 1 | pH 7.4 | 7.97 | 18.0 | Suspension |

It was noted that for both the free base and the sodium salt the solubility was higher in the pH 1.5 buffer than in the pH 4 which would be unusual for a compound with just a carboxylic group. However, there is an amide group which has a predicted basic pKa of 0.7 (which is below our measurable range), this could explain the higher solubility seen.

For the solubility of the sodium salt in pH 7.4 buffer, the saturated solution had to be centrifuged as the solution would not go through our standard filter plate.

Pattern 1 of Compound 1: Thermodynamic solubility in water 6.2 mg/mL (pH of unfiltered solution: 7.92).

Amorphous Compound 2: Thermodynamic solubility in water >20 mg/mL (pH of unfiltered solution: 8.18).

Example 7: Chemical Purity Determination

Purity analysis was performed by HPLC on an Agilent HP1100 series system equipped with a diode array detector and using ChemStation software vB.02.01-SR1.

TABLE 9

HPLC Method Parameters for Chemical Purity Determinations

| | |
|---|---|
| Sample Preparation: | 0.4-1.4 mg/ml in acetonitrile: water 1:1 v/v |
| Column: | Phenomenex Luna C18 (2), 150 × 4.6 mm, 5 µm |
| Column Temperature (° C.): | 25 |
| Injection (µl): | 5 |
| Detection: Wavelength, Bandwidth( nm): | 255, 90 |
| Flow Rate (ml · min−1): | 1 |
| Phase A: | 0.1%TFA in water |
| Phase B: | 0.085% TFA in acetonitrile |

| Timetable: | Time (min) | % Phase A | % Phase B |
|---|---|---|---|
| | 0 | 95 | 5 |
| | 25 | 5 | 95 |
| | 25.2 | 95 | 5 |
| | 30 | 95 | 5 |

Samples of Compound 1 and Compound 2 were found to be greater than 90% pure. In some embodiments, samples of Compound 1 were found to be greater than 95% pure, greater than 96% pure, greater than 97% pure, greater than 98% pure, greater than 99% pure. In some embodiments, samples of Compound 2 were found to be greater than 94% pure, greater than 95% pure, greater than 96% pure, greater than 97% pure, greater than 98% pure, greater than 99% pure.

In some embodiments, samples of Compound 2 include a detectable amount of at least one of the following compounds:

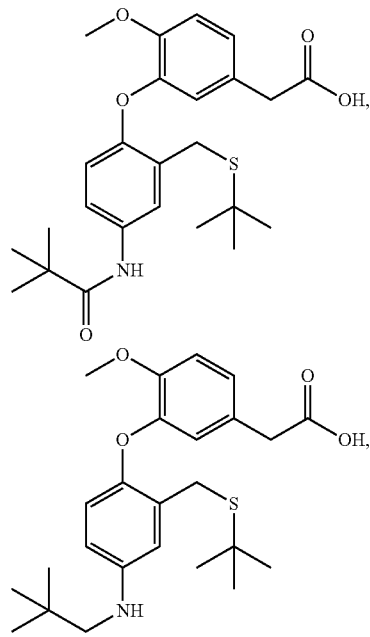

69
-continued

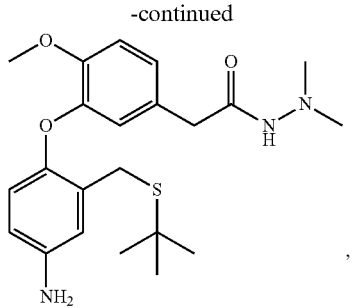

,

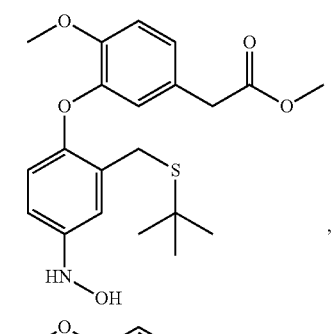

,

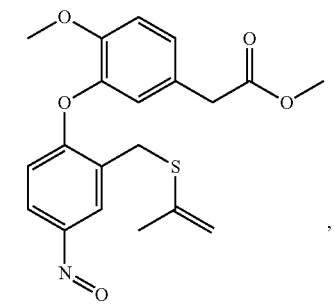

,

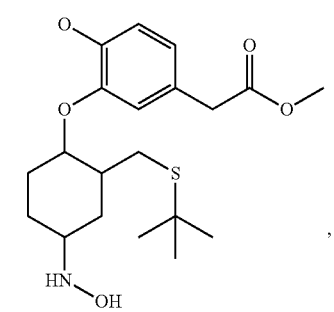

,

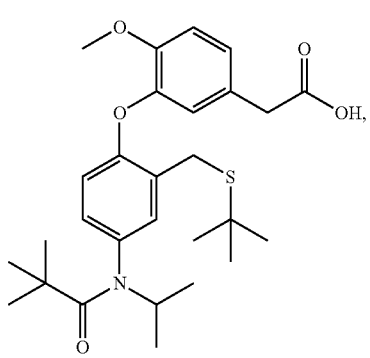

70
-continued

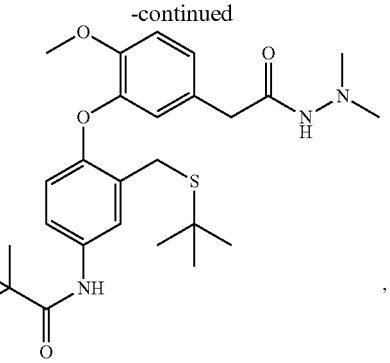

,

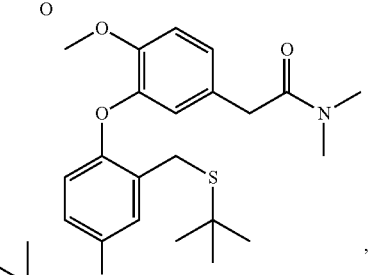

,

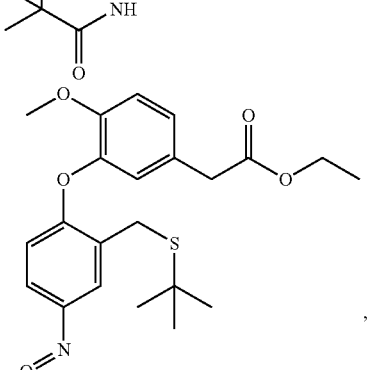

,

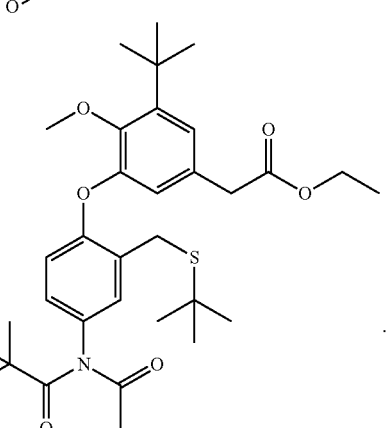

.

Residual Solvents

The test for Residual Solvents is performed to detect trace amounts of solvents used in the synthesis that may be present in the API. The analysis is performed via headspace or direct injection analysis using a gas chromatograph equipped with a flame ionization detector (FID). All residual solvents used in the synthesis are capable of being detected by this method.

Potential residual solvents include acetone, ethanol, methanol, dichloromethane, methyl-tert-butyl-ether (MTBE), ethyl acetate, tetrahydrofuran, heptane, dimethoxyethane (DME).

TABLE 10

| Residual Solvents by GC Headspace | |
|---|---|
| Residual Solvent | Amount (ppm) |
| Acetone | 8412 ppm |
| ethanol | <145 ppm |
| methanol | <130 ppm |
| MTBE | <114 ppm |
| THF | <137 ppm |
| heptane | 1405 ppm |
| Ethyl acetate | 413 ppm |
| dichloromethane | <215 |
| 1,4-dioxane | <198 ppm |
| DME | <148 ppm |

Example 8: Heavy Metals (as Lead)

This test is performed according to USP<231> Method II.

Pharmaceutical Compositions

Pharmaceutical compositions that include Compound 1, including pharmaceutically acceptable salts (e.g. Compound 2) and/or pharmaceutically acceptable solvates thereof include a variety of forms. In one aspect, pharmaceutical compositions are in the form of oral dosage forms. In some embodiments, the oral dosage forms are formulated as: oral solutions, oral suspensions, tablets, pills, or capsules.

Example 9: Oral Solutions

In one aspect, an oral pharmaceutical composition in the form of an oral solution is prepared as outlined below.

Oral solutions were prepared at 20 mg/mL of Compound 2.

Oral Solution A:

In one embodiment, an oral pharmaceutical composition is prepared with the following ingredients:

20 mg/mL of Compound 2 aqueous 10 mM $Na_2CO_3$

20% propylene glycol

Oral Solution B:

In one embodiment, an oral pharmaceutical composition is prepared with the following ingredients:

20 mg/mL of Compound 2 aqueous 10 mM $Na_2CO_3$

20% propylene glycol

2% Tween 80

Oral Solution C:

In one embodiment, an oral pharmaceutical composition is prepared with the following ingredients:

20 mg/mL of Compound 2

0.5% methocel aqueous solution

The manufacturing process for the oral solutions of Compound 2 described above is as follows: Weigh the required amount of sodium carbonate (if present) and transfer to the container. Add the required amount of water to make a 10 mM solution and mix until dissolved. Weigh the required amount of propylene glycol and Tween 80 (if present) and add this to the solution and mix until homogenous. Weigh the required amount of Compound 2 and slowly add to the solution. Mix until all Compound 2 is dissolved (sonicate, warm, or stir if necessary).

Example 10: Capsule Formulations

Immediate Release Capsules

In one embodiment, capsule formulations of Compound 2 for administration to humans are prepared with the following ingredients:

| Component | Function | Quantity per Size 4 Capsule mg | Quantity per Size 1 Capsule mg |
|---|---|---|---|
| Compound 2 (Pattern 1) | Active | 5 to 50 mg | 50 to 200 mg |
| Hypromellose, USP | Capsule Shell | 1 capsule | 1 capsule |

Matching Placebo Capsules (for clinical study purposes) are prepared with the following ingredients:

| Component | Function | Quantity per Size 4 Capsule mg | Quantity per Size 1 Capsule mg |
|---|---|---|---|
| Mannitol | Bulking Agent | 5 to 50 mg | 50 to 200 mg |
| Hypromellose, USP | Capsule Shell | 1 capsule | 1 capsule |

The process to prepare Compound 2 in a capsule (which is the same for the preparation of the placebo capsules) is as follows: Weigh the required amount of Compound 2, add into the appropriate size capsule, and close capsule. For example, in one embodiment, 5 mg of Compound 2 is placed into a Size 4 Capsule. In one embodiment, 50 mg of Compound 2 is placed into a Size 4 Capsule. In one embodiment, 50 mg of Compound 2 is placed into a Size 1 Capsule. In one embodiment, 200 mg of Compound 2 is placed into a Size 1 Capsule.

In some embodiments, the capsules are stored at 25° C. for up to 48 hours.

In rats and dogs dosed with the capsule formulations described above and the oral solutions described above, there was no significant difference in bioavailability observed between the different oral formulations.

Enteric Coated Capsules

Capsule Preparation

Capsules (Size 1, white opaque V-caps (HPMC), manufactured by Capsugel, Lot 90083361) were used and Compound 2 (Pattern 1) was placed into each capsule (between about 58.5 mg and about 64.5 mg of Compound 2). The junction between the body and cap for each capsule was manually banded with gelatin.

Three enteric coated capsules were prepared using Eudragit L100-55 (pH 5.5), Eudragit L100 (pH 6.0), and Eudragit 5100 (pH 7.0).

Polymer Preparations

The stepwise procedure for each of the three enteric coating polymers is listed below.

Eudragit L100-55 (pH 5.5)

| Ingredient | Weight % |
|---|---|
| Eudragit L100-55 | 29.6 |
| 1N NaOH | 10.0 |
| Water | 60.4 |

To prepare the dispersion, Eudragit L100-55 was added slowly into the water and stirred for a bout 5 minutes. Ensured the powder was thoroughly wetted and avoided lumping and foam formation.

Added 1 N NaOH into the suspension and stirred for about 30 minutes to make the dispersion.

| Ingredient | Weight % |
|---|---|
| Eudragit L100-55 Dispersion | 41.67% |
| Triethyl citrate | 1.25% |
| Talc | 6.25% |
| Water | 50.83% |
| Simethicone | NA |

Homogenized talc and triethyl citrate in water using a high shear mixer for 10 minutes to make the excipients suspension. Added 7 drops of simethicone.

Poured excipients suspension slowly into the Eudragit dispersion.

Eudragit L100 (pH 6.0)

| Ingredient | Weight % |
|---|---|
| Eudragit L100 | 9.9 |
| Triethyl citrate | 4.98 |
| 1N NH4OH | 5.60 |
| Talc | 4.96 |
| Water | 74.49 |
| Simethicone | NA |

Added Eudragit L100 slowly into ⅔ the water and stirred for about 5 minutes. Ensured the powder was thoroughly wetted and avoided lumping and foam formation. Added 1N NH4OH slowly into suspension with stirring and stirred for about 60 minutes. Added triethyl citrate into suspension with stirring and stirred for about 60 minutes. Homogenized the talc with the remaining ⅓ of water for about 10 minutes with the high shear mixer. Added 11 drops of simethicone. Poured the talc suspension into dispersion then stirred overnight.

Eudragit S100 (pH 7.0)

| Ingredient | Weight % |
|---|---|
| Eudragit S100 | 9.94 |
| Triethyl citrate | 4.97 |
| 1N NH$_4$OH | 6.75 |
| Talc | 4.97 |
| Water | 73.37 |
| Simethicone | NA |

Added Eudragit S100 slowly into ⅔ the water and stirred for about 5 minutes. Ensured the powder was thoroughly wetted and avoided lumping and foam formation. Added 1N NH4OH slowly into suspension with stirring and stirred for about 60 minutes. Added triethyl citrate into suspension with stirring and stirred for about 60 minutes. Homogenized the talc with the remaining ⅓ of water for about 10 minutes with the high shear mixer. Added 11 drops of simethicone. Poured the talc suspension into dispersion while stirring.

Enteric Coating Process

The enteric coating process was conducted in a Fluid Air Fluid Bed granulator. The Wurster (bottom spray) setup was utilized. The polymers were infused into the granulator to apply a coating. The final coating percentage was approximately 10% by weight for each polymer. Adjustments to the Spray Air were made from observation of the bed volume during the process. To maintain a minimum bed volume, placebo capsules were made in addition to active capsules.

| Parameters | L100-55 | L100 | S100 |
|---|---|---|---|
| Pump Rate (mL/min) | 1.7 | 1.6 | 1.6 |
| Inlet Flow (cfm) | 60 | 60 | 60 |
| Coating Time (min) | 38 | 40 | 19 |
| Spray Air (psi) | 10 | 10 | 13 |
| Filter Cleaning (psi) | 30 | 30 | 30 |
| Inlet Temp (° C.) | 45.2 | 45.0 | 45.0 |
| Product Temp (° C.) | 43.2 | 43.2 | 43.2 |

Analytical Check

A representative sample from each of the three enteric coatings was subjected to 2 hours in SGF (minus enzyme). The capsule was then removed and placed in high pH buffer to record the disintegration times.

| Coating | Release Buffer pH | Total Time (min) |
|---|---|---|
| L100-55 | 5.5 | 12 |
| L100 | 6.0 | 20 |
| S100 | 7.0 | 44 |
| S100 | 7.4 | 12 |

Example 11: Regional Dosing Study

Male Sprague-Dawley rats (weighing from about 200 to about 300 grams) in the fasted state received a single injection of a solution of Compound 2 (5% methocel) in the duodenum, jejunum or ileum. This was compared with PO administration of the same formulation of Compound 2. All rats were dosed at 10 mg/kg.

The results of the regional dosing study are displayed in Table 11.

TABLE 11

Regional Dosing Studies in Rat

| Parameter | IV | Duo | Jej | Ile | PO |
|---|---|---|---|---|---|
| Dose (mg/kg) | 2 | 10 | 10 | 10 | 10 |
| AUC (hr*ug/mL) | 3.67 | 5.01 | 8.11 | 1.98 | 4.37 |
| t1/2 (hr) | 2.0* | 4.12 | 5.29 | 5.06 | 1.50 |
| % F | | 27.3% | 44.2% | 10.8% | 23.8 |
| Cmax (µg/mL) | | 4.31 | 12.73 | 0.61 | 3.06 |
| Tmax (hr) | 0.08 | 0.25 | 0.25 | 0.63 | 0.75 |

The results shown in Table 11 demonstrate that Compound 2 is preferentially absorbed in the jejunum.

In a separate study, male Beagle dogs were dosed with the capsule formulations as described herein. The results are present below.

| Parameter | IV | EC-Capsule[1] | Capsule |
|---|---|---|---|
| Species | Dog/male | Dog/male | Dog/male |
| Fed/Fasted | Fasted | Fasted | Fasted |
| Vehicle | Saline | powder filled capsule | powder filled capsule |
| Dose (mg/kg) | 2 | 5 | 5.6 |
| AUC (hr*ug/mL) | 6.5 | 20.9 | 14.3 |
| Cl$_{Pl}$ (mL/min/kg) | 5.0 | | |
| VDss (L/kg) | 0.9 | | |

-continued

| Parameter | IV | EC-Capsule[1] | Capsule |
|---|---|---|---|
| $t_{1/2\ 24}$ hr (hr) | 5.1 | 2.4 | 2.8 |
| % F | | 128.5 | 78.6 |
| CO (ug/mL) | 10.3 | | |
| Cmax (µg/mL) | | 14.4 | 4.8 |
| Tmax (hr) | 0.1 | 1.0 | 2.1 |

[1]Enteric coating was L100-55

Although the results are presented for the capsules coated with L100-55, all three enteric coated capsules provided comparable results.

Example 12: Identification of Metabolic Pathways

The metabolic profile of Compound 1 was investigated using: (1) male Sprague-Dawley rat, male Beagle dog, and human liver microsomes; (2) rat and human hepatocytes; (3) bile collected from male Sprague-Dawley rats; and (4) rat and dog plasma after dosing.

Materials

Male Sprague-Dawley rat, male beagle dog, and mixed pool human liver microsomes were purchased from Xenotech (Kansas City, Mo.). Rat and human hepatocytes and InVitroGRO HI medium were purchased from In Vitro Technologies (Gaithersburg, Md.).

Microsomes

To determine the qualitative metabolic profile, 30 µM of Compound 1 was incubated aerobically with rat, dog, or human liver microsomes (1 mg/mL). The incubations were performed in phosphate buffer at pH7.4, 37° C., with the reaction initiated by the addition of β-NADPH and UDPGA (1 mM and 3 mM final concentration, respectively). The reaction was terminated by the addition of an equal volume of acetonitrile with 1.5% acetic acid after 60 min. The sample was centrifuged and the supernatant was transferred for LC/MS analysis.

Hepatocytes

Rat, dog or human hepatocytes were thawed according to the supplier's instructions. Cells were counted using the Trypan Blue method, and then diluted to $1 \times 10^6$ viable cells/ml with KB medium. Compound 1 was tested at 30 µM and incubated for up to 2 hours in rat hepatocytes and 4 hours in human hepatocytes at 37° C. Fresh human hepatocytes were from a single male donor lot Hu0778 (CellsDirect, Raleigh, N.C.). Reactions were terminated with addition of an equal volume of acetonitrile with 1.5% acetic acid, centrifuged, and supernatants were transferred for LC-MS/MS analysis.

Rat Bile Duct Cannulation

Rats with surgically placed bile duct and jugular vein cannula were purchased from Charles River Laboratories and allowed to acclimate for 2 days. Compound 1 was intravenously dosed (2 mg/kg) to three rats as a solution in 0.9% saline (2 mg/mL; 1 mL/kg). Bile was collected at time-points 0-2, 2-5, 5-8, and 8-24 hrs post-dose in 8 mL scintillation vials and stored at −40° C. until LC-MS/MS analysis. Urine was collected at time points 0-4, 4-8 and 8-24 hrs post-dose in 5 mL scintillation vials and stored at −40° C. until analysis by LC-MS/MS.

LC-MS Analysis

Analyses were performed using a Waters YMC ODS-AQ column (2.1×150 mm; 3 µm) linked to a Shimadzu LC-10AD VP with SCL-10A VP system controller. Tandem mass spectrometric (MS/MS) detection was carried out on a Sciex ABI3200 QTrap in the positive ion mode (ESI) by multiple reaction monitoring, precursor ion scan, and enhanced product ion scan. The mobile phases contained 10 mM ammonium acetate in water with 0.05% formic acid (solvent A) and 10 mM ammonium acetate in 50% acetonitrile/50% methanol with 0.05% formic acid (solvent B). The flow rate was maintained at 0.25 mL/min and the total run time was 65 min. Analytes were separated using a linear gradient as follows:

1. Mobile phase was held for 5 min at 5% B,
2. B was increased from 5% to 95% over then next 50 min,
3. B was held constant for 5 min at 95%, and
4. B was returned to the initial gradient conditions.

For metabolite quantification, the same analysis was performed as above, but the flow rate was maintained at 0.25 mL/min and the total run time was 18 min. Analytes were separated using a linear gradient as follows:

1. mobile phase was held for 3 min at 5% B,
2. B was increased from 5% to 95% over then next 2 min,
3. B was held constant for 9 min at 95%, and
4. B was returned to the initial gradient conditions.

Results

The following metabolites were observed both in vitro and in vivo:

TABLE 12

| | Metabolites of Compound 1 | |
|---|---|---|
| Metabolite | Structure | Metabolite Name |
| M1 | 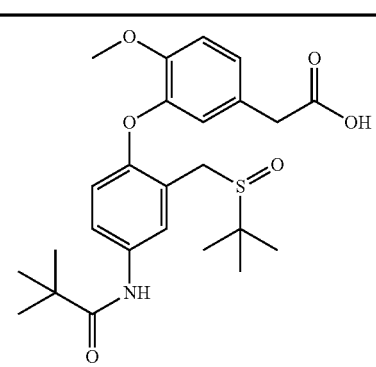 | 2-(3-(2-(tert-butylsulfinylmethyl)-4-pivalamidophenoxy)-4-methoxyphenyl)acetic acid |

TABLE 12-continued

Metabolites of Compound 1

| Metabolite | Structure | Metabolite Name |
|---|---|---|
| M2 | 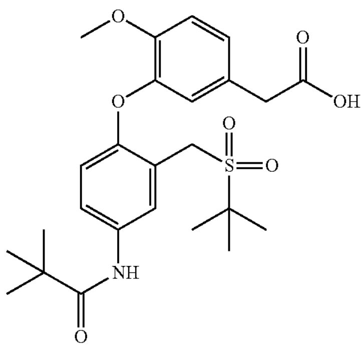 [SMILES: COc1ccc(CC(=O)O)cc1Oc1ccc(NC(=O)C(C)(C)C)cc1CS(=O)(=O)C(C)(C)C] | 2-(3-(2-(tert-butylsulfonylmethyl)-4-pivalamidophenoxy)-4-methoxyphenyl)acetic acid |
| M3 | 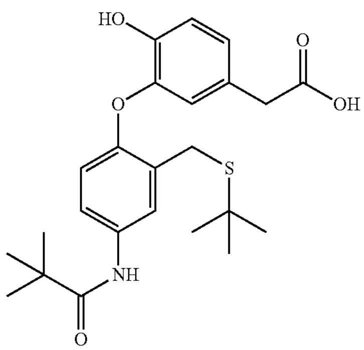 [SMILES: CC(C)(C)SCc1cc(NC(=O)C(C)(C)C)ccc1Oc1cc(CC(=O)O)ccc1O] | 2-(3-(2-(tert-butylthiomethyl)-4-pivalamidophenoxy)-4-hydroxyphenyl)acetic acid |
| M4 | Acyl-glucuronide of Compound 1 | Acyl-glucuronide of Compound 1 |
| M5 | 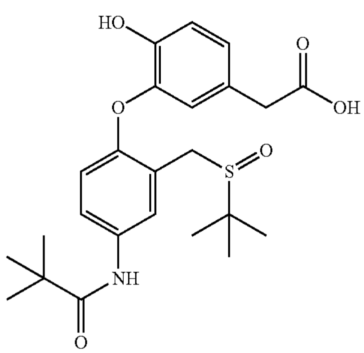 [SMILES: CC(C)(C)C(=O)Nc1ccc(Oc2cc(CC(=O)O)ccc2O)c(CS(=O)C(C)(C)C)c1] | 2-(3-(2-(tert-butylsulfinylmethyl)-4-pivalamidophenoxy)-4-hydroxyphenyl)acetic acid |
| M6 | Acyl-glucuronide of M3 | Acyl-glucuronide of M3 |
| M7 | Acyl-glucuronide of M1 | Acyl-glucuronide of M1 |
| M8 | Acyl-glucuronide of M2 | Acyl-glucuronide of M2 |

Metabolites M1, M2, M3, and M5 are active metabolites.

Example 13: Extracellular Cytochrome P450 Inhibition

To investigate whether Compound 2 would likely cause any drug-drug interactions, microsomes were incubated test substrates, which were known to be metabolized by CYP enzymes, with or without Compound 2.

Specific aspects of the incubation conditions for each assay (e.g., protein concentration, incubation time, etc.) are defined in Walsky & Obach, 2004 (Walsky, R. L., and Obach, R. S. Validated assays for human Cytochrome P450 activities. *Drug Met. Disp.* 32:647-660, 2004.). In general, microsomes at protein concentrations as defined in Table 12 were mixed with buffer (100 mM $KH_2PO_4$, pH 7.4), $MgCl_2$ (6 mM)) and substrate, and were kept on ice. Aliquots of this mixture (89 μL) were delivered to each well of a 96-well polypropylene plate which contained an aliquot of inhibitor (1 μL) in acetonitrile:water (1:1). Final solvent concentrations were less than 1% (v/v). Incubations were initiated with the addition of 10 μL β-NADPH (10 mM stock) to a final volume of 100 μL. Incubations were terminated by the addition of 1.5-2× volume of acetonitrile containing internal standard (buspirone). Samples were centrifuged at 4° C., and supernatant was transferred for LC-MS/MS analysis.

The results are presented in Table 13.

TABLE 13

Lack of Extracellular Cytochrome P450 Inhibition

| Cytochrome P450 Enzyme | CYP Reaction | Compound 2 IC$_{50}$ (μM) | Inhibitor Control (IC$_{50}$ (μM)) |
|---|---|---|---|
| 3A4 | testosterone 6β-hydroxylation | 26 | Ketoconazole (0.02) |
| 3A4 | midazolam 1-hydroxylation | >50 | Ketoconazole (0.02) |
| 2C9 | diclofenac 4'-hydroxylation | >50 | Sulfaphenazole (0.21) |
| 2C19 | mephenytoin 4'-hydroxylation | >50 | (-)-N-3-benzyl-phenobarbital (8.7) |
| 2D6 | dextromethorphan O-demethylation | >50 | Quinidine (0.04) |
| 1A2 | phenacetin O-deethylation | >50 | Furafylline (2.2) |

Compound 2 was not a potent inhibitor of CYP3A4, CYP2C9, CYP2C19, CYP2D6, or CYP1A2 (IC$_{50}$>25 μM).

Example 14: Lack of Cellular Cytochrome P450 Induction

Compound 1 was not an inducer of P450 CYP3A4 or CYP2C9 in cryopreserved human hepatocytes, according to conversion of substrates to known metabolites with and without Compound 1 in the incubation. Briefly, cryopreserved human hepatocytes thawed and plated according to the manufacturer's instructions (In Vitro Technologies, Gathersburg, Md.). The cells were warmed and then poured into pre-warmed InVitroGRO CP medium, gently resuspended, and then the cells were counted using Trypan Blue exclusion. Cells were then diluted to 0.7×10$^{-6}$ viable cells/ml with CP medium. Each well received 0.2 ml of the viable cell mixture. The plate was gently shaken to disperse the cells evenly in the well, and the plate was incubated at 37° C., 5% carbon dioxide. At 24 hrs, medium was replaced with fresh CP medium. After 48 hrs, CP medium is replaced with HI medium containing Compound 1 tested at 10 μM, and the positive control, rifampicin was tested at 10 μM. Medium was replaced with fresh medium plus test article 24 hrs later. At 48 hrs, midazolam (50 μM) and diclofenac (50 μM) were incubated in 0.15 mL of K-H buffer for 4 hrs. Reactions were terminated with addition of 0.15 mL of acetonitrile containing internal standard (buspirone), material centrifuged, and supernatants were transferred for LC-MS analysis.

Rifampicin produced an 23-fold increase in 1-hydroxymidazolam (CYP3A4) and 1.3-fold increase in 4-hydroxydiclofenac (CYP2C9) production in hepatocytes when compared to native cells, while Compound 1 produced a 1.6-fold increase in 1-hydroxymidazolam and 0.5-fold increase in 4-hydroxydiclofenac. These data indicate that Compound 1 is not a strong inducer of CYP3A4 or CYP2C9 in human hepatocytes when tested at a concentration of 10 μM. (U.S. FDA Guidance for Industry, "Drug Interaction Studies—Study Design, Data Analysis, and Implications for Dosing and Labeling", September 2006).

Example 15: In Vitro DP$_2$/CRTH2 Binding Assay

The ability of Compound 1 to bind to the human DP$_2$ receptor was assessed via a radioligand binding assay using [$^3$H]PGD$_2$. HEK293 cells stably expressing recombinant human DP$_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM [$^3$H] PGD$_2$ and Compound 1 in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polythylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM PGD$_2$. IC$_{50}$s were determined using GraphPad prism analysis of drug titration curves. Mouse, rat and guinea pig DP2 receptors were also investigated.

Using radioligand membrane binding experiments, Compound 1 was shown to bind with high affinity to DP$_2$. Compound 1 showed potent inhibition of radiolabeled PGD$_2$, binding to mouse, rat, guinea pig and human DP$_2$ with average IC$_{50}$ values of 9.7 nM, 7.0 nM, 10.6 nM and 5.2 nM. The binding potency of Compound 1 is only slightly shifted in the presence of species-specific serum albumin. The average IC$_{50}$ values for Compound 1 inhibition of radioligand membrane binding on mouse, rat, guinea pig and human DP$_2$ in the presence of 0.2% species-specific albumin are 11.4 nM, 10.4 nM, 20.3 nM, and 19.7 nM. Compound 1 also displayed potent antagonism of PGD$_2$-stimulated DP$_2$ receptor activation.

Example 16: In Vitro GTPγS Binding Assay

The ability of Compound 1 to inhibit binding of GTP to DP$_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 μg per well) are incubated in 96-well plates with 0.05 nM [$^{35}$S]-GTPγS, 80 nM PGD$_2$, 5 μM GDP, and Compound 1 in Assay Buffer (50 mM Hepes, pH 7.4, 100 mM NaCl, 5 mM MgCl$_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD$_2$). IC$_{50}$s were determined using Graphpad prism analysis of drug titration curves. Compound 1 had an average IC$_{50}$ value of 2.8 nM in this assay. Compound 1 on its own showed no agonist activity at the DP2 receptor in the GTP binding assay at concentrations up to 100 μM.

Example 17: In Vitro Whole Blood Esoinophil Shape Change Assay

Compound 1 was evaluated in a whole blood assay of eosinophil shape change (ESC) to determine the ability of Compound 1 to antagonize a $PGD_2$-stimulated functional response in the context of whole blood.

Blood is drawn from consenting human volunteers in EDTA vacutainer tubes and used within 1 hr of draw. A 98 µl aliquot of blood is mixed with 2 µl of Compound 1 (in 50% DMSO) in 1.2 ml polypropylene tubes. The blood is vortexed and incubated at 37° C. for 5 minutes. 5 µl of 1 µM $PGD_2$ in PBS is added for a final concentration of 50 nM and the tubes briefly vortexed. The reactions are incubated for exactly 5 minutes at 37° C. and then terminated by placing the tubes on ice and immediately adding 250 µl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM $NH_4Cl$, 10 mM $KHCO_3$, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by $PGD_2$ was calculated as the difference between the percentage of high forward scatter eosinophils in the presence and absence of $PGD_2$. $IC_{50}$s were determined using Graphpad Prism® analysis of drug titration curves.

Compound 1 showed potent antagonism of DP2 receptor activation in whole blood and inhibited $PGD_2$-induced eosinophil shape change in human and guinea pig whole blood with average $IC_{50}$ values of 1.5 nM and 97.4 nM, respectively.

The potency of Compound 1 in the human ESC assay is relevant to clinical efficacy in asthmatics since eosinophil activation requires initial shape change and because eosinophil mediated damage has been correlated with severe exacerbations of asthma (Wardlaw, A. J., et al., 2002, *Clin. Sci.* 103:201-211).

The in vitro human ESC assay provides the most relevant indicator of human PD response, since this reflects the effect of Compound 1 on the eosinophils in circulating blood. Therefore, steady state trough plasma concentrations within the range of the human ESC $IC_{50}$ (1.5 nM or 0.7 ng/mL) to $IC_{90}$ (5.5 nM or 2.6 ng/mL) are expected to achieve a 50-90% pharmacodynamic response.

Example 18: Mouse Allergic Rhinitis Model

Compound 2 was evaluated in a mouse model of ovalbumin (OVA)-induced allergic rhinitis in which nasal ovalbumin challenges to OVA-primed mice elicits an increase in sneezing and nasal rubs (Methods were adapted from those detailed in Nakaya, M., et al. 2006, *Laboratory Investigation*, 86:917-926). OVA-primed mice received an intranasal challenge of OVA daily for 5 consecutive days. The number of sneezes and nasal rubs were counted over an 8 minute recording session on days 1, 3 and 5 immediately following OVA challenge. OVA caused a significant increase in both sneezing behavior and nasal rubs when compared to intranasal phosphate buffered saline (PBS) challenge. Daily administration of Compound 2 at a dose of 10 mg/kg, PO significantly reduced these nasal responses. The plasma exposure for Compound 1 measured in a satellite group was 1360 nM, 460 nM, 210 nM and 90 nM for time points 1, 2, 4, and 6 hr post-dose, respectively. These results indicate that in the setting of mouse allergic rhinitis, Compound 1 or a pharmaceutically acceptable salt thereof (e.g. Compound 2) improves nasal symptoms.

Example 19: Guinea Pig IV-DKPGD$_2$-Induced Peripheral Blood Leukocyte to Influx The ability of Compound 2 to inhibit leukocyte migration in vivo was assessed using intravenous injection of 13,14-dihydro-15-keto-prostaglandin D2 (DK-$PGD_2$). Methods were adapted from those detailed Shichijo et al., 2003, *Journal of Pharmacology and Experimental Therapeutics*, 307:518-525. Male Hartley guinea pigs were immunized with ovalbumin (OVA) on day 0 by intraperitoneal (IP) injection of 1 ml of a 100 µg/ml solution in Imject Alum. They were then used in the DK-$PGD_2$ procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-$PGD_2$ (1 mg/kg, IV). Thirty minutes after IV administration, blood was collected via the marginal ear vein into EDTA tubes for cell analysis. 10 µl blood was lysed in 190 µl water followed by a further 20-fold dilution in PBS. A 10 µl fraction was mixed with equal parts trypan blue and loaded on a hemocytometer. Cells were visualized at a magnification of 40× using a LabPro light microscope and totals counted and recorded. Cells are expressed as total cells×$10^8$ per ml of blood Inhibition of this effect is determined statistically using Graphpad prism.

In the 2 hr study, intravenous DK-$PGD_2$ (IV DK-$PGD_2$) increased the number of peripheral blood leukocytes, mainly lymphocytes, which likely reflects recruitment from bone marrow. This response was dose-dependently reduced by oral Compound 2 resulting in 19 (±23) % and 107 (±9) % inhibition at doses of 10 mg/kg and 30 mg/kg, respectively. Plasma concentrations taken 2.5 hours following oral Compound 2 were 45 nM±36 and 120 nM±46 in the 10 mg/kg and 30 mg/kg dose groups, respectively. Based on these results, the $ED_{50}$ is calculated to be 11 mg/kg with an associated $EC_{50}$ of 50 nM.

In the 18 hr guinea pig study, a significant increase in peripheral blood leukocytes was also observed following IV DK-$PGD_2$ challenge. This response was dose-dependently reduced by oral Compound 2 administered 18 hr prior to DK-$PGD_2$ resulting in 29 (±14) %, 50 (±8) % and 77 (±12) % inhibition of peripheral blood leukocyte numbers at doses of 10 mg/kg, 30 mg/kg and 100 mg/kg, respectively. Significant inhibition of DK-$PGD_2$-induced leukocytosis was achieved in the 100 mg/kg dose group (P<0.05) with a calculated $ED_{50}$ of 63 mg/kg. The concentration of Compound 1 in plasma recovered 18.5 hours following oral dose was 4 nM±7, 21 nM±19 and 17 nM±10 in the 10 mg/kg, 30 mg/kg and 100 mg/kg dose groups, respectively. Using these concentrations and an $ED_{50}$ of 63 mg/kg, the 18-hr $EC_{50}$ for Compound 1 inhibition of IV-DK-$PGD_2$-induced leukocyte influx was calculated to be 18 nM.

In radioligand membrane binding experiments using cells expressing the guinea pig DP2 receptor, Compound 1 has an $IC_{50}$ of 20.3 nM in the presence of 0.2% guinea pig serum albumin. In the guinea pig whole blood eosinophil shape change (ESC) assay, Compound 1 has an $IC_{50}$ of 97.4 nM. Based on the study results, the in vitro and in vivo potencies of Compound 1 are in good agreement suggesting that in vitro binding and/or ESC is a good predictor(s) of the plasma concentration needed to achieve functional activity in an in vivo setting.

Example 20: Guinea Pig Allergic Asthma Model

Compound 2 was evaluated in a guinea pig OVA model in order to determine efficacy in a setting of allergen-induced asthma. As an early indication of a pharmacodynamic response animals were challenged with DK-PGD$_2$ 2 hours post OVA challenge (2.5 hours post Compound 2 administration) and blood was collected 30 minutes later to assess leukocytes counts. DK-PGD$_2$ increased blood leukocytes and this response was blocked with treatment of Compound 2 at all dose levels (30, 60, and 100 mg/kg) suggesting full coverage of the receptor at this early timepoint. OVA challenge caused a significant influx of cells in bronchoalveolar lavage fluid at 23.5 hr post-dose; there was no difference between animals that received OVA only versus those that received OVA plus DK-PGD$_2$. The majority of cells were eosinophils and macrophages with a small, but significant proportion of neutrophils. Compound 2 (30, 60, and 100 mg/kg PO) dose dependently inhibited total cellular influx with significant inhibition at the 60 and 100 mg/kg doses. Eosinophils and neutrophils were also significantly reduced at the 100 mg/kg dose.

In the guinea pig allergic asthma model, Compound 2 exhibited anti-inflammatory activity in the lungs.

Plasma Compound 1 concentrations were determined 3 hours and 24 hours post dose. At 30 mg/kg, a mean plasma concentration of 107.1±31.7 nM was observed 3 hours post dose. At 60 mg/kg, a mean plasma concentration of 371.7±303.8 was observed 3 hours post dose. At 100 mg/kg, a mean plasma concentration of 360.8±131.3 was observed 3 hours post dose. Blood samples collected from guinea pigs 24 hours after oral dose (for each dose amount) revealed a concentration below the lower limit of quantitation of 40 nM.

In radioligand binding experiments using cells expressing the guinea pig DP2 receptor, Compound 1 has an IC$_{50}$ of 20.3 nM in the presence of 0.2% serum albumin and an IC$_{50}$ of 97.4 nM in guinea pig eosinophil shape change. Blood samples collected from guinea pigs 24 hours after oral dose revealed a concentration below the lower limit of quantitation of 40 nM. This value is higher than the DP2 binding IC$_{50}$ of 20 nM but lower than the guinea pig eosinophil shape change IC$_{50}$ of 97.4 nM.

Example 21: Mouse Smoke Model of Chronic Obstructive Pulmonary Disease

A mouse model of acute cigarette smoke exposure was used to determine the effects of Compound 1 on smoke-induced pulmonary inflammation.

BALB/c mice were exposed to the smoke of 7 unfiltered cigarettes per day via whole-body exposure on days 0, 1, and 2 for a total of 1.75 hours per day. Smoke exposure resulted in pulmonary inflammation primarily from an influx of neutrophils and lymphocytes in the bronchoalveolar lavage fluid (BALF). Daily administration of Compound 2 at doses of 10 and 50 mg/kg, PO, significantly reduced BALF neutrophils (a decrease of approx. 50% BALF neutrophils was observed as compared to the untreated group) and showed a trend toward reducing lymphocytes. The plasma concentrations for Compound 1 measured at trough were 85 and 588 nM at 10 mg/kg and 50 mg/kg, respectively.

Example 22: Phase I Study in Humans

This is a phase 1, Single-Center, Double-Blind Study of Compound 2 in healthy volunteers.

Objective:

To assess: (1) the safety and tolerability of single and multiple doses of Compound 2 following oral administration; and (2) the pharmacokinetics (PK) of Compound 2 after single and multiple doses; and (3) the effects of the pharmacodynamic (PD) responses in healthy subjects to Compound 2 as measured by a PGD$_2$-induced eosinophil shape change assay (ESC).

The Single Ascending Dose (SAD) study will include 6 cohorts with 8 subjects each, 6 receiving the active treatment and 2 receiving the placebo. The SAD study will explore doses of 5, 15, 50, 150, 300 and 500 mg/day. Compound 2 (Pattern 1) is administered as API in a Capsule, prepared on site at the clinical pharmacy (see Example 10). Safety monitoring will include: a "how do you feel" (HDYF) question, adverse events reporting, physical examinations, vital signs, ECG's, and a biological assessment (clinical chemistry, hematology and urinalysis). The decision to escalate to the next dose level will be based on the results of medical monitoring, and a blinded interim analysis of pharmacokinetic parameters (AUC, Cmax) and pharmacodynamic responses. Doses may be adjusted based on the occurrence of adverse events. Subjects will be followed on site for 72 hours after dose administration.

The multiple ascending dose (MAD) study will evaluate 7 days of repeat oral administration of Compound 2 in healthy subjects. This study will be initiated after the SAD study has been successfully completed. The primary objective of the study is to investigate the safety and tolerability of multiple oral doses of Compound 2 in healthy subjects. The secondary objectives are to: investigate the pharmacokinetic profile of multiple oral doses of Compound 2 when administered to healthy subjects; evaluate the relationship between exposure to multiple oral doses of Compound 2 and the pharmacodynamic responses in healthy subjects as measured by ESC.

The MAD study will include 4 cohorts with 8 subjects each, 6 receiving active and 2 receiving placebo. Pending the results from the SAD study, three cohorts will evaluate doses of 15, 50, and 150 mg/day, respectively. The dose level of the fourth cohort will be determined based on the results from the SAD study, and may be up to 500 mg/day. Safety monitoring will include: a "how do you feel" (HDYF) question, adverse events reporting, physical examinations, vital signs, ECG's, and a biological assessment (clinical chemistry, hematology, and urinalysis). Dose progression will be based on the clinical safety profile of the prior cohort. Subjects will be followed on site for 72 hours after final dose administration.

Procedure Evaluate Effects of Compound 1 on Ex Vivo PGD$_2$-Induced Blood Eosinophil Shape Change (ESC)

Pre dose blood is drawn and challenged with PGD$_2$ to determine baseline shape change as described above in Example 17. At varying times after dosing blood is drawn for both pharmacokinetic analyses of drug concentration in blood, and also for PGD$_2$ challenge and eosinophil shape change determination. The extent of receptor blockage is determined from the relationship between drug blood concentration and percentage inhibition of eosinophil shape change.

The plasma concentrations of Compound 1 are determined by LC-MS/MS, giving a detection limit of 0.25 ng*mL$^{-1}$.

Pharmacokinetic measurements of Compound 2 includes measurement of the protonated form (Compound 1).

Results

Figure 8:
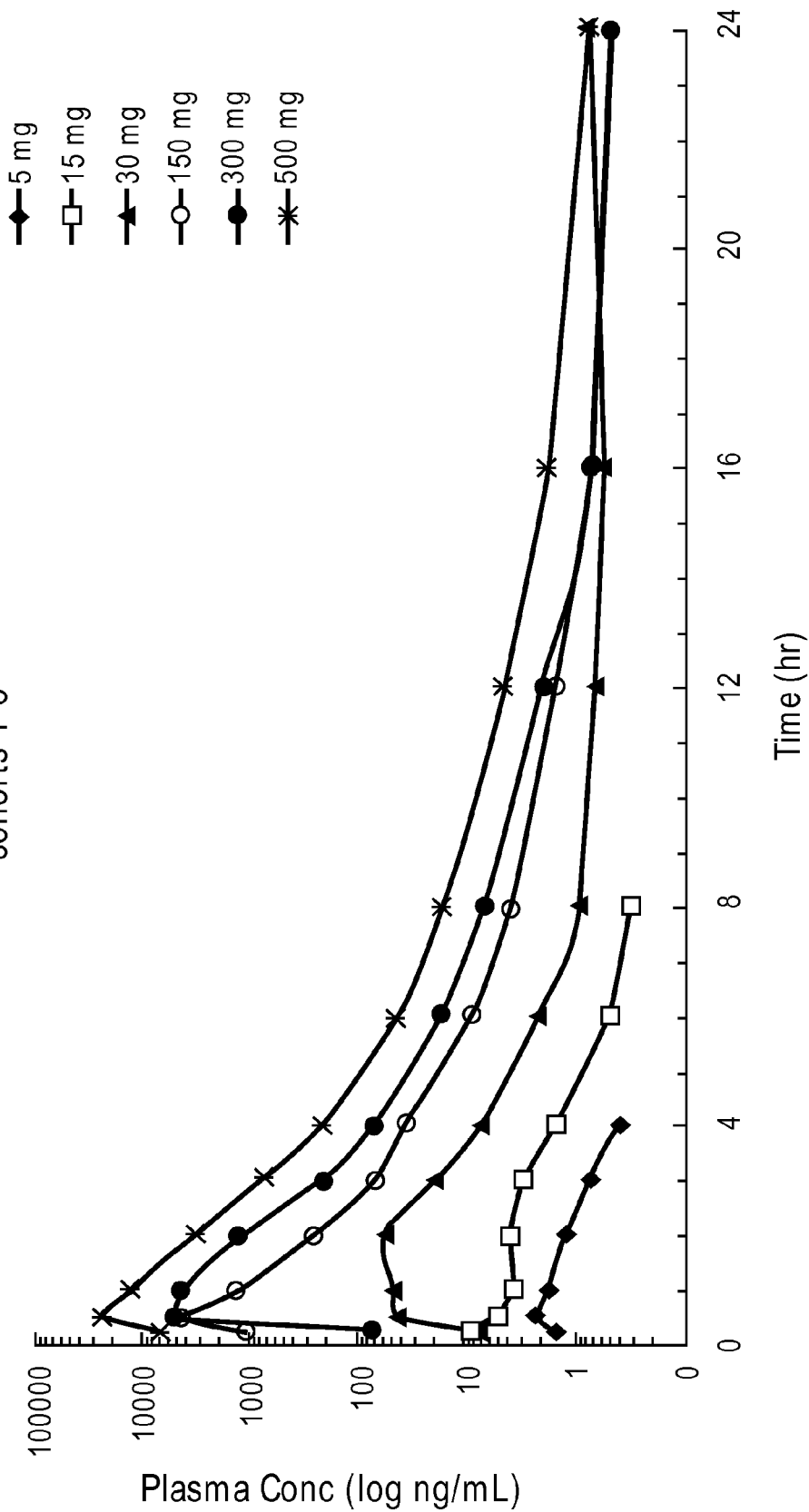
FIG. 8 illustrates the plasma concentrations of Compound 1 after single dose administration of Compound 2 (capsule) to humans.
Figure 9:
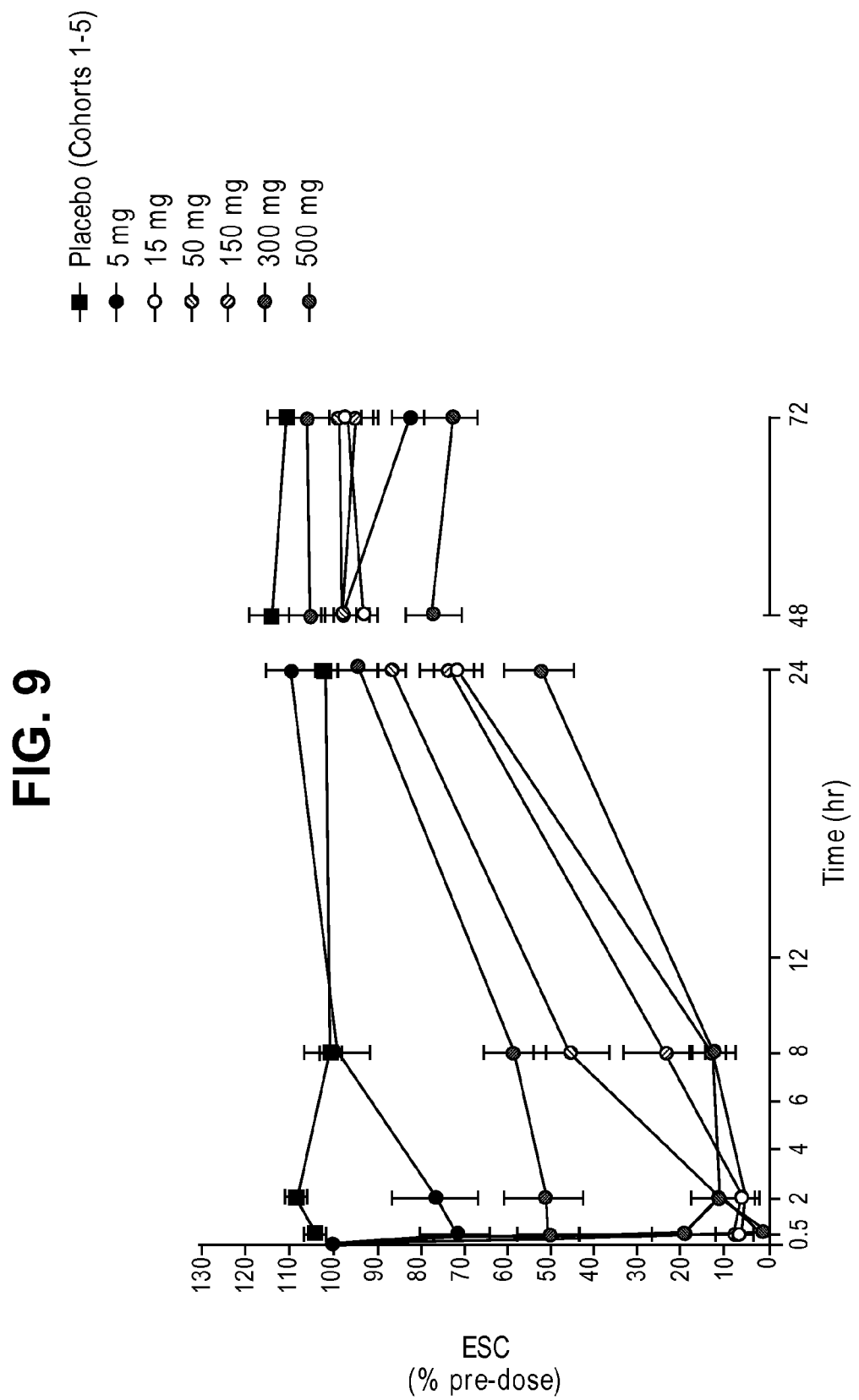
FIG. 9 illustrates the ex vivo $PGD_2$-stimulated eosinophil shape change in whole blood after single dose administration of Compound 2 to humans.
Figure 10:
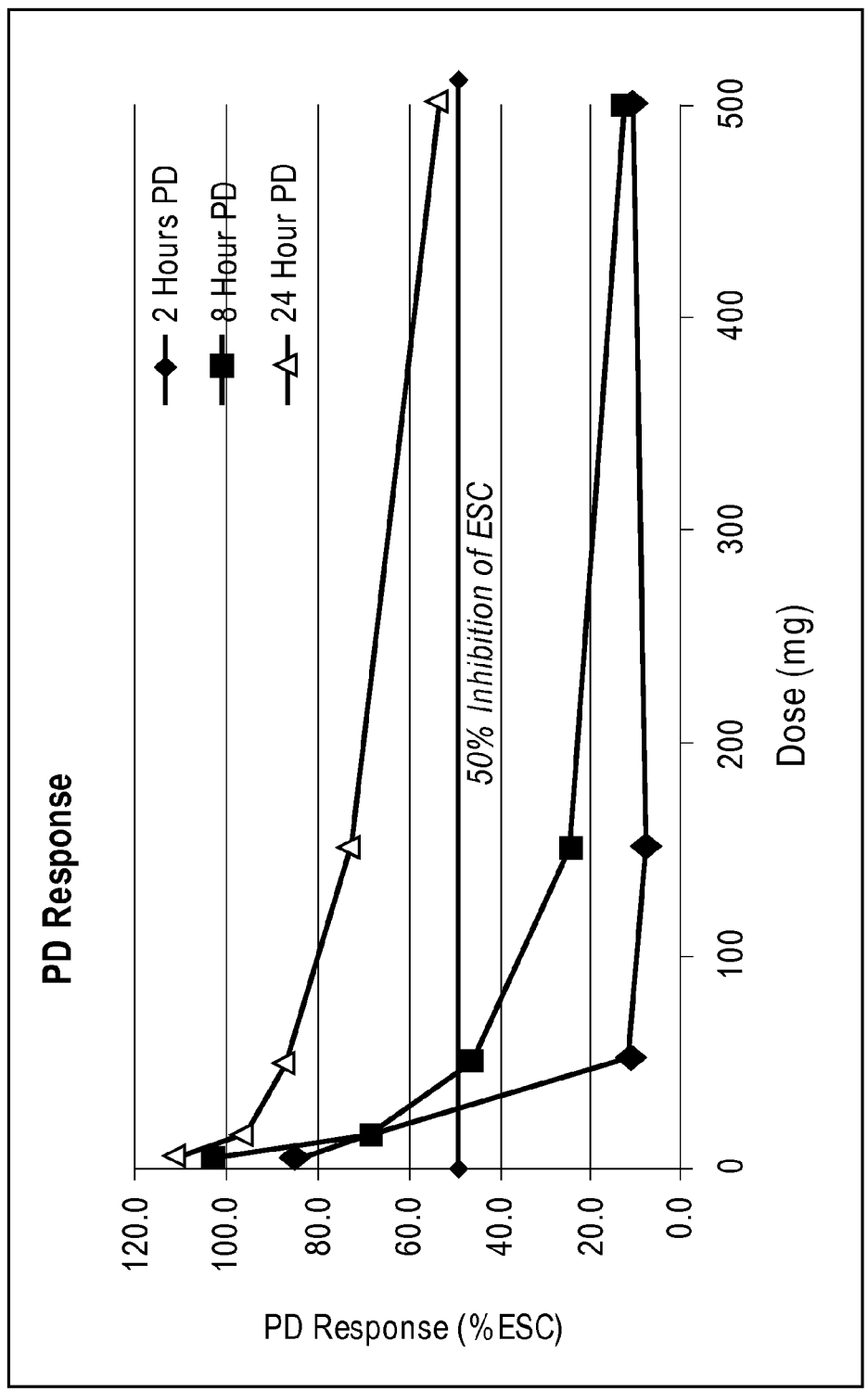
FIG. 10 illustrates the PD response for the SAD study.

The PK and PD effects of Compound 2 after single doses are present in FIGS. 8 to 10 and in Table 13. FIG. 8 and Table 13 illustrates the plasma concentrations of Compound 1 after single dose administration of Compound 2 (capsule) to humans. FIG. 9 illustrates the ex vivo PGD$_2$-stimulated eosinophil shape change in whole blood after single dose administration of Compound 2 to humans. FIG. 10 illustrates the PD response for the SAD study.

TABLE 15

Pharmacokinetic parameters after a single ascending dose.

| Dose Level | Subject Number | $C_{max}$ (ng/mL) | $T_{max}$ (hr) | $AUC_{0-t}$ (ng · hr/mL) | $AUC_{0-\infty}$ (ng · hr/mL) | $\lambda_z$ (1/hr) | $t_{1/2}$ (hr) | CL/F (L/hr) | Vz/F (L) |
|---|---|---|---|---|---|---|---|---|---|
| 5 mg | Mean | 2.69 | 0.542 | 4.85 | 6.20 | 0.598 | 1.22 | 886 | 1466 |
|  | SD | 1.09 | 0.246 | 2.39 | 2.18 | 0.144 | 0.29 | 294 | 488 |
| 15 mg | Mean | 8.31 | 0.625 | 17.0 | 17.5 | 0.574 | 1.23 | 982 | 1764 |
|  | SD | 2.18 | 0.685 | 7.0 | 6.9 | 0.075 | 0.16 | 403 | 874 |
| 50 mg | Mean | 93.4 | 1.20 | 176 | 116 | 0.485 | 1.49 | 643 | 1496 |
|  | SD | 76.7 | 0.76 | 159 | 94 | 0.110 | 0.38 | 374 | 1156 |
| 150 mg | Mean | 4632 | 0.542 | 3450 | 3455 | 0.130 | 7.86 | 161 | 1408 |
|  | SD | 2506 | 0.246 | 2048 | 2050 | 0.076 | 6.71 | 294 | 2483 |
| 300 mg | Mean | 6690 | 0.92 | 6974 | 6978 | 0.19 | 6.32 | 53.4 | 351 |
|  | SD | 5414 | 0.58 | 3892 | 3895 | 0.11 | 6.44 | 22.8 | 185 |
| 500 mg | Mean | 25655 | 0.583 | 26000 | 26007 | 0.0904 | 14.1 | 21.8 | 501 |
|  | SD | 11867 | 0.204 | 9700 | 9697 | 0.0631 | 11.9 | 8.6 | 573 |

Compound 2 in a capsule was well tolerated at 5 to 500 mg singles doses. The following conclusions are observed from the SAD study:

pharmacodynamic dose response—maximal inhibition achieved at >150 mg at 0.5, 2 hr and 8 hr; 24 hr PD response of ~50% at 500 mg dose.

PK/exposure increases with dose—Dose proportion at 5-50 mg. Supra-proportional from 50 to 500 mg. Half life increases with dose (1.2 hr to 7 hr). Long elim. $t_{1/2}$ at 150 and 500 mg dose, up to 18 hr.

Inhibition of DP$_2$ in humans with prostaglandin D$_2$-dependent or prostaglandin D$_2$-mediated conditions or diseases provides benefit in the condition or disease. Compound 1, or a pharmaceutically acceptable salt thereof (e.g. Compound 2) is useful in the treatment or prevention of prostaglandin D$_2$-dependent or prostaglandin D$_2$-mediated conditions or diseases.

Study 2: Clinical Trial Evaluating Effect of Compound 1 on Mild to Moderate Asthma In this randomized, parallel, double-blind, placebo-controlled study in individuals with childhood onset, atopic, mild to moderate asthma the control of asthma (Asthma Control Questionnaire) and reduction of asthma symptoms is determined following 4 weeks treatment, once daily with Compound 2. One hundred subjects (50 active, 50 placebo) are used. Subjects are dosed once daily for 4 weeks with either placebo or an amount of Compound 2 that results in complete DP2 receptor block in an ex-vivo PGD$_2$-induced blood eosinophil shape change pharmacodynamic study as described above. After 4 weeks, subjects are evaluated for asthma control using the Asthma Control Questionnaire and for changes in asthma symptoms, exacerbations, Forced Expiratory Volume (FEV), Peak Expiratory Flow Rate (PEFR), Beta-2 agonist use. In addition, changes in serum IgE and ECP (eosinophil cationic protein) concentrations and sputum inflammatory cell differentials, Th2 cytokines and ECP are determined for treated and placebo.

Study 3—Vienna Challenge Chamber Study

Study design: The study is a randomised, double blind, placebo controlled, two way crossover evaluation of Compound 2 given orally for eight days. There is a screening period of one week and a washout period of three weeks between the two treatment periods.

There is a follow up one week after the last dose of study drug. The group of patients who receive the study drug for the first treatment period and placebo for the second are designated group A, while the group of patients who receive placebo for the first treatment period and the study drug for the second treatment period are designated group B.

Treatment plan and methods: The subjects undergo a complete screening assessment to determine a baseline response to allergens. This screening assessment takes place one week prior to the start of dosing.

Subjects commence dosing with Compound 2 or placebo on Day 1 of each treatment period of the study. Adverse events, total nasal symptom score and concomitant medications are noted.

Subjects report back to the clinic on Day 2 of each treatment period for a 6 hour allergen challenge. The following measurements are obtained:

Total nasal symptom score (TNSS) (obstruction, rhinorrhoea, itch, sneeze) with each symptom scored on a categorical scale from 0 to 3 pre-challenge, every 15 mins from 0 to 6 h post-start of challenge Eye symptom score (watery eyes, itchy eyes, red eyes) with each symptom scored on a categorical scale from 0 to 3 pre-challenge, every 15 mins from 0 to 6 h post-start of challenge Other symptoms (cough, itchy throat, itchy ears) with each symptom scored on a categorical scale from 0 to 3 pre-challenge and every 15 mins from 0 to 6 h post-start of challenge Subjects report back to the clinic on Day 8 of each treatment period for a 6 hour allergen challenge and the measurements obtained on Day 2 are repeated.

A final follow-up visit is conducted one week after the last dose of test article in Treatment Period 2.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline form of 2-(3-(2-((tert-butylthio)methyl)-4-(2,2-dimethyl-propionylamino)phenyloxy)-4-methoxyphenyl)acetic acid, sodium salt

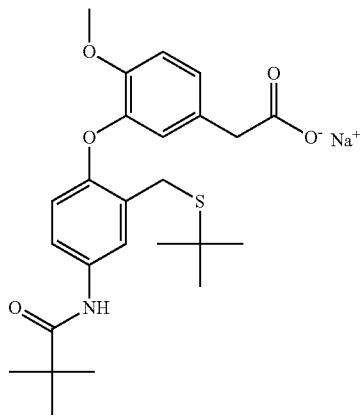 [SMILES: COc1ccc(CC(=O)[O-])cc1Oc1ccc(NC(=O)C(C)(C)C)cc1CSC(C)(C)C ; [Na+]]

or a solvate thereof.

2. The crystalline form of claim 1 having at least one of the following properties: (a) an X-ray powder diffraction (XRPD) pattern with characteristic peaks at 3.7° 2-Theta, 13.5° 2-Theta, 17.1° 2-Theta, and 18.8° 2-Theta; (b) an X-ray powder diffraction (XRPD) pattern with characteristic peaks at 3.7° 2-Theta, 13.5° 2-Theta, 17.1° 2-Theta, and 18.8° 2-Theta and at least one additional characteristic peak selected from 6.8° 2-Theta, 8.7° 2-Theta, 11.1° 2-Theta, 15.7° 2-Theta, 17.5° 2-Theta, and 17.9° 2-Theta; (c) an X-ray powder diffraction (XRPD) pattern substantially the same as shown in FIG. 2; (d) a DSC thermogram with endotherms at about 70° C., about 122° C., and about 138° C.; or (e) a DSC thermogram substantially the same as FIG. 3.

3. The crystalline form of claim 2, wherein the crystalline form of 2-(3-(2-((tert-butylthio)methyl)-4-(2,2-dimethyl-propionylamino)phenoxy)-4-methoxyphenyl)acetic acid, sodium salt has properties (a), (c), (d), and (e).

4. The crystalline form of claim 1, wherein the crystalline form of 2-(3-(2-((tert-butylthio)methyl)-4-(2,2-dimethyl-propionylamino)phenoxy)-4-methoxyphenyl)acetic acid, sodium salt was obtained from a solution comprising heptane and acetone.

5. The crystalline form of claim 1, wherein the crystalline form of 2-(3-(2-((tert-butylthio)methyl)-4-(2,2-dimethyl-propionylamino)phenoxy)-4-methoxyphenyl)acetic acid, sodium salt is solvated.

6. A pharmaceutical composition comprising crystalline 2-(3-(2-((tert-butylthio)methyl)-4-(2,2-dimethyl-propionylamino)phenoxy)-4-methoxyphenyl)acetic acid, sodium salt, and at least one ingredient selected from pharmaceutically acceptable carriers, diluents and excipients.

7. The pharmaceutical composition according to claim 6, wherein the pharmaceutical composition is in the form of a pill, capsule, or tablet.

8. The pharmaceutical composition according to claim 6, wherein the pharmaceutical composition comprises about 0.5 mg to about 1000 mg of crystalline 2-(3-(2-((tert-butylthio)methyl)-4-(2,2-dimethyl-propionylamino)phenoxy)-4-methoxyphenyl)acetic acid, sodium salt.

9. A method of treating a respiratory disease or condition, an inflammatory disease or condition or an allergic disease or condition, or combinations thereof, in a mammal comprising administering to the mammal a pharmaceutical composition according to claim 6 wherein the respiratory disease or condition, inflammatory disease or condition or allergic disease or condition is asthma or rhinitis.

10. A method of treating asthma in a mammal comprising administering to the mammal a pharmaceutical composition according to claim 6.

11. A method of treating rhinitis in a mammal comprising administering to the mammal a pharmaceutical composition according to claim 6.

* * * * *